United States Patent
Ichikawa et al.

(10) Patent No.: US 8,889,333 B2
(45) Date of Patent: Nov. 18, 2014

(54) SALT, PHOTORESIST COMPOSITION, AND METHOD FOR PRODUCING PHOTORESIST PATTERN

(75) Inventors: Koji Ichikawa, Osaka (JP); Isao Yoshida, Osaka (JP); Yuko Yamashita, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 35 days.

(21) Appl. No.: 13/443,166

(22) Filed: Apr. 10, 2012

(65) Prior Publication Data

US 2012/0264060 A1 Oct. 18, 2012

(30) Foreign Application Priority Data

Apr. 13, 2011 (JP) ................................. 2011-088879
May 16, 2011 (JP) ................................. 2011-109086
Sep. 29, 2011 (JP) ................................. 2011-214045

(51) Int. Cl.
| | | |
|---|---|---|
| G03F 7/004 | (2006.01) | |
| C07C 303/32 | (2006.01) | |
| C07C 309/06 | (2006.01) | |
| C07C 309/07 | (2006.01) | |
| C07C 309/12 | (2006.01) | |
| C07C 309/19 | (2006.01) | |
| G03F 7/039 | (2006.01) | |
| C07C 381/12 | (2006.01) | |
| C07C 309/17 | (2006.01) | |
| C07C 25/18 | (2006.01) | |

(52) U.S. Cl.
CPC ............. *C07C 309/17* (2013.01); *C07C 309/07* (2013.01); *C07C 309/19* (2013.01); *G03F 7/0046* (2013.01); *G03F 7/0397* (2013.01); *C07C 309/06* (2013.01); *C07C 381/12* (2013.01); *C07C 303/32* (2013.01); *G03F 7/0392* (2013.01); *C07C 2101/14* (2013.01); *G03F 7/0045* (2013.01); *C07C 25/18* (2013.01); *C07C 2103/74* (2013.01); *C07C 309/12* (2013.01); *Y10S 430/111* (2013.01); *Y10S 430/122* (2013.01); *Y10S 430/123* (2013.01)
USPC ........ 430/270.1; 430/326; 430/910; 430/921; 430/922; 562/100; 562/109; 562/113

(58) Field of Classification Search
CPC ... G03F 7/0045; G03F 7/0397; C07C 303/32; C07C 309/06; C07C 309/07; C07C 309/12; C07C 309/19
USPC ...................... 430/270.1, 910, 326, 921, 922; 562/100, 109, 113
See application file for complete search history.

(56) References Cited

U.S. PATENT DOCUMENTS

| | | | |
|---|---|---|---|
| 5,914,219 A | 6/1999 | Funhoff et al. | |
| 7,304,175 B2 | 12/2007 | Harada et al. | |
| 7,439,006 B2 * | 10/2008 | Yoshida et al. | 430/270.1 |
| 7,579,132 B2 * | 8/2009 | Harada et al. | 430/270.1 |
| 8,530,138 B2 * | 9/2013 | Yoshida et al. | 430/270.1 |
| 2006/0194982 A1 | 8/2006 | Harada et al. | |
| 2007/0027336 A1 | 2/2007 | Yoshida et al. | |
| 2007/0078269 A1 | 4/2007 | Harada et al. | |
| 2007/0100096 A1 * | 5/2007 | Harada et al. | 526/135 |
| 2007/0122750 A1 | 5/2007 | Yamaguchi et al. | |
| 2008/0076063 A1 | 3/2008 | Yoshida et al. | |
| 2008/0081925 A1 | 4/2008 | Sakamoto et al. | |
| 2008/0193874 A1 * | 8/2008 | Takata et al. | 430/270.1 |
| 2009/0208871 A1 | 8/2009 | Kawaue et al. | |
| 2011/0117493 A1 * | 5/2011 | Ichikawa et al. | 430/270.1 |
| 2011/0117494 A1 * | 5/2011 | Ichikawa et al. | 430/270.1 |
| 2011/0117495 A1 * | 5/2011 | Ichikawa et al. | 430/270.1 |
| 2012/0052440 A1 | 3/2012 | Yoshida et al. | |

FOREIGN PATENT DOCUMENTS

JP 2012-6907 A 1/2012

* cited by examiner

*Primary Examiner* — John Chu
(74) *Attorney, Agent, or Firm* — Birch, Stewart, Kolasch & Birch, LLP

(57) ABSTRACT

A salt represented by formula (I):

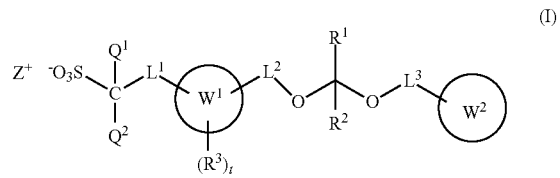

wherein $Q^1$ and $Q^2$ independently each represent a fluorine atom or a C1-C6 perfluoroalkyl group, $L^1$ represents a C1-C17 divalent saturated hydrocarbon group in which a methylene group may be replaced by an oxygen atom or a carbonyl group, $L^2$ and $L^3$ respectively represent a single bond or a C1-C6 divalent saturated alkyl group in which a methylene group may be replaced by an oxygen atom or a carbonyl group, ring $W^1$ and ring $W^2$ respectively represent a C3-C36 hydrocarbon ring, $R^1$ and $R^2$ respectively represent a hydrogen atom or C1-C6 alkyl group, $R^3$ represents C1-C6 alkyl group, t represents an integer of 0 to 2 and $Z^+$ represents an organic counter ion.

8 Claims, No Drawings

SALT, PHOTORESIST COMPOSITION, AND METHOD FOR PRODUCING PHOTORESIST PATTERN

This nonprovisional application claims priority under 35 U.S.C. §119(a) on Patent Applications No. 2011-088879 filed in JAPAN on Apr. 13, 2011, No. 2011-109086 filed in JAPAN on May 2011 and No. 2011-214045 filed in JAPAN on Sep. 29, 2011, the entire contents of which are hereby incorporated by reference.

FIELD OF THE INVENTION

The present invention relates to a salt usable for an acid generator, a photoresist composition and a method for producing a photoresist pattern.

BACKGROUND OF THE INVENTION

A photoresist composition is used for semiconductor microfabrication employing a lithography process, which contains an acid generator comprising a salt.

US2008/0081925A1 discloses a salt represented by the following formula:

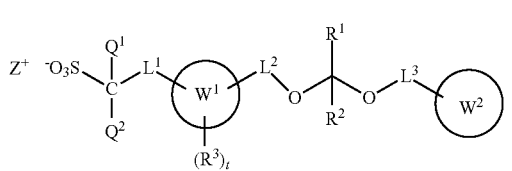

and a photoresist composition containing the same as an acid generator.

SUMMARY OF THE INVENTION

The present invention is to provide a salt for suitable for an acid generator and a photoresist composition comprising the same. The present invention relates to the followings:

<1> A salt represented by formula (I):

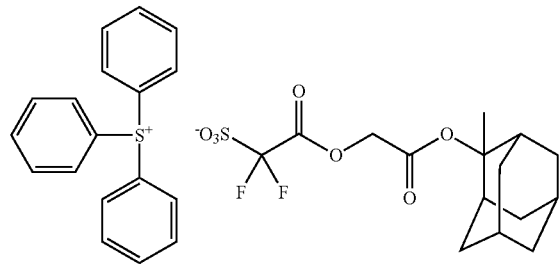

wherein $Q^1$ and $Q^2$ independently each represent a fluorine atom or a C1-C6 perfluoroalkyl group,
$L^1$ represents a C1-C17 divalent saturated hydrocarbon group in which a methylene group may be replaced by an oxygen atom or a carbonyl group,
$L^2$ and $L^3$ each independently represent a single bond or a C1-C6 divalent saturated alkyl group in which a methylene group may be replaced by an oxygen atom or a carbonyl group,
ring $W^1$ and ring $W^2$ each independently represent a C3-C36 hydrocarbon ring,
$R^1$ and $R^2$ each independently represent a hydrogen atom or C1-C6 alkyl group,
$R^3$ represents a C1-C6 alkyl group,
t represents an integer of 0 to 2 and
$Z^+$ represents an organic counter ion.
<2> The salt according to <1>, wherein $L^1$ represents *—CO—O—, where * represents a binding position to —C($Q^1$)($Q^2$)-.
<3> The salt according to <1> or <2>, wherein $L^2$ is a carbonyl group.
<4> The salt according to any one of <1> to <3>, wherein $L^3$ is a single bond or a methylene group.
<5> An acid generator comprising the salt according to any one of <1> to <4>.
<6> A photoresist composition comprising the acid generator according to <5> and a resin having an acid-labile group, being insoluble or poorly soluble in an aqueous alkali solution but becoming soluble in an aqueous alkali solution by the action of an acid.
<7> The photoresist composition according to <6>, which further comprises a basic compound.
<8> A process for producing a photoresist pattern comprising the following steps (1) to (5):
(1) a step of applying the photoresist composition according to <6> or <7> on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

DESCRIPTION OF PREFERRED EMBODIMENTS

First, the salt represented by the formula (I) will be illustrated.

The salt of the present invention is represented by formula (I):

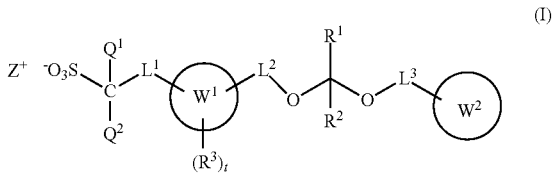

wherein $Q^1$ and $Q^2$ each independently represent a fluorine atom or a C1-C6 perfluoroalkyl group,
$L^1$ represents a C1-C17 divalent saturated hydrocarbon group in which a methylene group may be replaced by an oxygen atom or a carbonyl group,
$L^2$ and $L^3$ each independently represent a single bond or a C1-C6 divalent saturated alkyl group in which a methylene group may be replaced by an oxygen atom or a carbonyl group,
ring $W^1$ and ring $W^2$ each independently represent a C3-C36 hydrocarbon ring,
$R^1$ and $R^2$ each independently represent a hydrogen atom or C1-C6 alkyl group,
$R^3$ represents a C1-C6 alkyl group,
t represents an integer of 0 to 2 and
$Z^+$ represents an organic counter ion.

Hereinafter, the moiety corresponding to the part except $Z^+$ in formula (I) and having a negative charge is sometimes referred to an "sulfonic acid anion".

Examples of the C1-C6 perfluoroalkyl group represented by $Q^1$ and $Q^2$ include a trifluoromethyl group, a pentafluoroethyl group, a heptafluoropropyl group, a nonafluorobutyl group, an undecafluoropentyl group and a tridecafluorohexyl group. It is preferred that $Q^1$ and $Q^2$ independently each represent a fluorine atom or a trifluoromethyl group, and it is more preferred that $Q^1$ and $Q^2$ are fluorine atoms.

$L^1$ represents a C1-C17 divalent saturated hydrocarbon group in which a methylene group may be replaced by an oxygen atom or a carbonyl group. Such divalent saturated hydrocarbon group includes a linear chain alkanediyl group, a branched chain alkanediyl group, a monocyclic or dicyclic divalent alicyclic hydrocarbon group, and a group in which two or more of these alkanediyl and alicyclic hydrocarbon groups have been combined.

Examples of $L^1$ include linear hydrocarbon groups such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, an ethane-1,1-diyl group, a propane-1,1-diyl group;

branched chain groups including a group formed by attaching a side chain to a linear hydrocarbon group, such as a butan-1,3-diyl group, a2-methylpropane-1,3-diyl group, a2-methylpropane-1,2-diyl group, a pentane-1,4-diyl group, and a 2-methylbutane-1,4-diyl group;

a monocyclic divalent alicyclic hydrocarbon groups such as a cyclobutan-1,3-diyl group, cyclopentane-1,3-diyl group, a cyclohexane-1,2-diyl group, a 1-methylcyclohexane-1,2-diyl group, cyclohexane-1,4-diyl group, cyclooctane-1,2-diyl group, and a cyclooctane-1,5-diyl group; and a polycyclic divalent alicyclic hydrocarbon groups such as a norbornane-2,3-diyl group, nobornane-1,4-diyl group, a norbornane -2,5-diyl group, an amadantane-1,2-diyl group, an amadantane-1,5-diyl group and an amadantane-1,6-diyl group.

When $L^1$ represents a C1-C17 divalent saturated hydrocarbon group in which a methylene group has been replaced by an oxygen atom or a carbonyl group, examples of $L^1$ include the moiety represented by any one of formulae (b1-1) to (b1-7) as follow.

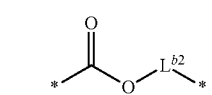
(b1-1)

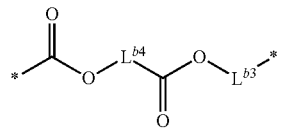
(b1-2)

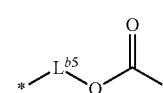
(b1-3)

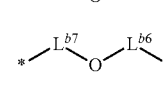
(b1-4)

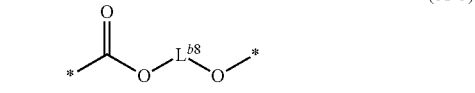
(b1-5)

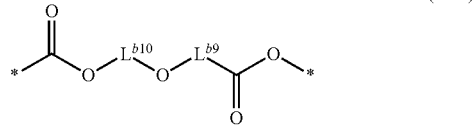
(b1-6)

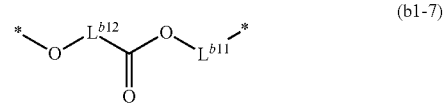
(b1-7)

wherein $L^{b2}$ represents a single bond or a C1-C15 divalent hydrocarbon group, $L^{b3}$ represents a single bond or a C1-C12 divalent hydrocarbon group, $L^{b4}$ represents a C1-C13 divalent hydrocarbon group provided that the total carbon atoms of $L^{b3}$ and $L^{b4}$ is up to 13, $L^{b5}$ represents a C1-C15 divalent hydrocarbon group, $L^{b6}$ represents a single bond or a C1-C15 divalent hydrocarbon group, $L^{b7}$ represents a C1-C15 divalent hydrocarbon group, with the proviso that total carbon number of $L^{b6}$ and $L^{b7}$ is up to 16, $L^{b8}$ represents C1-C14 divalent hydrocarbon group, $L^{b9}$ represents a single bond or a C1-C11 saturated hydrocarbon group, $L^{b10}$ represents a C1-C12 divalent hydrocarbon group, with the proviso that total carbon number of $L^{b9}$ and $L^{b10}$ is up to 12, $L^{b11}$ represents a single bond or a C1-C13 divalent hydrocarbon group, $L^{b12}$ represents C1-C14 divalent hydrocarbon group, with the proviso that total carbon number of $L^{b11}$ and $L^{b12}$ is up to 14,

* represents a binding position, * of the left side represents a binding position to $-C(Q^1)(Q^2)$-, and * of the right side represents a binding position to the ring $W^1$.

$L^1$ is preferably the moieties represented by any one of formulae (b1-1) to (b1-4), more preferably the moieties represented by any formula (b1-1) or (b1-3), still more preferably the moieties represented by formula (b1-1). Among the moieties represented by formula (b1-1), preferred are those in which $L^{b2}$ represents a single bond or a methylene group, and more preferred are one in which $L^{b2}$ represents a single bond, i.e., *—CO—O— where * represents a binding position to —C(Q$^1$)(Q$^2$)-.

$L^2$ and $L^3$ each independently represent a single bond or a C1-C6 divalent saturated hydrocarbon group.

Such saturated hydrocarbon group includes a linear chain alkanediyl group or a branched chain alkanediyl group.

Examples of the linear hydrocarbon groups include a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, an ethane-1,1-diyl group, a propane-1,1-diyl group. Examples of branched chain groups include a group formed by attaching a side chain to a linear hydrocarbon group, such as a butan-1,3-diyl group, a 2-methylpropane-1,3-diyl group, a 2-methylpropane-1,2-diyl group, a pentane-1,4-diyl group, and a 2-methylbutane-1,4-diyl group.

Examples of the divalent saturated hydrocarbon group in which a methylene group may be replaced by an oxygen atom or a carbonyl group include a carbonyl group (—CO—), —CO—O—CH$_2$—CO—.

L$^2$ represents preferably a single bond, methylene group, a carbonyl group or a (C1-C4 alkyl)carbonyl group, more preferably a single bond, methylene group or a carbonyl group, still more preferably a carbonyl group.

L$^3$ represents preferably a single bond, a C1-C4 alkylene group such as a methylene group or a carbonyl group, more preferably a single bond, or a methylene group, and still more preferably a single bond.

Examples of C1-C6 alkyl group represented by R$^1$, R$^2$ and R$^3$ include a methyl group, an ethyl group, a propyl group, a butyl group, a pentyl group and a hexyl group.

R$^1$ and R$^2$ include preferably hydrogen atom, a C1-C4 alkyl group such as a methyl group and an ethyl group, more preferably hydrogen atom and a methyl group, and still more preferably hydrogen atom.

R$^3$ includes preferably a C1-C4 alkyl group, more preferably a methyl group and an ethyl group, and still more preferably a methyl group. Herein, "hydrocarbon ring" represented by ring W$^1$ and ring W$^2$ refers to a hydrocarbon ring consisting of carbon atoms and hydrogen atoms.

Such hydrocarbon ring includes preferably C5-C18 hydrocarbon ring, more preferably C5-C12 hydrocarbon ring, which may be a monocyclic, bicyclic or tricyclic hydrocarbon group. Specific examples of the hydrocarbon ring include a cycloalkyl group such as cyclohexane, adamantane ring and an aromatic group such as benzene ring, preferably adamantane ring.

In the formula (I), examples of the moiety represented by formula (I-A)

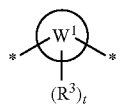
(I-A)

wherein R$^3$, ring W$^1$ and t are defined as above include the formulae as follow,

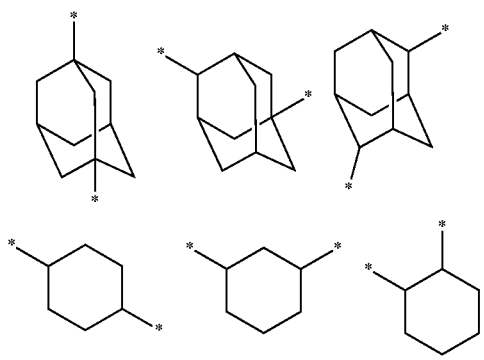

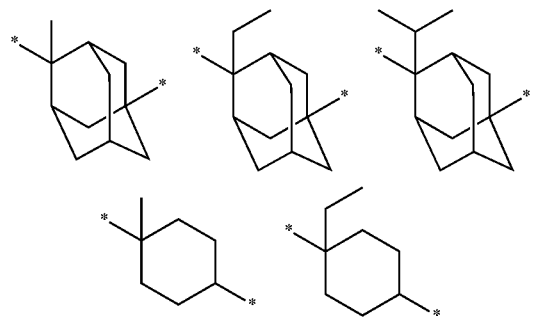

In formula (I), t is preferably 0 or 1, more preferably 0. Specific examples of ring W$^2$ include those represented by the formulae as follow.

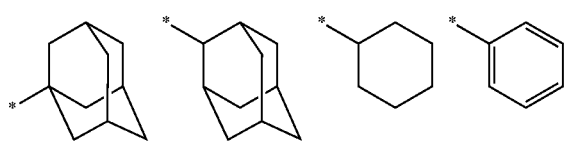

Examples of the anion moiety of SALT (I) include the following.

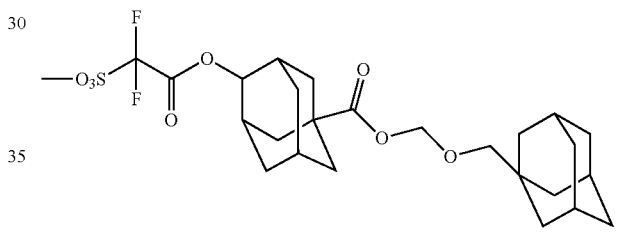
(Ia1-1-1)

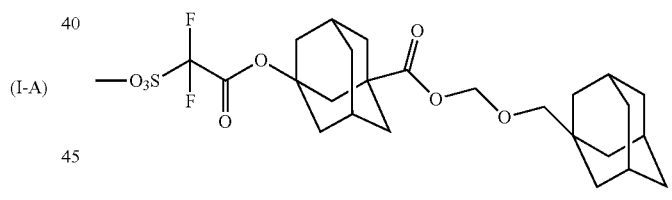
(Ia1-1-2)

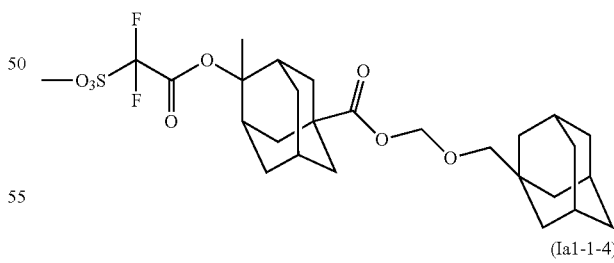
(Ia1-1-3)

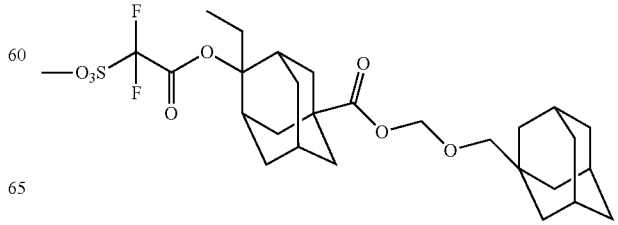
(Ia1-1-4)

(Ia1-1-5)
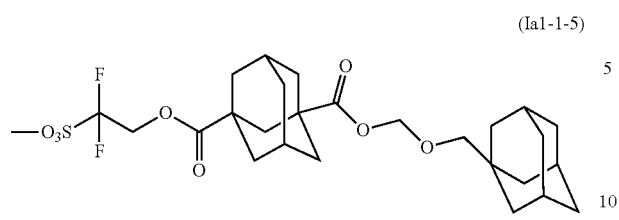
(Ia1-1-11)
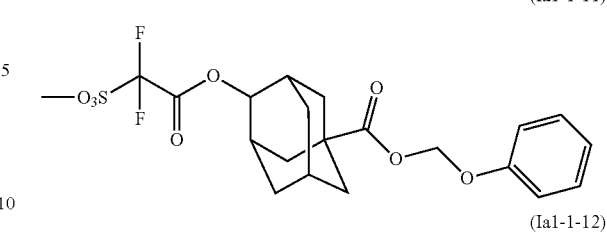
(Ia1-1-6)
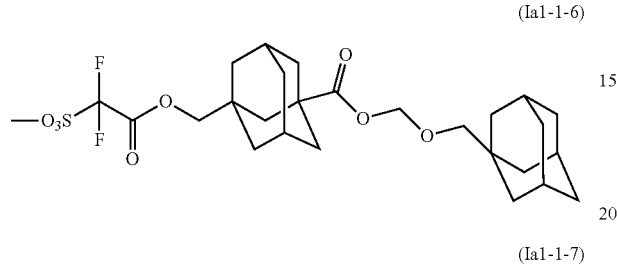
(Ia1-1-12)
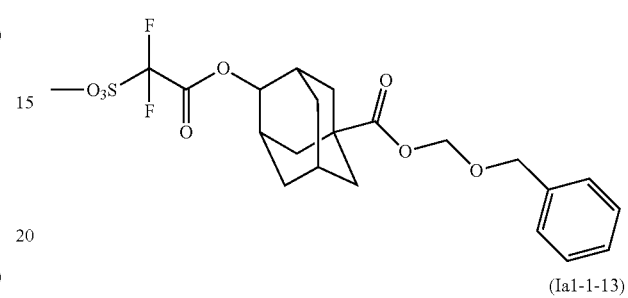
(Ia1-1-7)
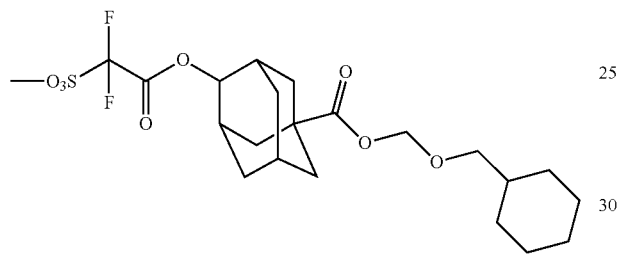
(Ia1-1-13)
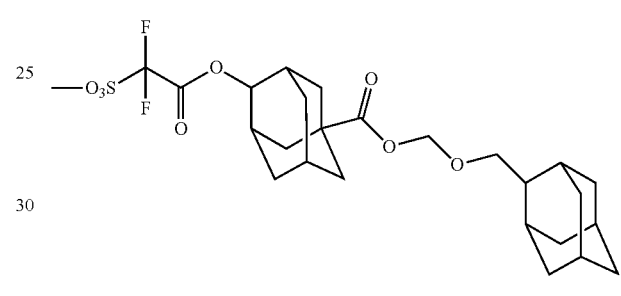
(Ia1-1-8)
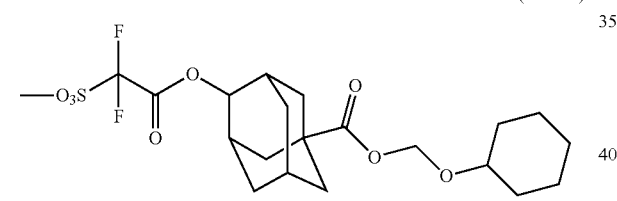
(Ia1-1-14)
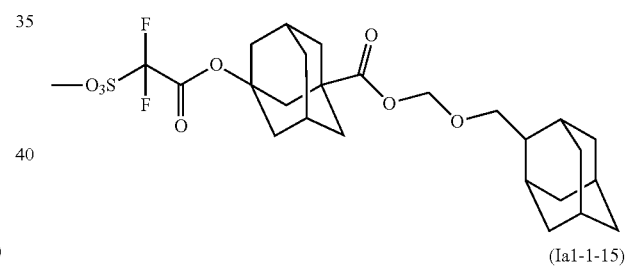
(Ia1-1-9)
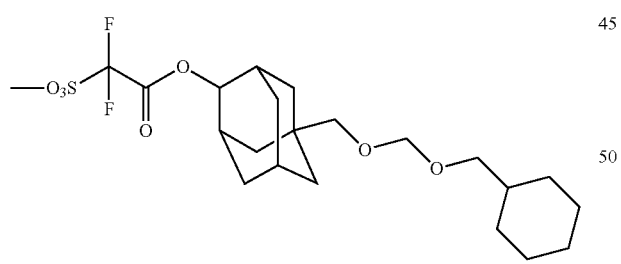
(Ia1-1-15)
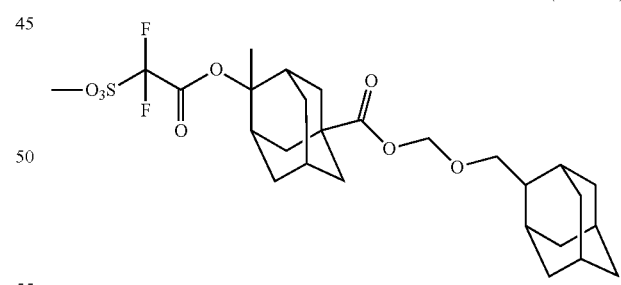
(Ia1-1-10)
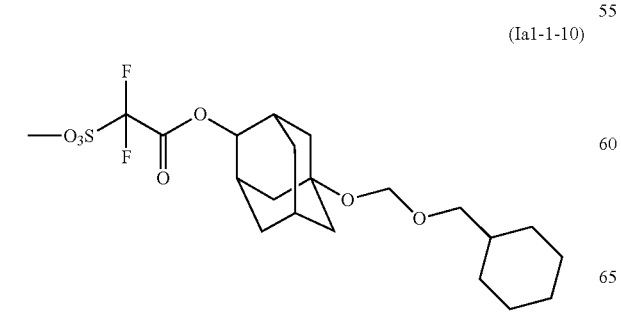
(Ia1-1-16)
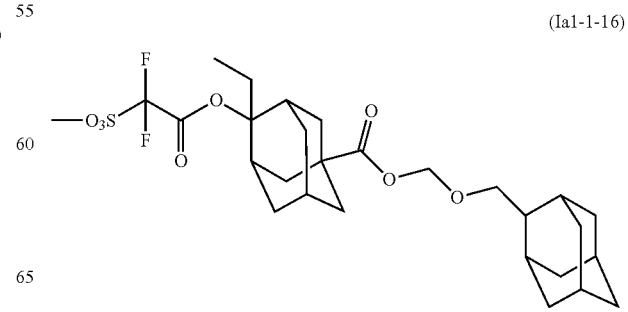

(Ia1-1-17)
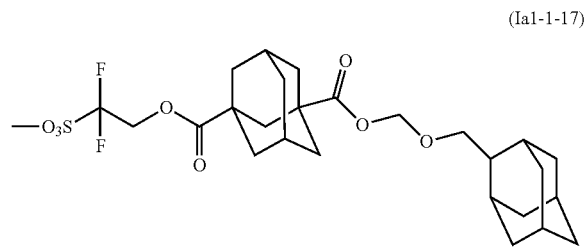
(Ia1-1-22)
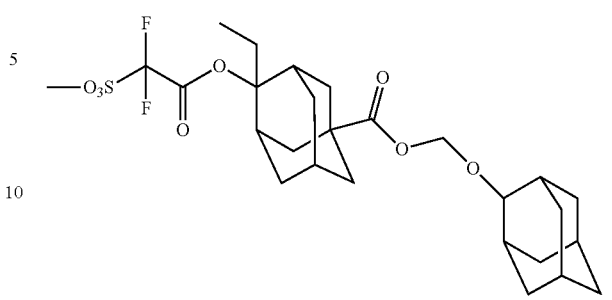
(Ia1-1-18)
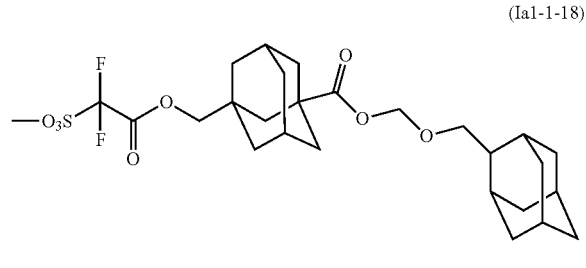
(Ia1-1-23)
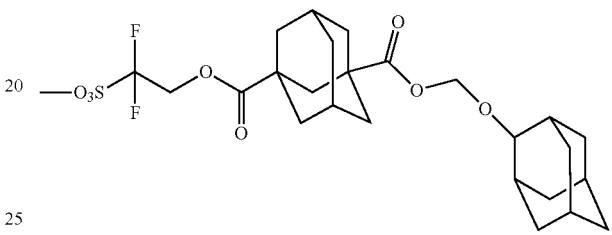
(Ia1-1-19)
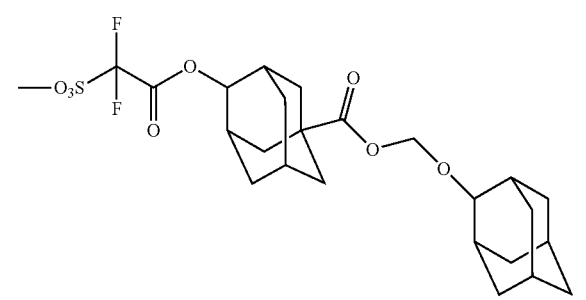
(Ia1-1-24)
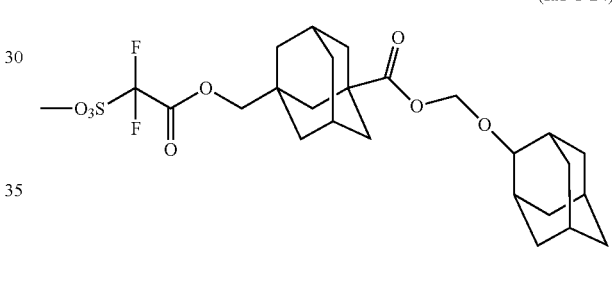
(Ia1-1-20)
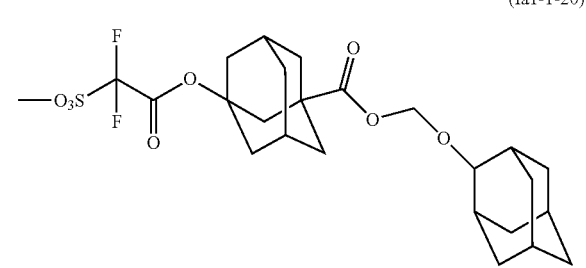
(Ia1-1-25)
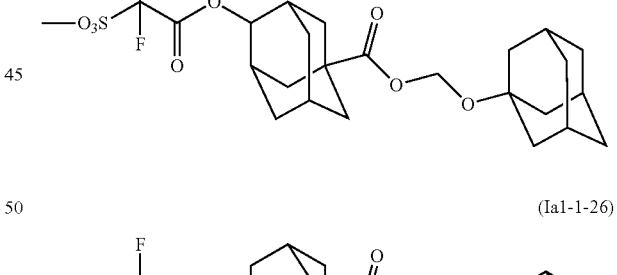
(Ia1-1-21)
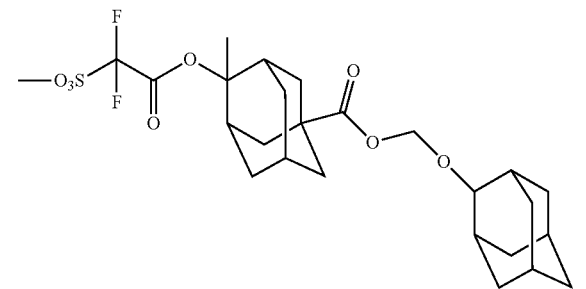
(Ia1-1-26)
(Ia1-1-27)
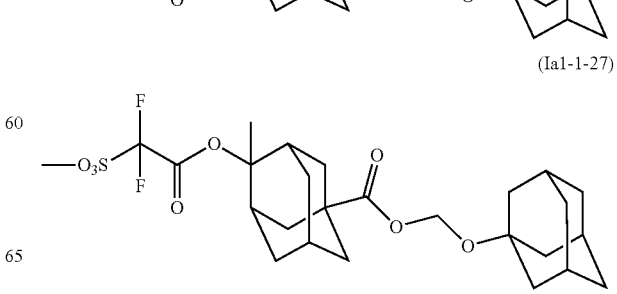

(Ia1-1-28)
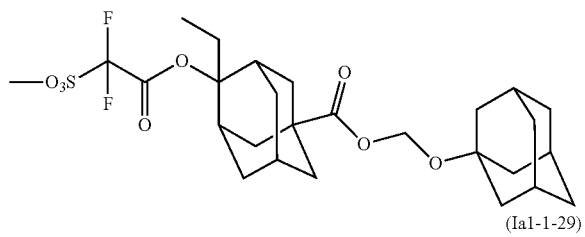
(Ia1-1-29)

(Ia1-1-30)
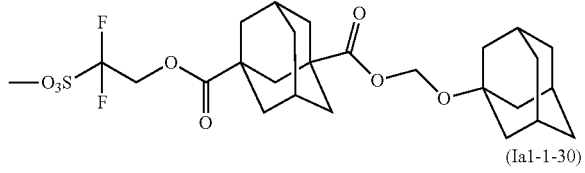

(Ia1-1-31)
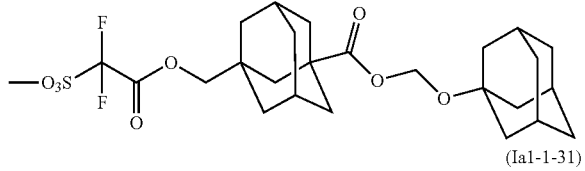

(Ia1-1-32)
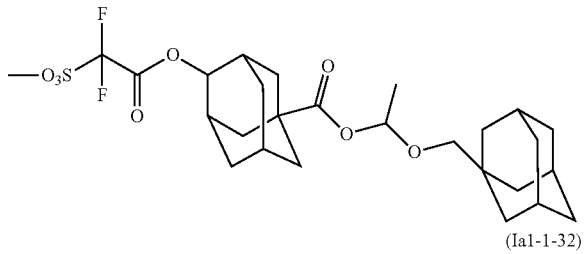

(Ia1-1-33)
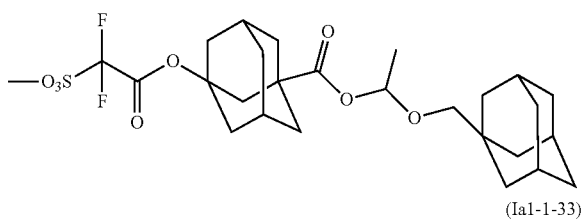

(Ia1-1-34)
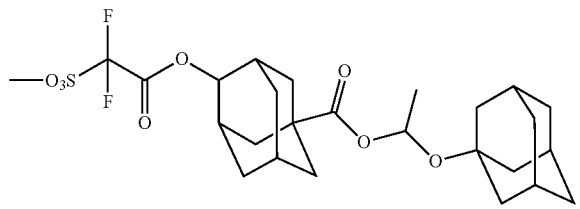

(Ia1-1-35)

(Ia1-1-36)

Examples of the organic counter ion represented by Z* include an organic onium cation such as an organic sulfonium cation, an organic iodonium cation, an organic ammonium cation, a benzothiazolium cation and an organic phosphonium cation, and an organic sulfonium cation and an organic iodonium cation are preferable, and an arylsulfonium cation is more preferable. Herein, the arylsulfonium includes those having one, two or three aryl groups.

Preferable examples of the organic counter ion represented by Z⁺ include the organic cations represented by the formulae (b2-1) to (b2-4):

(b2-1)
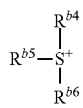

(b2-2)
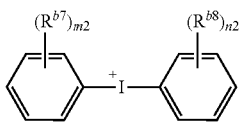

(b2-3)
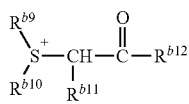

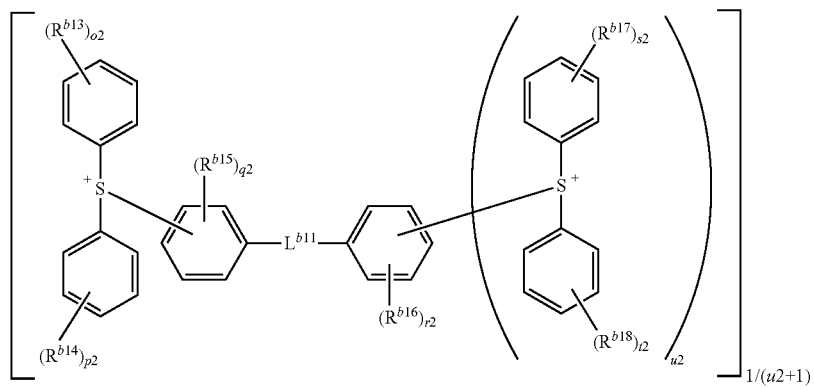

(b2-4)

wherein $R^{b4}$, $R^{b5}$ and $R^{b6}$ independently represent a C1-C30 alkyl group which can have one or more substituents selected from the group consisting of a hydroxyl group, a C1-C12 alkoxy group, a C6-C18 aromatic hydrocarbon group, a C3-C18 alicyclic hydrocarbon group which can have one or more substituents selected from the group consisting of a halogen atom, a C2-C4 acyl group and a glycidyloxy group, and a C6-C18 aromatic hydrocarbon group which can have one or more substituents selected from the group consisting of a halogen atom, a hydroxyl group, C1-C18 alicyclic hydrocarbon group, or C1-C12 alkoxy group, and $R^{b4}$ and $R^{b5}$, $R^{b4}$ and $R^{b6}$, or $R^{b5}$ and $R^{b6}$ can be bonded each other to form a ring containing $S^+$, $R^{b7}$ and $R^{b8}$ are independently in each occurrence a hydroxyl group, a C1-C12 alkyl group or a C1-C12 alkoxy group, m2 and n2 independently represents an integer of 0 to 5, $R^{b9}$ and $R^{10}$ independently represent a C1-C18 alkyl group or a C3-C18 alicyclic hydrocarbon group, or $R^{b9}$ and $R^{b10}$ are bonded each other to form a C1-C10 divalent acyclic hydrocarbon group which forms a 3- to 12-membered ring, preferably 3- to 7-membered ring together with the adjacent —$S^+$—, and one or more —$CH_2$— in the divalent acyclic hydrocarbon group may be replaced by an oxygen atom, sulfur atom or carbonyl atom, and $R^{b11}$ represents a hydrogen atom, a C1-C18 alkyl group, or a C3-C18 alicyclic hydrocarbon group, and $R^{b12}$ represents a C1-C12 alkyl group, a C3-C18 alicyclic hydrocarbon group, a C6-C18 aromatic hydrocarbon group, or $R^{b11}$ and $R^{b12}$ are bonded each other to form a C1-C10 divalent acyclic hydrocarbon group which forms a 2-oxocycloalkyl group together with the adjacent —CHCO—, and one or more —$CH_2$— in the divalent acyclic hydrocarbon group may be replaced by an oxygen atom, sulfur atom or carbonyl atom, and $R^{b13}$, $R^{b14}$, $R^{b15}$, $R^{b16}$, $R^{b17}$ and $R^{b18}$ independently represent a hydroxyl group, a C1-C12 alkyl group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

Preferable examples of the alkyl group represented by $R^{b4}$ to $R^{b6}$ include a methyl group, an ethyl group, a propyl group, an isopropyl group, a butyl group, a sec-butyl group, a tert-butyl group, a pentyl group, a hexyl group, an octyl group, a decyl group, a dodecyl group, a hexadecyl group, a pentadecyl group, a heptadecyl group and an octadecyl group, and more preferable examples thereof include a methyl group, an ethyl group, a propyl group and a butyl group. Preferable examples of the alicyclic hydrocarbon group represented by $R^{b4}$ to $R^{b6}$ include a cyclopropyl group, a cyclobutyl group, a cyclopentyl group, a cyclohexyl group, a cycloheptyl group, a cyclodecyl group, an adamantyl group, a 2-alkyladamantyl-2-yl group, a 1-(adaman-2-yl)alkane-1-yl group and an isobornyl group, and more preferable examples thereof include a cyclopentyl group and a cyclohexyl group.

Preferable examples of the aromatic group include a phenyl group, represented by $R^{b4}$ to $R^{b6}$, a naphthyl group and an anthryl group, and a phenyl group is more preferable. Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group. Examples of the halogen atom include a fluorine atom, a chlorine atom, a bromine atom and an iodine atom. Examples of the C2-C4 acyl group include an acetyl group, a propyonyl group and a butyryl group.

The ring containing $S^+$ formed by bonding $R^{b4}$ and $R^{b5}$, $R^{b4}$ and $R^{b6}$, or $R^{b5}$ and $R^{b6}$ each other may be a monocyclic ring, a polycyclic ring, an aromatic ring, a non-aromatic ring, a saturated ring or a unsaturated ring. The ring can contain one or more sulfur atom or oxygen atom in addition to $S^+$. The ring preferably has 3 to 18 carbon atoms, and more preferably has 4 to 13 carbon atoms.

Preferable examples of the alkyl group represented by $R^{b7}$ and $R^{b8}$ include a methyl group, an ethyl group, a propyl group, an isopropyl group, a butyl group, a sec-butyl group, a tert-butyl group, a pentyl group, a hexyl group, an octyl group and a 2-ethylhexyl group. Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Preferable examples of the alkyl group represented by $R^{b9}$ to $R^{b12}$ include a methyl group, an ethyl group, a propyl group, an isopropyl group, a butyl group, a sec-butyl group, a tort-butyl group, a pentyl group, a hexyl group, an octyl group and a 2-ethylhexyl group. Such alkyl group preferably has 1 to 12 carbon atoms. Preferable examples of the alicyclic hydrocarbon group represented by $R^{b9}$ to $R^{b11}$ include a cyclopropyl group, a cyclobutyl group, a cyclopentyl group, a cyclohexyl group, a cycloheptyl group, a cyclodecyl group, a 2-alkyl-2-adamantyl group, a 1-(1-adamantyl)-1-alkyl group and an isobornyl group.

The alicyclic hydrocarbon group represented by $R^{b9}$ to $R^{b11}$ has preferably 4 to 12 carbon atoms.

Preferable examples of the aromatic group represented by $R^{b12}$ include a phenyl group, 4-methyl phenyl group, 4-ethyl phenyl group, 4-tert butyl phenyl group, 4-cyclohexyl phenyl group, 4-methoxy phenyl group, biphenyl group and a naphthyl group, and a phenyl group is more preferable.

Preferable examples of the group in which the alkyl group has been combined with the aromatic hydrocarbon group represented by $R^{b12}$ include an aralkyl group such as benzyl group.

Preferable examples of the alkylcarbonyloxy group represented by $R^{b12}$ include a group consisting of an acyl group and an oxygen atom.

Examples of the C3-C12 divalent acyclic hydrocarbon group formed by bonding $R^{b9}$ and $R^{10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include oxocyclopentane ring, oxocyclohexane ring, oxonorbonane ring and oxoamadantane ring. A C1-C5 divalent acyclic hydrocarbon group is preferable.

Examples of the group in which the alkyl group has been combined with the aromatic hydrocarbon group include typically an aralkyl group, preferably benzyl group. As examples of the organic cations represented by formulae (b2-1) to (b2-4) includes organic cations mentioned in JP2010-204646A1.

Among the above-mentioned cations, preferred is the cation represented by the formula (b2-1) or the formula (b2-2), more preferred is the cation represented by the formula (b2-1), still more preferred is the cation represented by the formula (b2-1) in which any of $R^{b4}$, $R^{b5}$ and $R^{b6}$ is an aromatic hydrocarbon group, and particularly more preferred is the cation represented by the formula (b2-1-1).

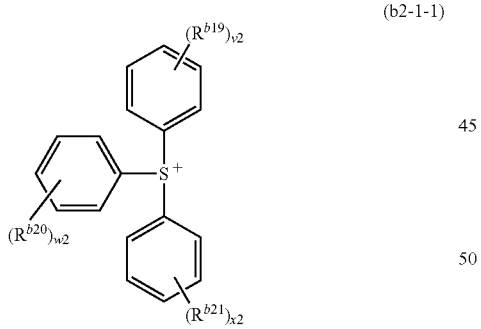

(b2-1-1)

wherein $R^{b19}$, $R^{b20}$ and $R^{b21}$ are independently in each occurrence a halogen atom (preferably a fluorine atom), a hydroxyl group, a C1-C18 alkyl group, a C3-C18 saturated cyclic hydrocarbon group or a C1-C12 alkoxy group, and one or more hydrogen atoms of the alkyl group can be replaced by a hydroxyl group, a C1-C12 alkoxyl group, or a C6-C18 aromatic group, one or more hydrogen atoms of the saturated cyclic hydrocarbon group can be replaced by a halogen group, a C2-C4 acyl group, or a C grycidyloxy group, and $R^{b19}$ and $R^{b20}$, $R^{b19}$ and $R^{b21}$ or $R^{b20}$ and $R^{b21}$ can be bonded each other to form a ring together with $S^+$ and v2, w2 and x2 independently each represent an integer of 0 to 5.

The alkyl group has preferably 1 to 12 carbon atoms, more preferably C1-12 alkyl group, and the saturated cyclic hydrocarbon group has preferably 4 to 18 carbon atoms. Each of $R^{b19}$, $R^{b20}$ and $R^{b21}$ preferably a halogen atom (preferably a fluorine atom), a hydroxyl, group, a C1-C12 alkyl group and a C1-C12 alkoxy group.

The v2, w2 and x2 independently each preferably represent 0 or 1.

It is more preferred that $R^{b19}$, $R^{b20}$ and $R^{b21}$ are independently in each occurrence a halogen atom, specifically a fluorine atom, a hydroxyl group, a C1-C12 alkyl group or a C1-C12 alkoxy group, and v2, w2 and x2 independently each represent 0 or 1.

As the cation represented by the formula (b2-1-1), a triphenylsulfonium cation and a tritlylsulfonium cation are especially preferable.

Examples of the cation represented by the formula (b2-1-1) include the following.

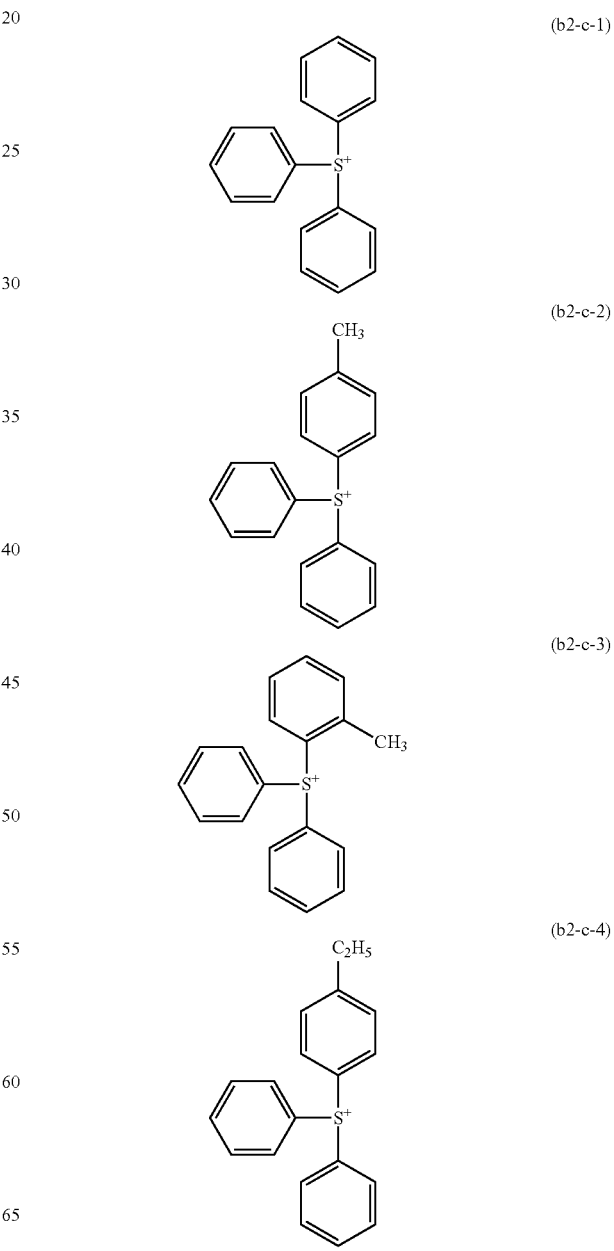

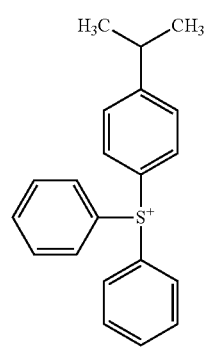
(b2-c-5)
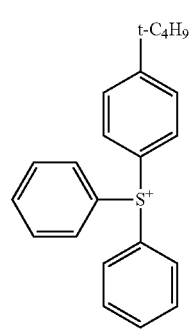
(b2-c-6)
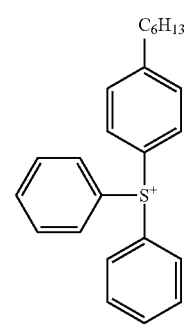
(b2-c-7)
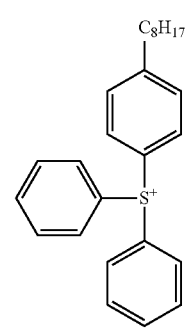
(b2-c-8)
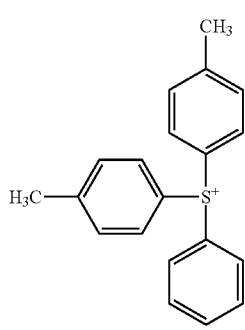
(b2-c-9)
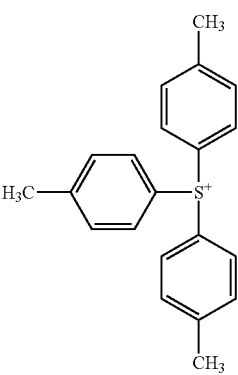
(b2-c-10)
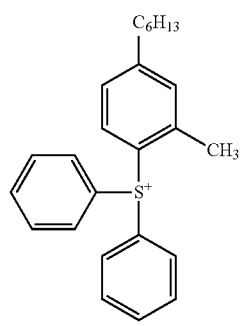
(b2-c-11)
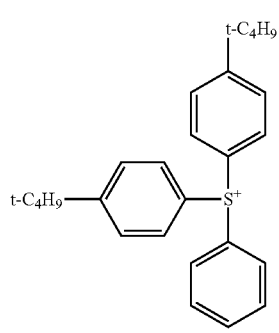
(b2-c-12)
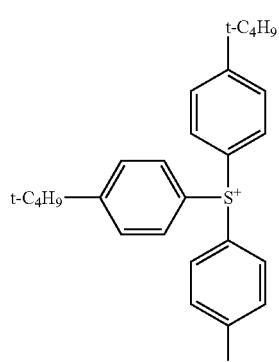
(b2-c-13)
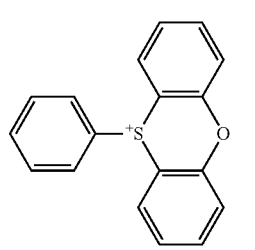
(b2-c-14)

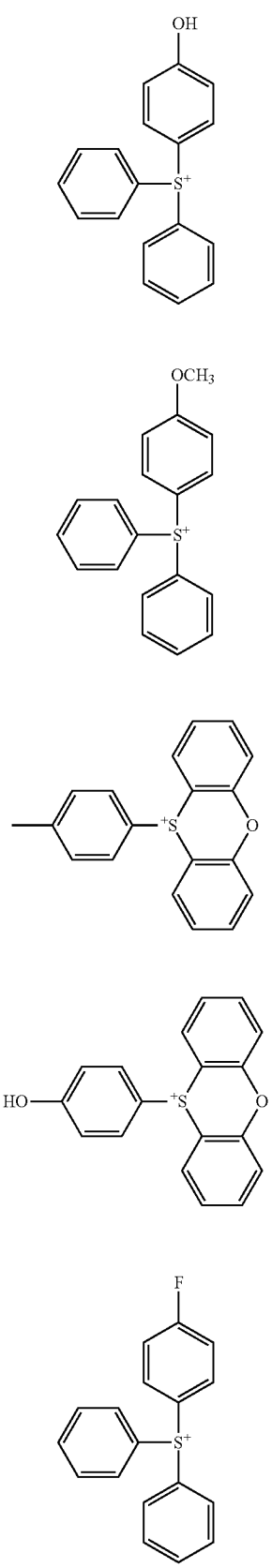
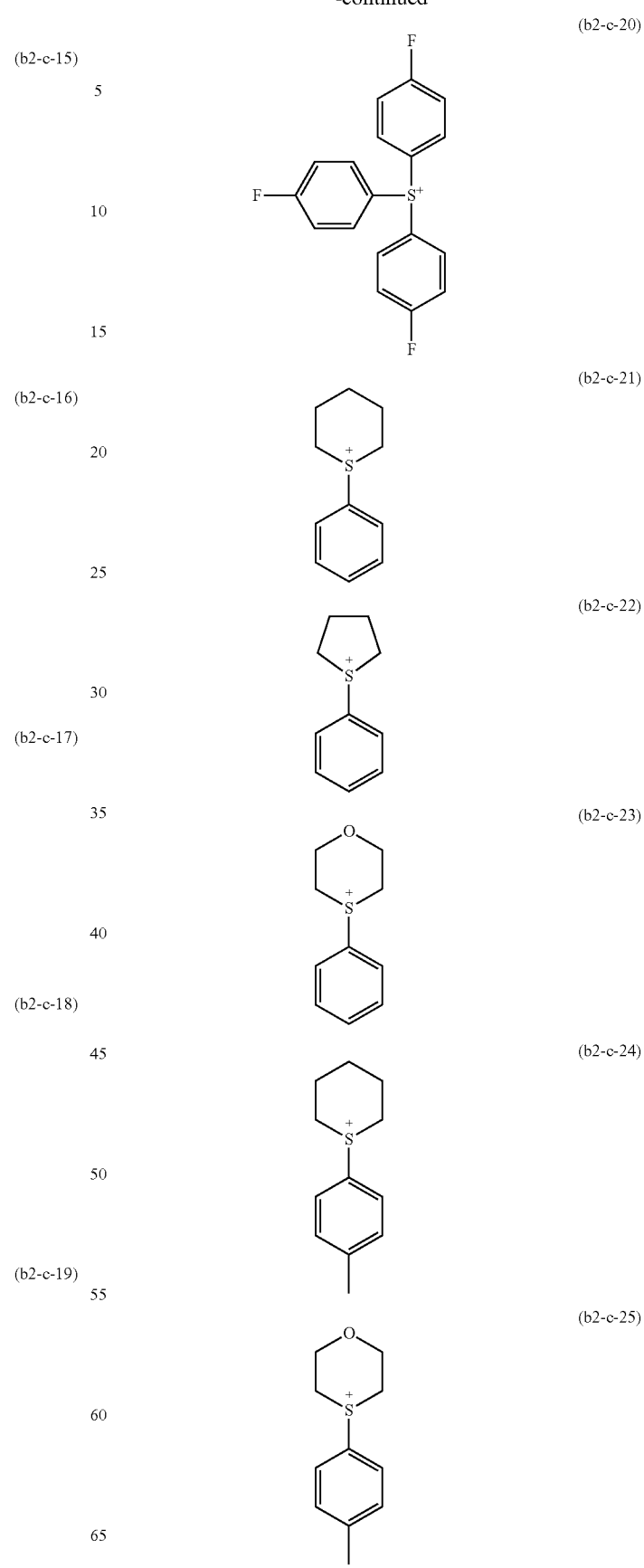

-continued
(b2-c-26)
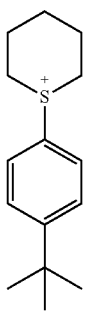
(b2-c-27)
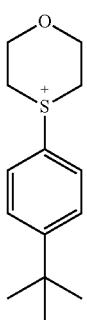
Examples of the cation represented by the formula (b2-2) include the followings.
(b2-c-28)
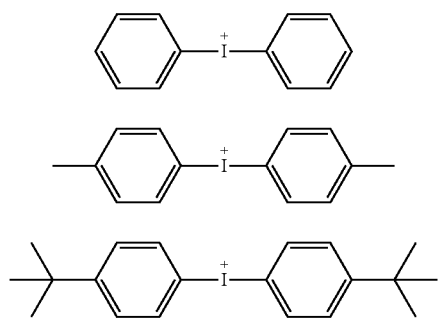
(b2-c-29)
(b2-c-30)
Examples of the cation represented by the formula (b2-3) include the followings.
(b2-c-31)
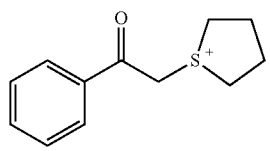
(b2-c-32)
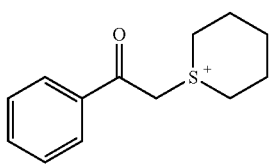
-continued
(b2-c-33)
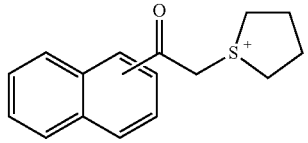
(b2-c-34)
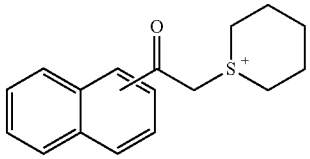
Examples of the cation represented by the formula (b2-4) include the followings.
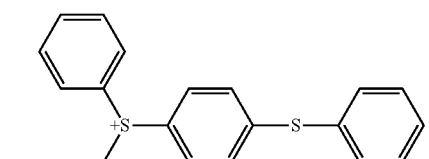
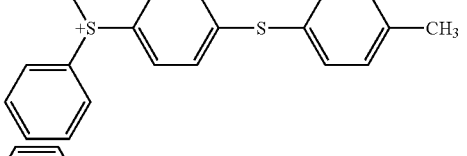
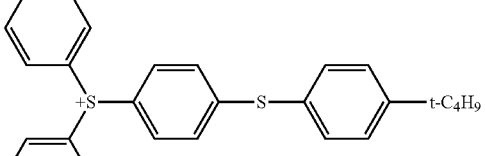
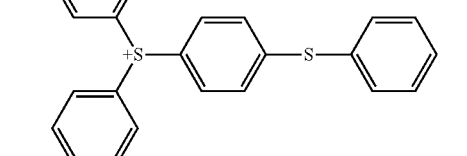
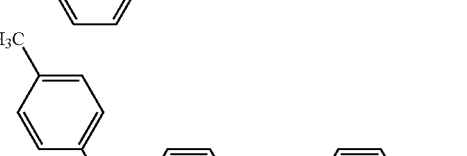
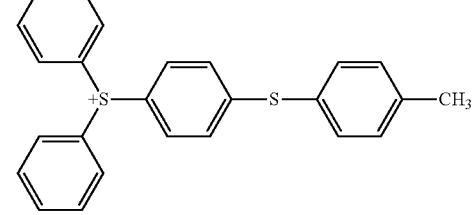

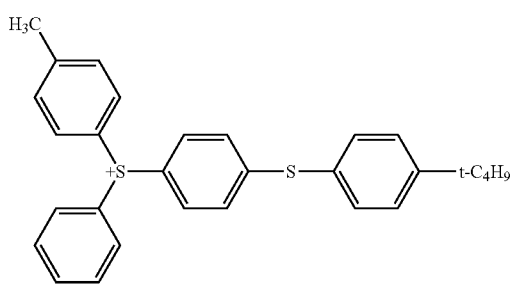
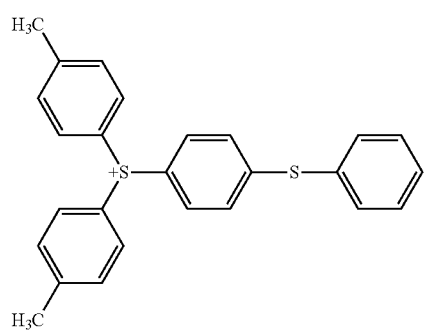
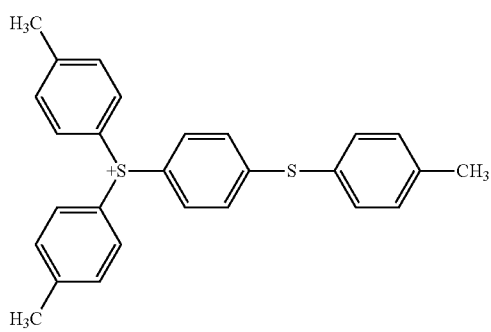
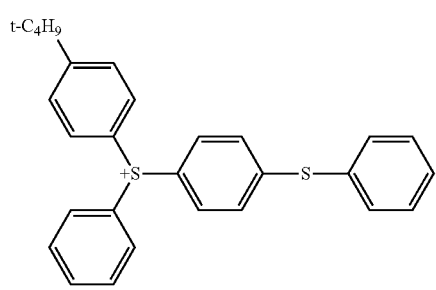
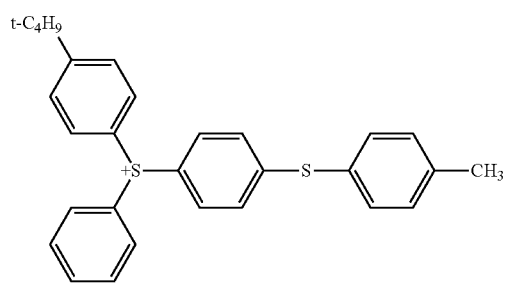
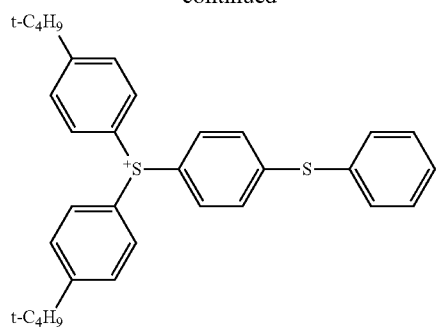
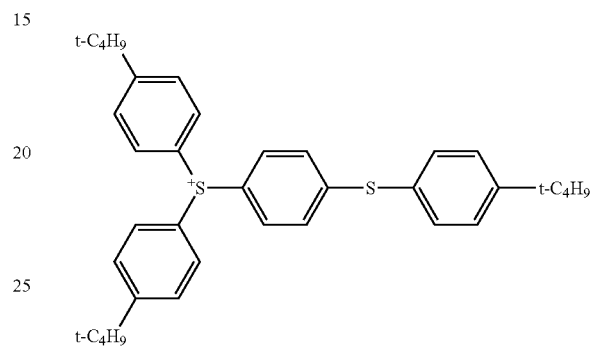
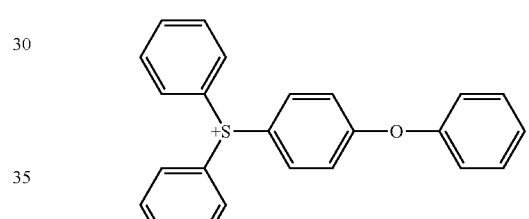
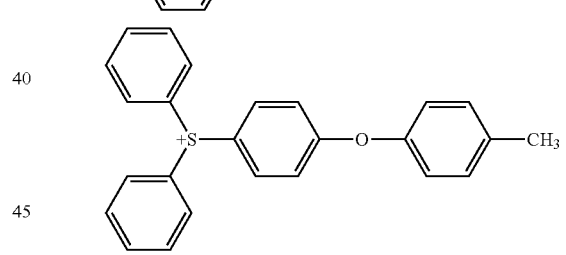
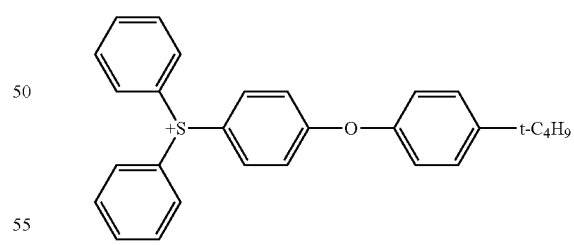
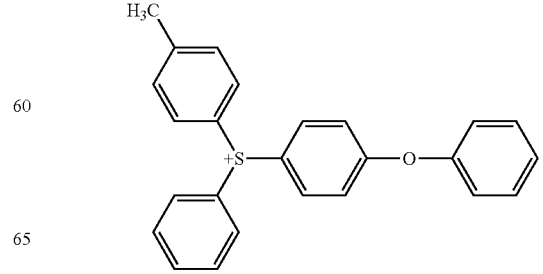

-continued
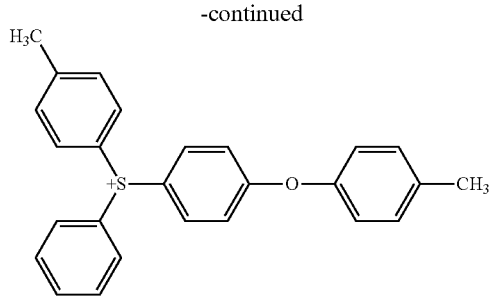
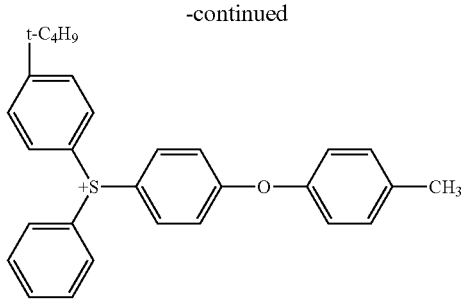
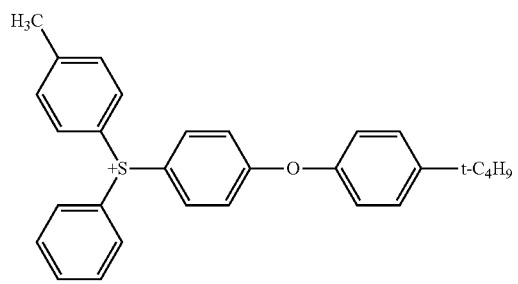
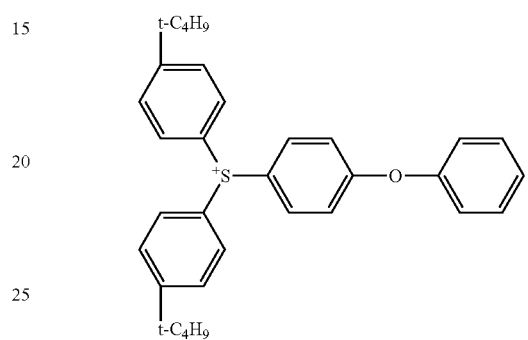
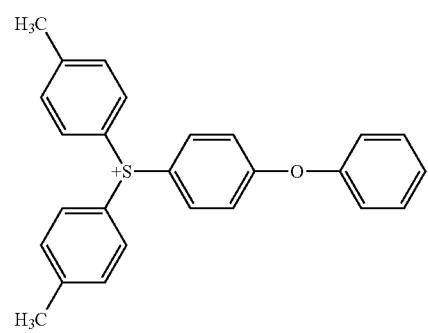
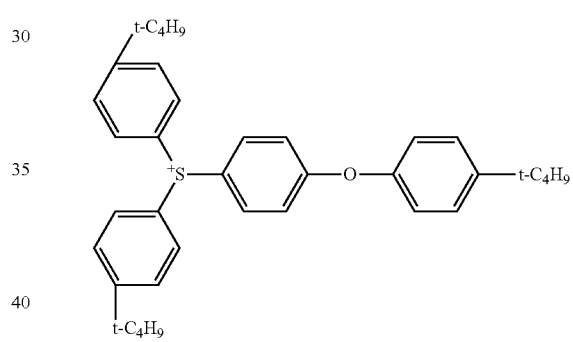
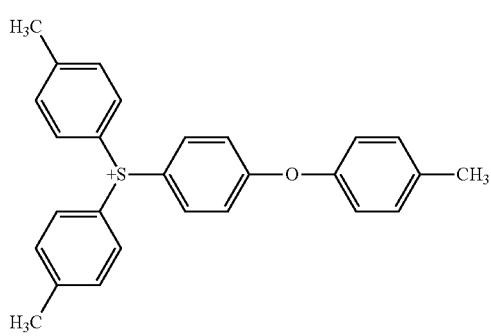
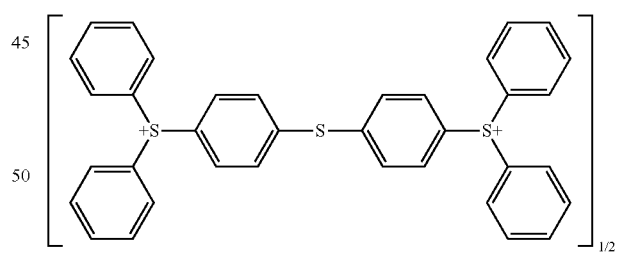
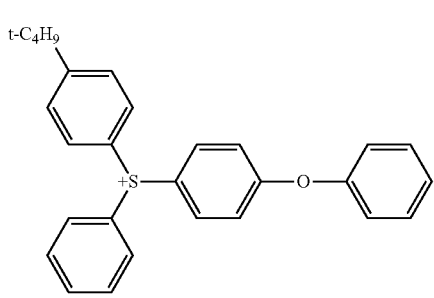
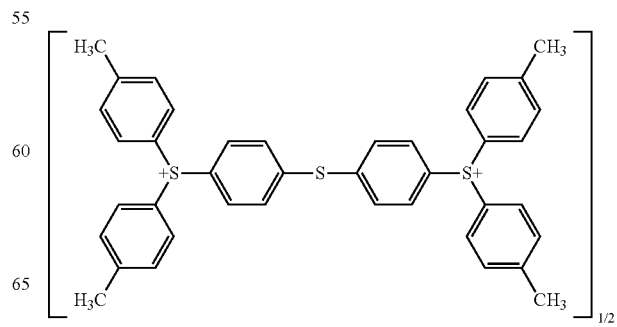

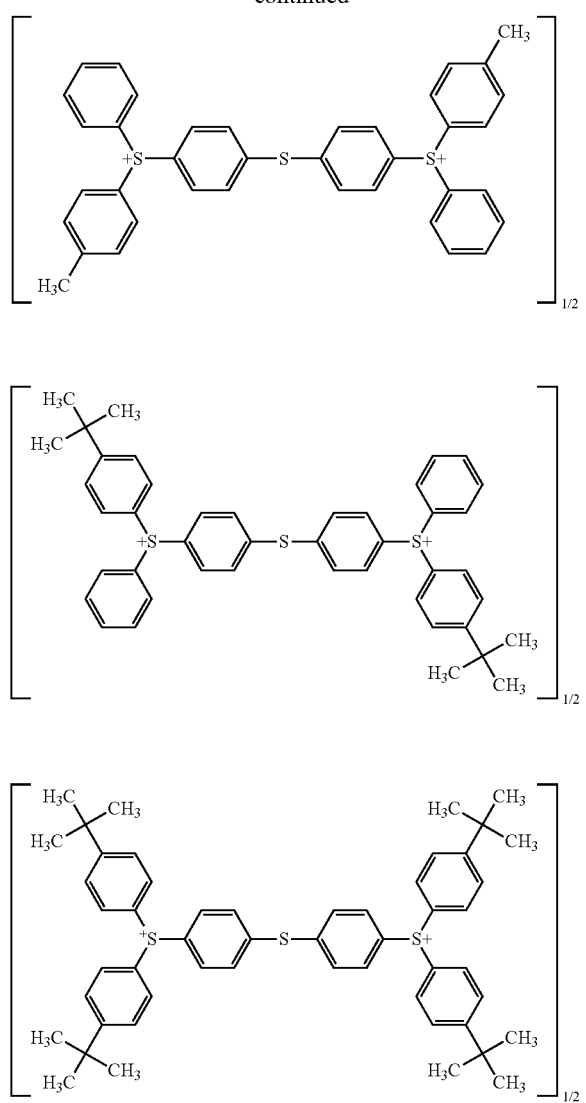

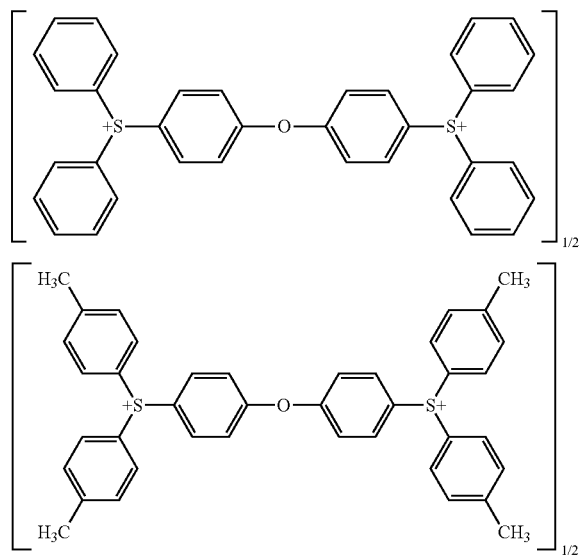

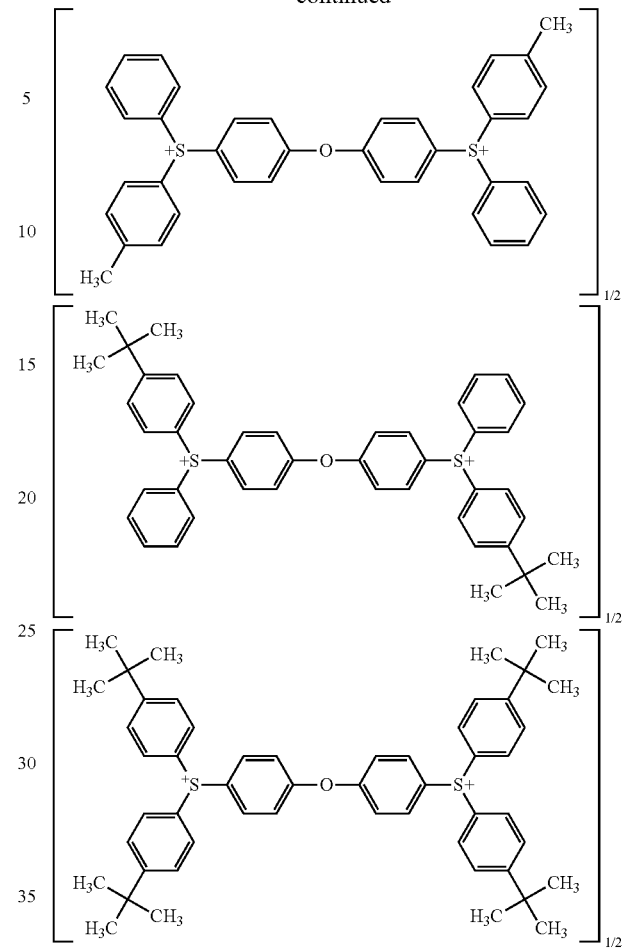

Examples of SALT (I) include a salt wherein the anion is any one of the above-mentioned anions and the counter ion is any one of organic counter ions. Preferable examples of SALT (I) include those shown in Tables 1, 2, 3, 4 and 5.

In each tables, any symbol of column "sulfonic acid" refers to the symbol of formula representing the sulfonic acid, any symbol of column "organic counter ion" refers to the symbol of formula representing the counter ion, and any symbol of column "SALT (I)" refers to the symbol of formula representing the SALT (I).

TABLE 1

| SALT (I) | Sulfonic acid | organic counter ion |
|---|---|---|
| (I-1) | (Ia1-1-1) | (b2-c-1) |
| (I-2) | (Ia1-1-2) | (b2-c-1) |
| (I-3) | (Ia1-1-3) | (b2-c-1) |
| (I-4) | (Ia1-1-7) | (b2-c-1) |
| (I-5) | (Ia1-1-10) | (b2-c-1) |
| (I-6) | (Ia1-1-12) | (b2-c-1) |
| (I-7) | (Ia1-1-1) | (b2-c-10) |
| (I-8) | (Ia1-1-2) | (b2-c-10) |
| (I-9) | (Ia1-1-3) | (b2-c-10) |
| (I-10) | (Ia1-1-7) | (b2-c-10) |
| (I-11) | (Ia1-1-10) | (b2-c-10) |
| (I-12) | (Ia1-1-12) | (b2-c-10) |
| (I-13) | (Ia1-1-1) | (b2-c-28) |
| (I-14) | (Ia1-1-2) | (b2-c-28) |
| (I-15) | (Ia1-1-3) | (b2-c-28) |
| (I-16) | (Ia1-1-7) | (b2-c-28) |

TABLE 1-continued

| SALT (I) | Sulfonic acid | organic counter ion |
|---|---|---|
| (I-17) | (Ia1-1-10) | (b2-c-28) |
| (I-18) | (Ia1-1-12) | (b2-c-28) |
| (I-19) | (Ia1-1-1) | (b2-c-31) |
| (I-20) | (Ia1-1-2) | (b2-c-31) |
| (I-21) | (Ia1-1-3) | (b2-c-31) |
| (I-22) | (Ia1-1-7) | (b2-c-31) |
| (I-23) | (Ia1-1-10) | (b2-c-31) |
| (I-24) | (Ia1-1-12) | (b2-c-31) |
| (I-25) | (Ia1-1-1) | (b2-c-2) |
| (I-26) | (Ia1-1-2) | (b2-c-2) |
| (I-27) | (Ia1-1-3) | (b2-c-2) |
| (I-28) | (Ia1-1-7) | (b2-c-2) |
| (I-29) | (Ia1-1-10) | (b2-c-2) |
| (I-30) | (Ia1-1-12) | (b2-c-2) |
| (I-31) | (Ia1-1-1) | (b2-c-23) |
| (I-32) | (Ia1-1-2) | (b2-c-23) |
| (I-33) | (Ia1-1-3) | (b2-c-23) |
| (I-34) | (Ia1-1-7) | (b2-c-23) |
| (I-35) | (Ia1-1-10) | (b2-c-23) |
| (I-36) | (Ia1-1-12) | (b2-c-23) |

TABLE 2

| SALT (I) | Sulfonic acid | organic counter ion |
|---|---|---|
| (I-37) | (Ia1-1-1) | (b2-c-30) |
| (I-38) | (Ia1-1-2) | (b2-c-30) |
| (I-39) | (Ia1-1-3) | (b2-c-30) |
| (I-40) | (Ia1-1-7) | (b2-c-30) |
| (I-41) | (Ia1-1-10) | (b2-c-30) |
| (I-42) | (Ia1-1-12) | (b2-c-30) |
| (I-43) | (Ia1-1-1) | (b2-c-33) |
| (I-44) | (Ia1-1-2) | (b2-c-33) |
| (I-45) | (Ia1-1-3) | (b2-c-33) |
| (I-46) | (Ia1-1-7) | (b2-c-33) |
| (I-47) | (Ia1-1-10) | (b2-c-33) |
| (I-48) | (Ia1-1-12) | (b2-c-33) |
| (I-49) | (Ia1-1-1) | (b2-c-6) |
| (I-50) | (Ia1-1-2) | (b2-c-6) |
| (I-51) | (Ia1-1-3) | (b2-c-6) |
| (I-52) | (Ia1-1-7) | (b2-c-6) |
| (I-53) | (Ia1-1-10) | (b2-c-6) |
| (I-54) | (Ia1-1-12) | (b2-c-6) |
| (I-55) | (Ia1-1-1) | (b2-c-15) |
| (I-56) | (Ia1-1-2) | (b2-c-15) |
| (I-57) | (Ia1-1-3) | (b2-c-15) |
| (I-58) | (Ia1-1-7) | (b2-c-15) |
| (I-59) | (Ia1-1-10) | (b2-c-15) |
| (I-60) | (Ia1-1-12) | (b2-c-15) |

TABLE 3

| SALT (I) | Sulfonic acid | organic counter ion |
|---|---|---|
| (I-61) | (Ia1-1-13) | (b2-c-1) |
| (I-62) | (Ia1-1-14) | (b2-c-1) |
| (I-63) | (Ia1-1-15) | (b2-c-1) |
| (I-64) | (Ia1-1-13) | (b2-c-10) |
| (I-65) | (Ia1-1-14) | (b2-c-10) |
| (I-66) | (Ia1-1-15) | (b2-c-10) |
| (I-67) | (Ia1-1-13) | (b2-c-28) |
| (I-68) | (Ia1-1-14) | (b2-c-28) |
| (I-69) | (Ia1-1-15) | (b2-c-28) |
| (I-70) | (Ia1-1-13) | (b2-c-31) |
| (I-71) | (Ia1-1-14) | (b2-c-31) |
| (I-72) | (Ia1-1-15) | (b2-c-31) |
| (I-73) | (Ia1-1-13) | (b2-c-2) |
| (I-74) | (Ia1-1-14) | (b2-c-2) |
| (I-75) | (Ia1-1-15) | (b2-c-2) |
| (I-76) | (Ia1-1-13) | (b2-c-23) |
| (I-77) | (Ia1-1-14) | (b2-c-23) |
| (I-78) | (Ia1-1-15) | (b2-c-23) |
| (I-79) | (Ia1-1-13) | (b2-c-30) |

TABLE 3-continued

| SALT (I) | Sulfonic acid | organic counter ion |
|---|---|---|
| (I-80) | (Ia1-1-14) | (b2-c-30) |
| (I-81) | (Ia1-1-15) | (b2-c-30) |
| (I-82) | (Ia1-1-13) | (b2-c-33) |
| (I-83) | (Ia1-1-14) | (b2-c-33) |
| (I-84) | (Ia1-1-15) | (b2-c-33) |
| (I-85) | (Ia1-1-13) | (b2-c-6) |
| (I-86) | (Ia1-1-14) | (b2-c-6) |
| (I-87) | (Ia1-1-15) | (b2-c-6) |
| (I-88) | (Ia1-1-13) | (b2-c-15) |
| (I-89) | (Ia1-1-14) | (b2-c-15) |
| (I-90) | (Ia1-1-15) | (b2-c-15) |

TABLE 4

| SALT (I) | Sulfonic acid | organic counter ion |
|---|---|---|
| (I-91) | (Ia1-1-19) | (b2-c-1) |
| (I-92) | (Ia1-1-20) | (b2-c-1) |
| (I-93) | (Ia1-1-25) | (b2-c-1) |
| (I-94) | (Ia1-1-26) | (b2-c-1) |
| (I-95) | (Ia1-1-19) | (b2-c-10) |
| (I-96) | (Ia1-1-20) | (b2-c-10) |
| (I-97) | (Ia1-1-25) | (b2-c-10) |
| (I-98) | (Ia1-1-26) | (b2-c-10) |
| (I-99) | (Ia1-1-19) | (b2-c-28) |
| (I-100) | (Ia1-1-20) | (b2-c-28) |
| (I-101) | (Ia1-1-25) | (b2-c-28) |
| (I-102) | (Ia1-1-26) | (b2-c-28) |
| (I-103) | (Ia1-1-19) | (b2-c-31) |
| (I-104) | (Ia1-1-20) | (b2-c-31) |
| (I-105) | (Ia1-1-25) | (b2-c-31) |
| (I-106) | (Ia1-1-26) | (b2-c-31) |
| (I-107) | (Ia1-1-19) | (b2-c-2) |
| (I-108) | (Ia1-1-20) | (b2-c-2) |
| (I-109) | (Ia1-1-25) | (b2-c-2) |
| (I-110) | (Ia1-1-26) | (b2-c-2) |
| (I-111) | (Ia1-1-19) | (b2-c-23) |
| (I-112) | (Ia1-1-20) | (b2-c-23) |
| (I-113) | (Ia1-1-25) | (b2-c-23) |
| (I-114) | (Ia1-1-26) | (b2-c-23) |

TABLE 5

| SALT (I) | Sulfonic acid | organic counter ion |
|---|---|---|
| (I-115) | (Ia1-1-19) | (b2-c-30) |
| (I-116) | (Ia1-1-20) | (b2-c-30) |
| (I-117) | (Ia1-1-25) | (b2-c-30) |
| (I-118) | (Ia1-1-26) | (b2-c-30) |
| (I-119) | (Ia1-1-19) | (b2-c-33) |
| (I-120) | (Ia1-1-20) | (b2-c-33) |
| (I-121) | (Ia1-1-25) | (b2-c-33) |
| (I-122) | (Ia1-1-26) | (b2-c-33) |
| (I-123) | (Ia1-1-19) | (b2-c-6) |
| (I-124) | (Ia1-1-20) | (b2-c-6) |
| (I-125) | (Ia1-1-25) | (b2-c-6) |
| (I-126) | (Ia1-1-26) | (b2-c-6) |
| (I-127) | (Ia1-1-19) | (b2-c-15) |
| (I-128) | (Ia1-1-20) | (b2-c-15) |
| (I-129) | (Ia1-1-25) | (b2-c-15) |
| (I-130) | (Ia1-1-26) | (b2-c-15) |
| (I-131) | (Ia1-1-31) | (b2-c-1) |
| (I-132) | (Ia1-1-32) | (b2-c-1) |
| (I-133) | (Ia1-1-33) | (b2-c-1) |
| (I-134) | (Ia1-1-34) | (b2-c-1) |
| (I-135) | (Ia1-1-35) | (b2-c-1) |
| (I-136) | (Ia1-1-36) | (b2-c-1) |
| (I-137) | (Ia1-1-31) | (b2-c-10) |
| (I-138) | (Ia1-1-32) | (b2-c-10) |
| (I-139) | (Ia1-1-33) | (b2-c-10) |
| (I-140) | (Ia1-1-34) | (b2-c-10) |
| (I-141) | (Ia1-1-35) | (b2-c-10) |
| (I-142) | (Ia1-1-36) | (b2-c-10) |

TABLE 5-continued
| SALT (I) | Sulfonic acid | organic counter ion |
|---|---|---|
| (I-143) | (Ia1-1-31) | (b2-c-28) |
| (I-144) | (Ia1-1-32) | (b2-c-28) |
| (I-145) | (Ia1-1-33) | (b2-c-28) |
| (I-146) | (Ia1-1-34) | (b2-c-28) |
| (I-147) | (Ia1-1-35) | (b2-c-28) |
| (I-148) | (Ia1-1-36) | (b2-c-28) |
| (I-149) | (Ia1-1-31) | (b2-c-31) |
| (I-150) | (Ia1-1-32) | (b2-c-31) |
| (I-151) | (Ia1-1-33) | (b2-c-31) |
| (I-152) | (Ia1-1-34) | (b2-c-31) |
| (I-153) | (Ia1-1-35) | (b2-c-31) |
| (I-154) | (Ia1-1-36) | (b2-c-31) |
Preferred examples of SALT (I) include those represented as follow.
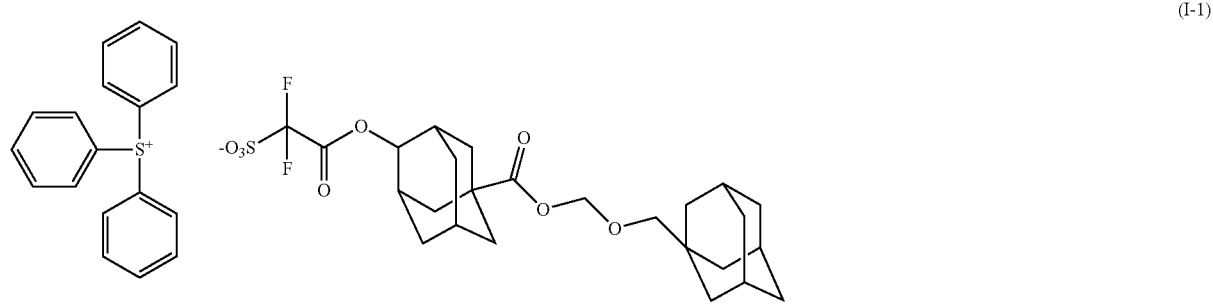
(I-1)
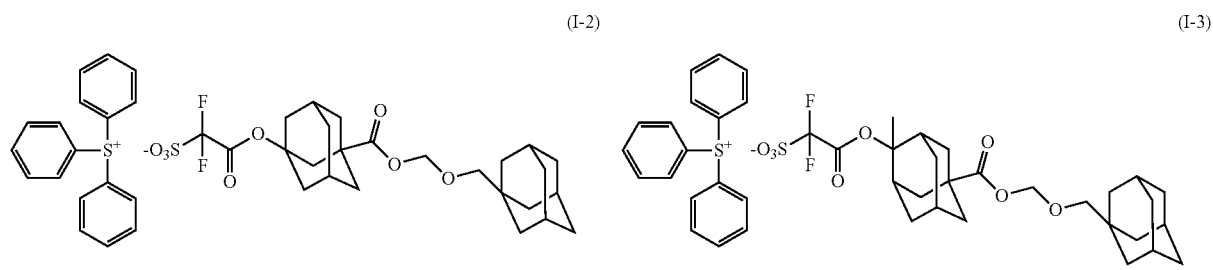
(I-2) (I-3)
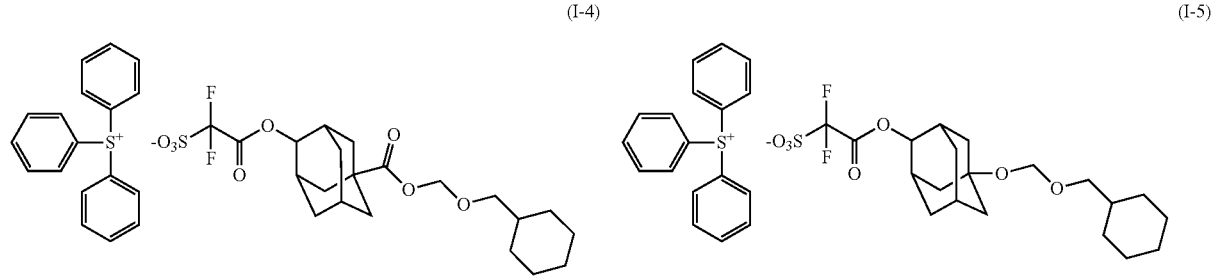
(I-4) (I-5)
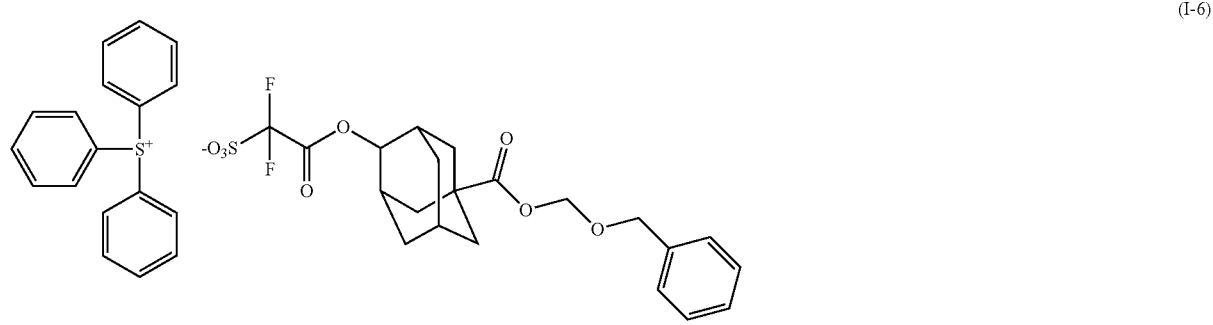
(I-6)

(I-61)
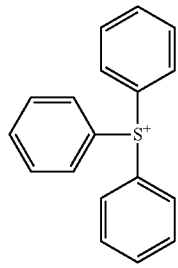 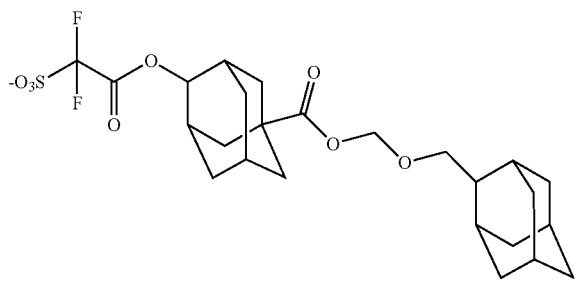
(I-62)
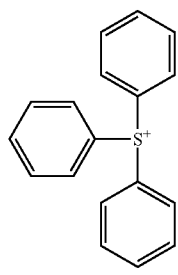 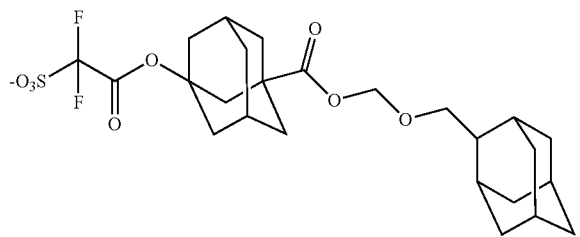
(I-63)
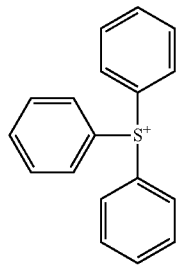 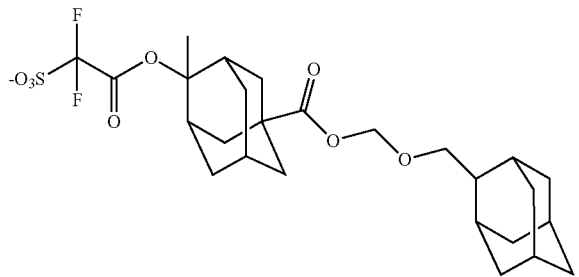
(I-91)
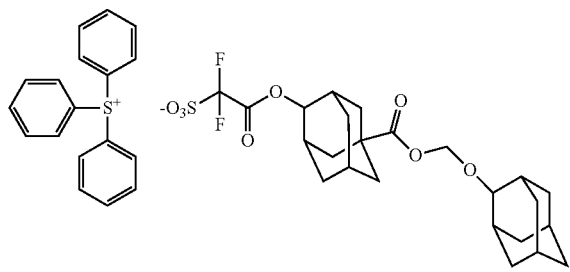
(I-92)
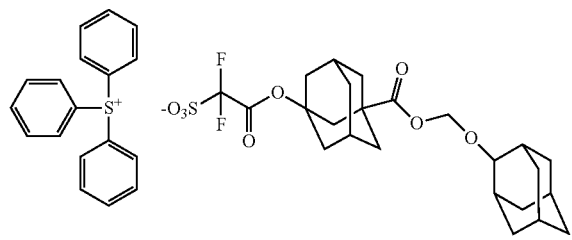
(I-93)
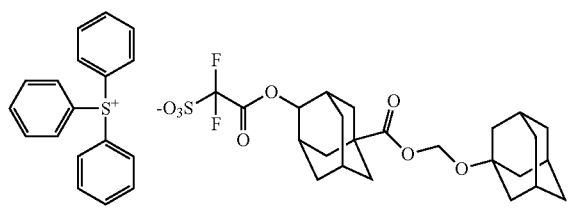
(I-94)
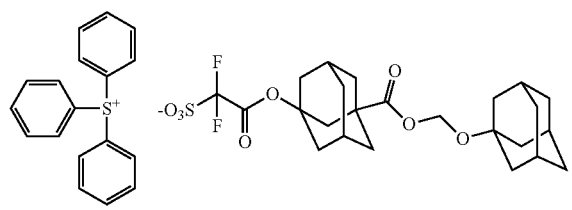

(I-131)
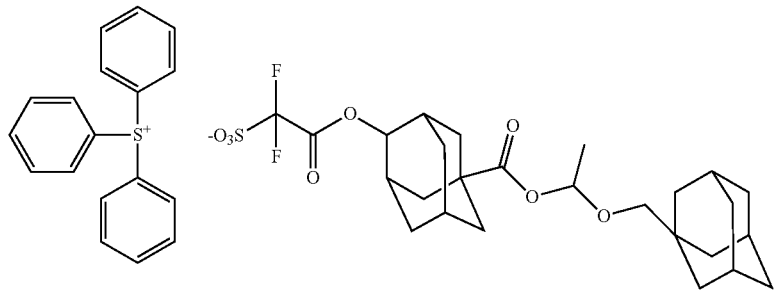
(I-132)
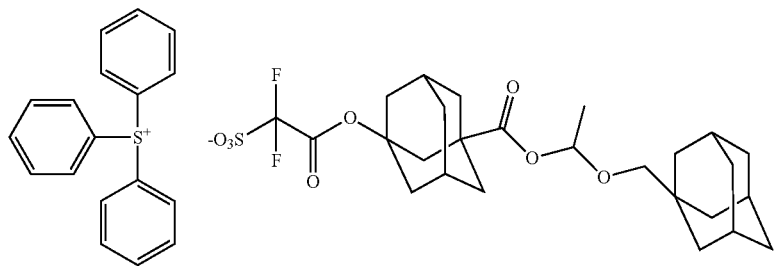
(I-7)
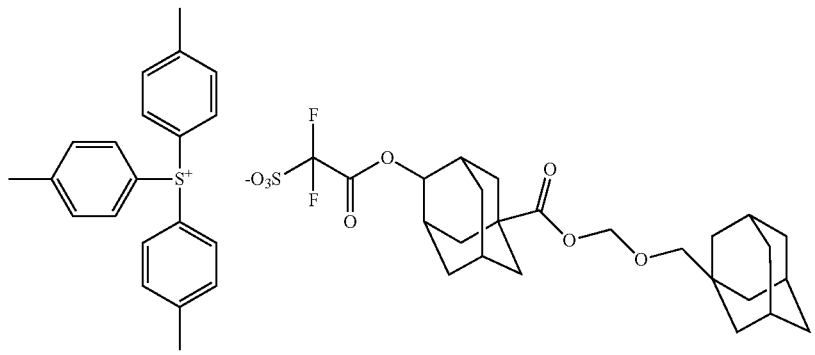
(I-8)
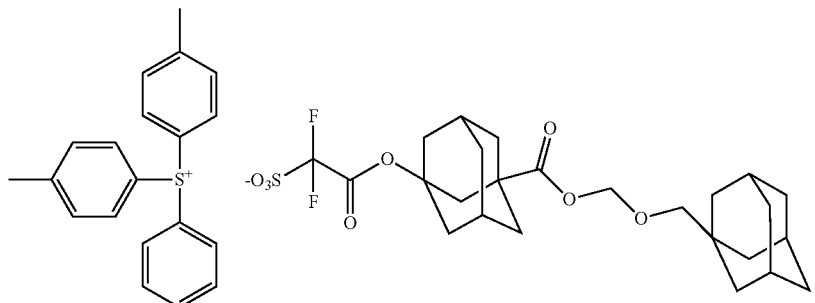
(I-9)
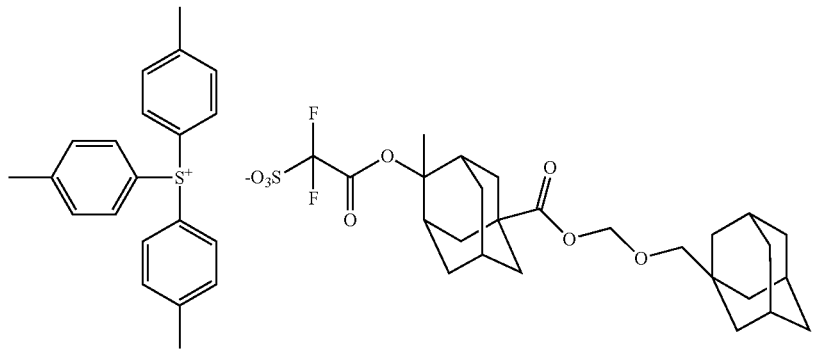

(I-10)
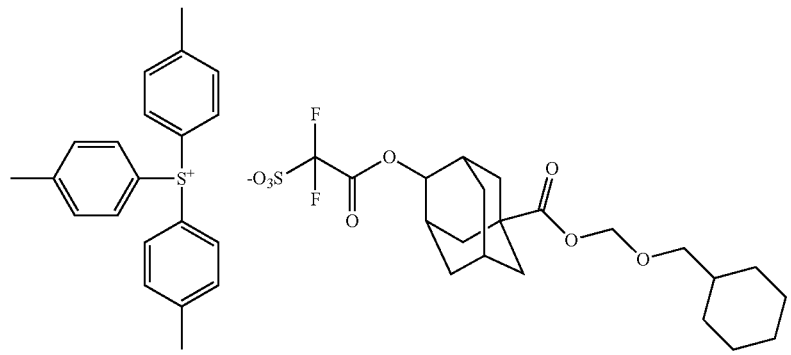
(I-11)
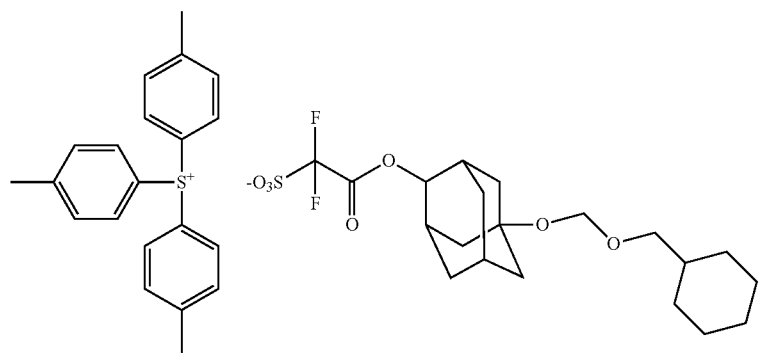
(I-12)
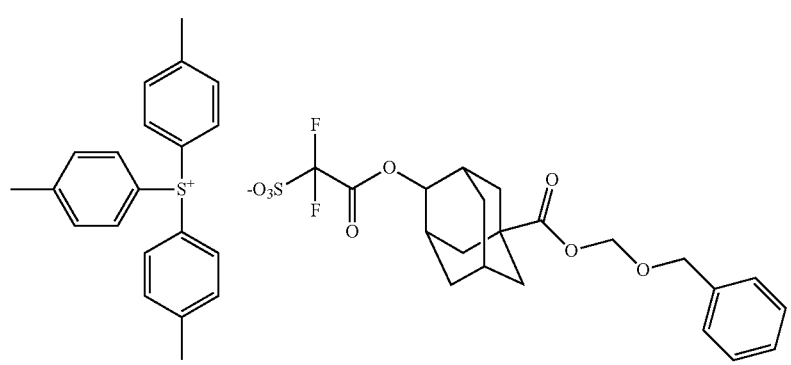
(I-64)
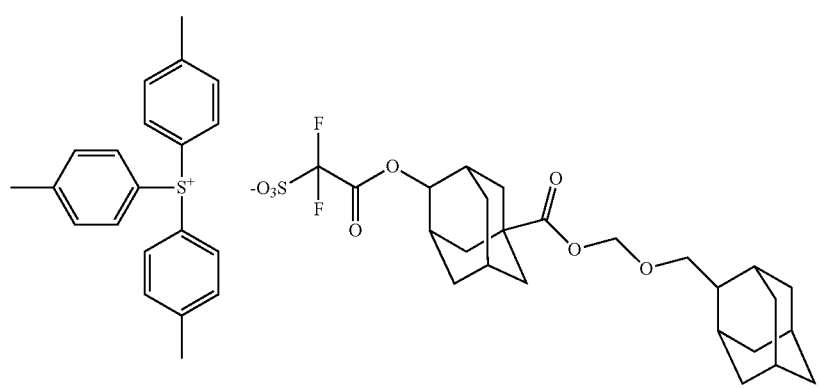

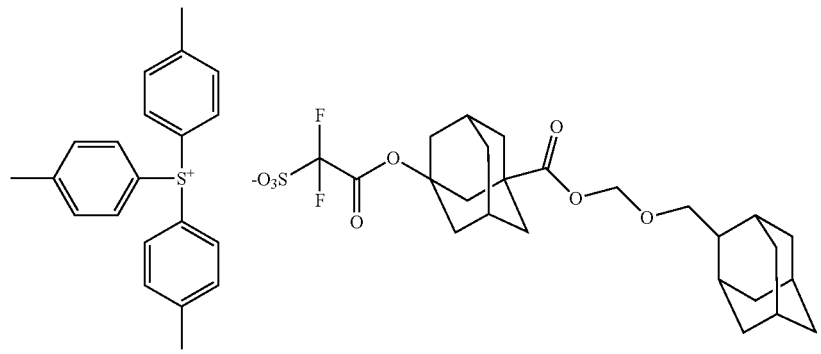
(I-65)
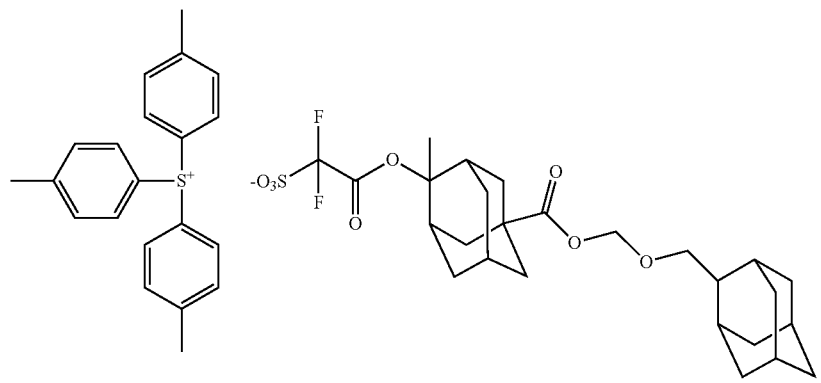
(I-66)
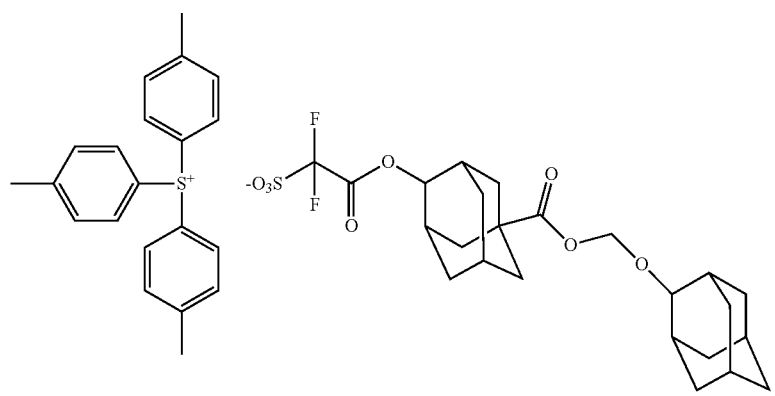
(I-95)
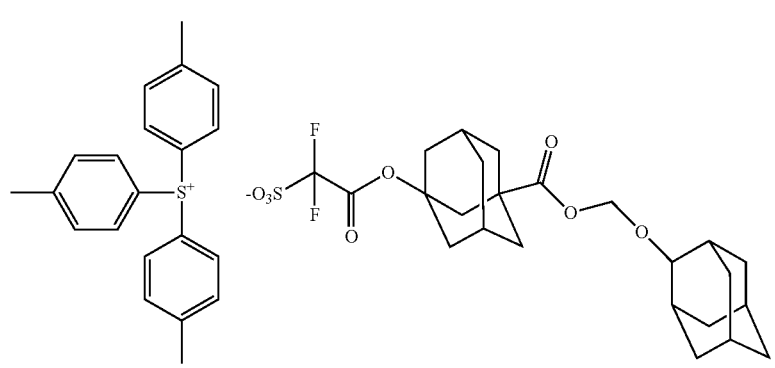
(I-96)

(I-97)
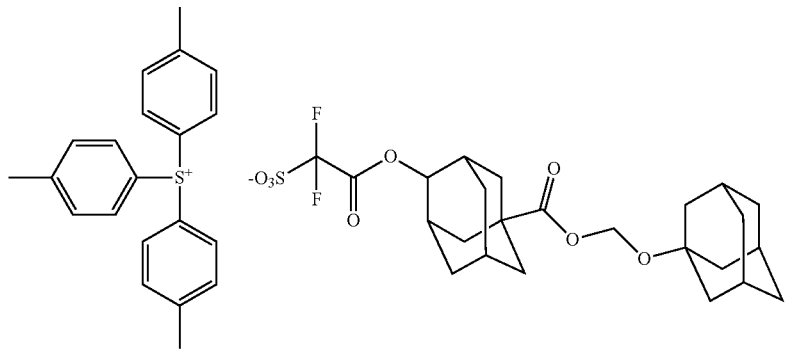
(I-98)
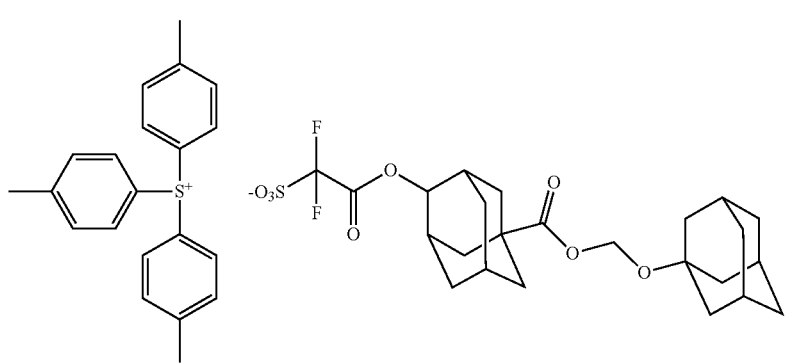
(I-137)
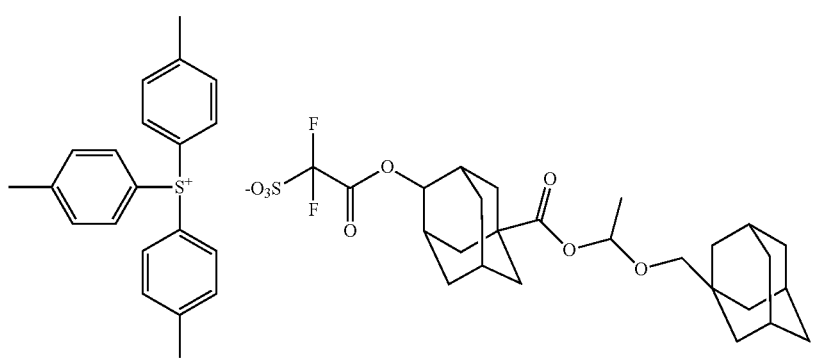
(I-138)
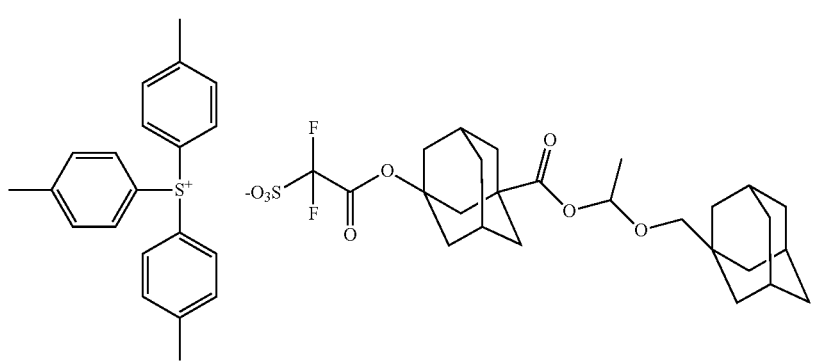

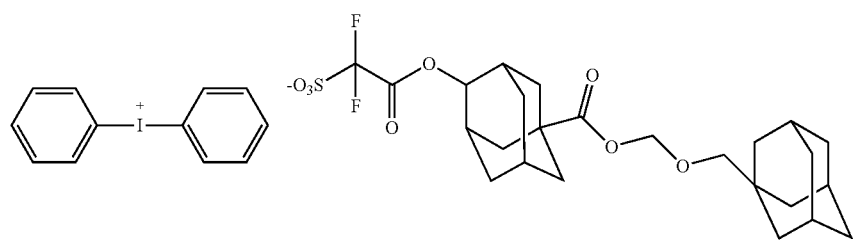
(I-13)
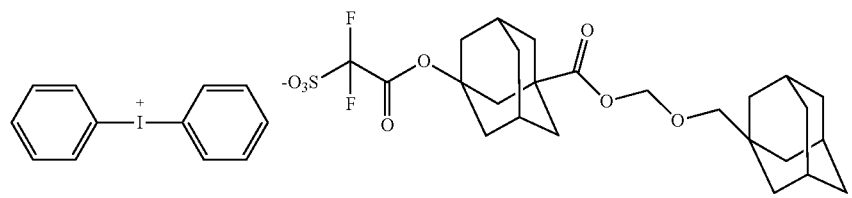
(I-14)
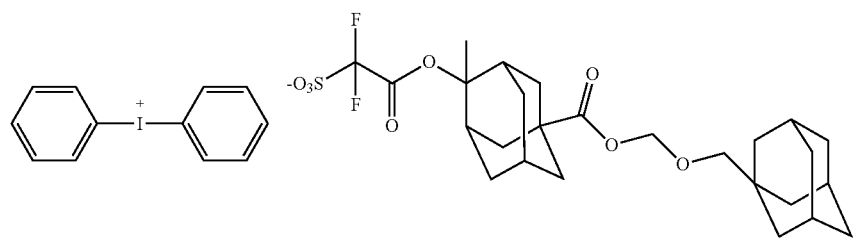
(I-15)
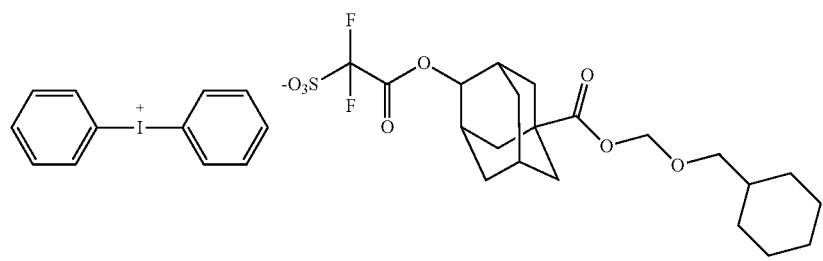
(I-16)
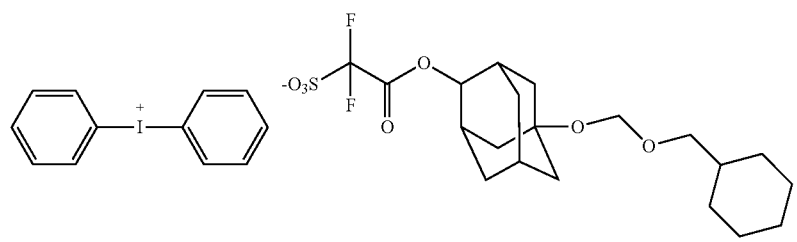
(I-17)
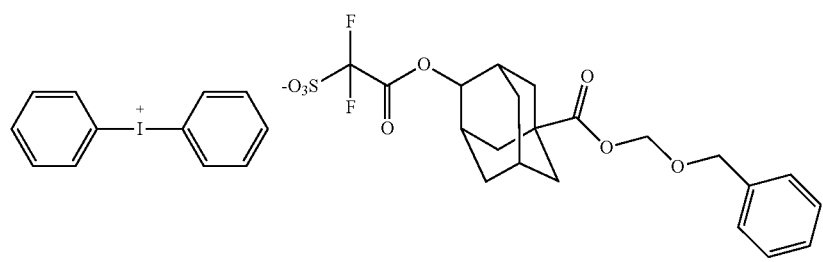
(I-18)

-continued
(I-67)
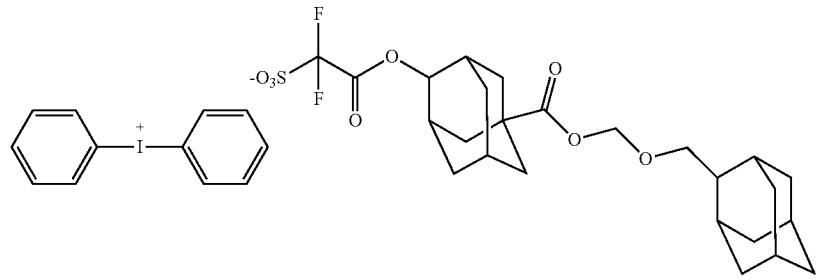
(I-68)
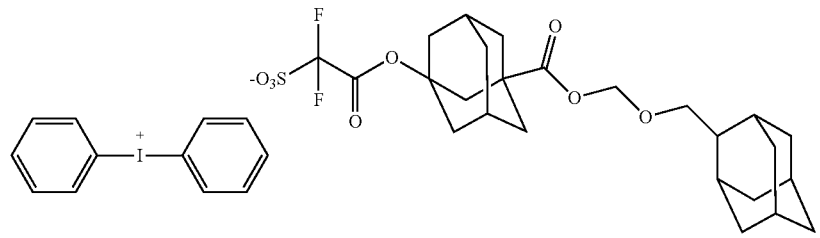
(I-69)
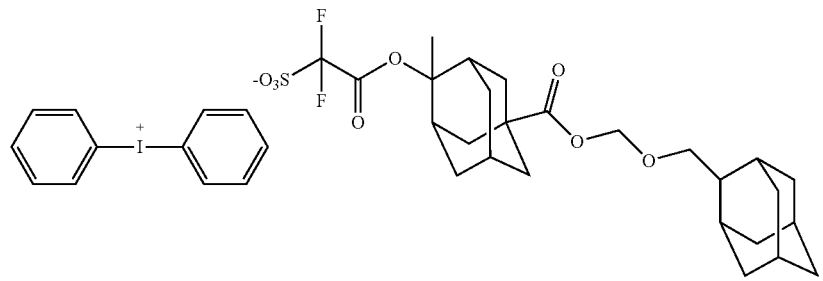
(I-99)
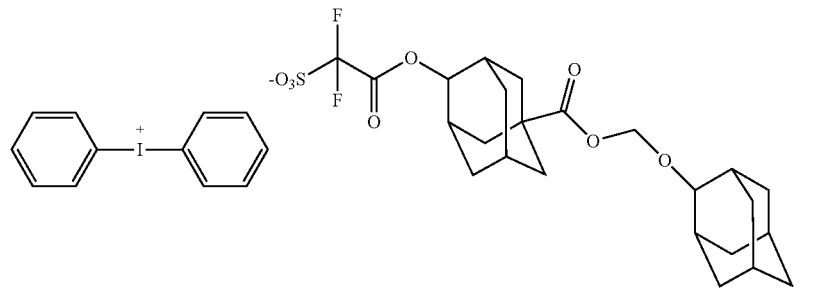
(I-100)
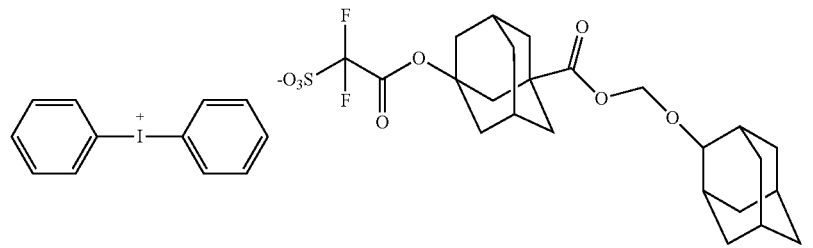
(I-101)
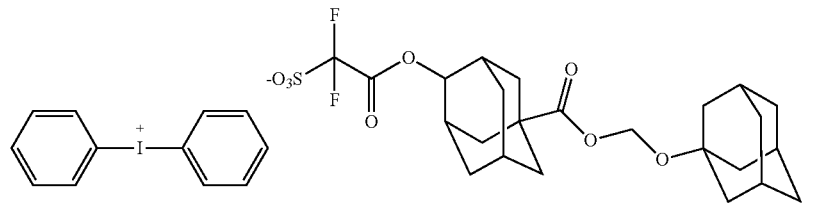

-continued
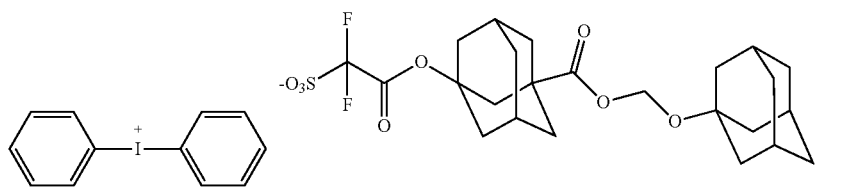
(I-102)
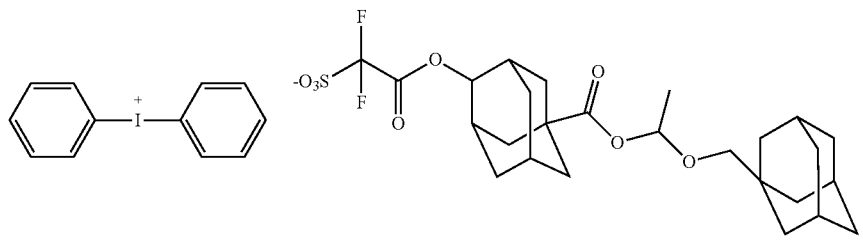
(I-143)
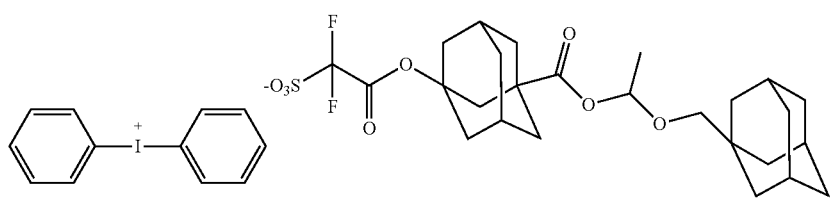
(I-144)
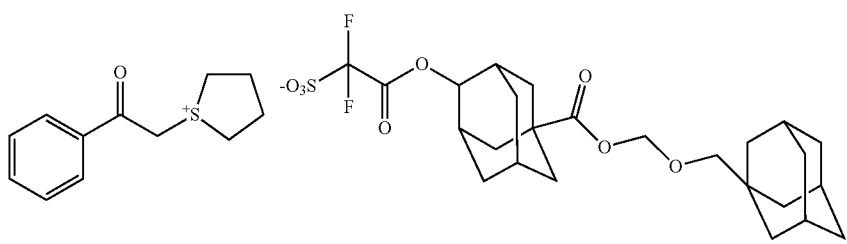
(I-19)
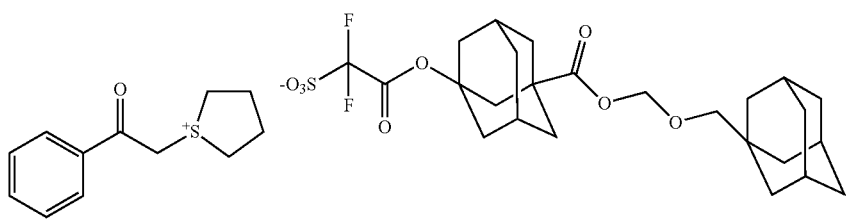
(I-20)
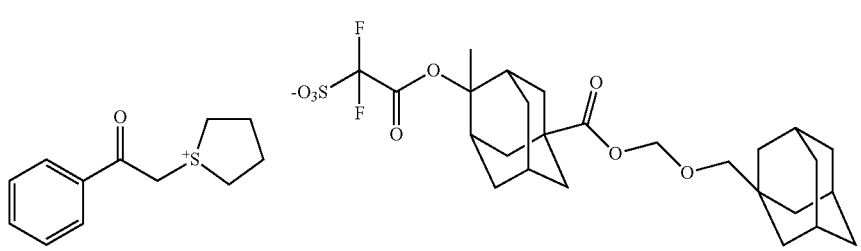
(I-21)
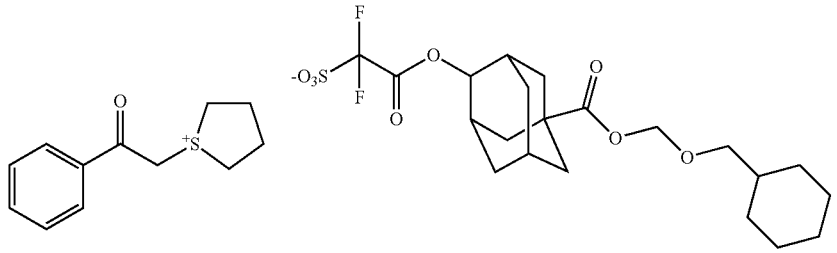
(I-22)

-continued
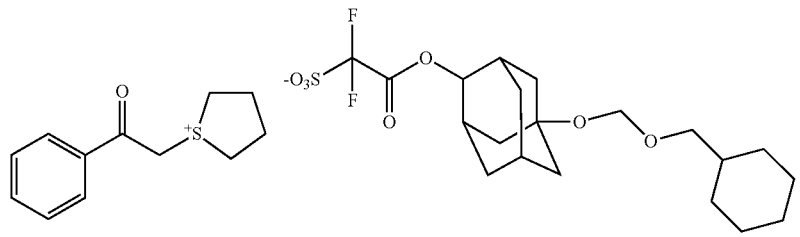
(I-23)
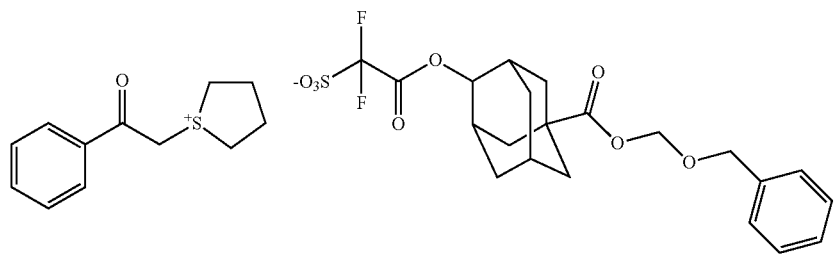
(I-24)
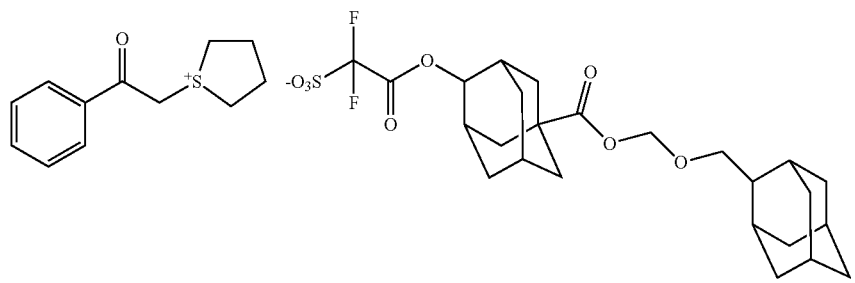
(I-70)
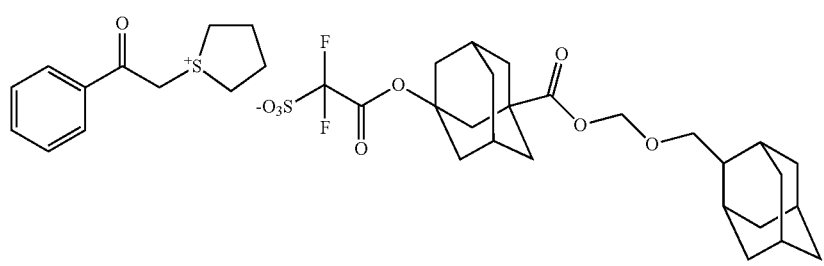
(I-71)
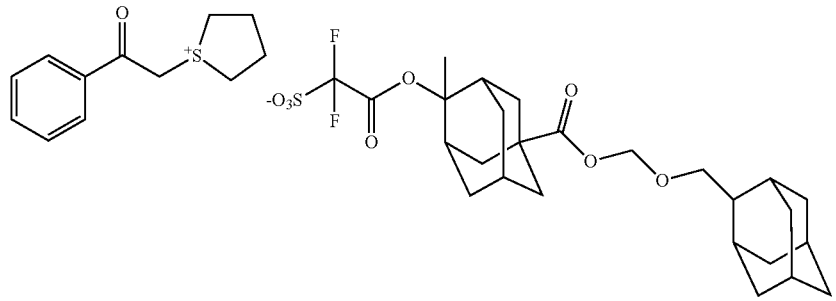
(I-72)
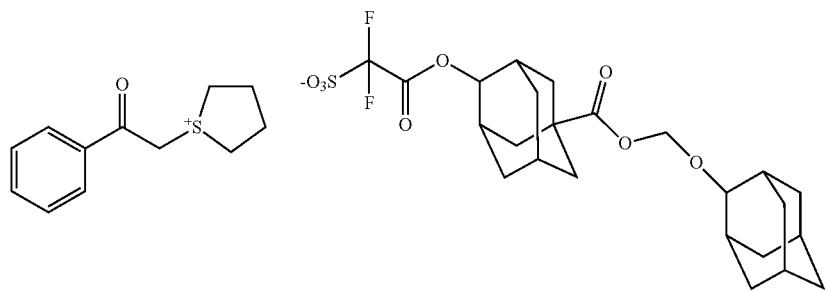
(I-103)

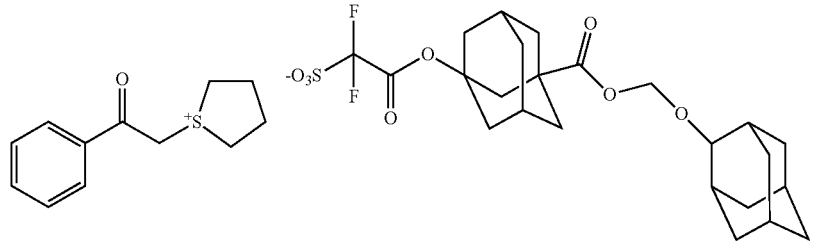
(I-104)

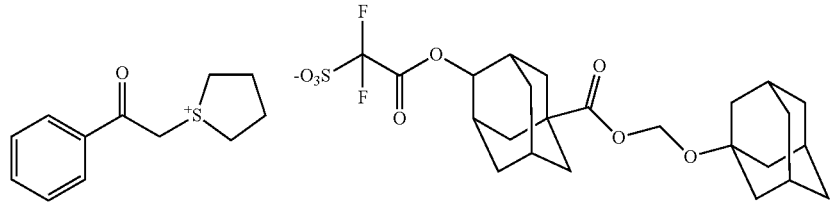
(I-105)

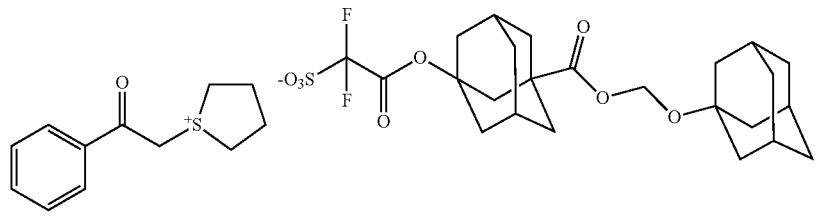
(I-106)

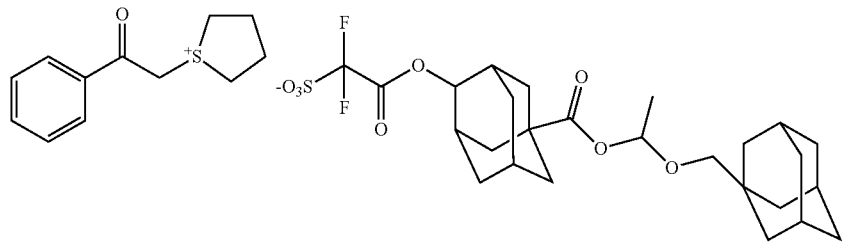
(I-149)

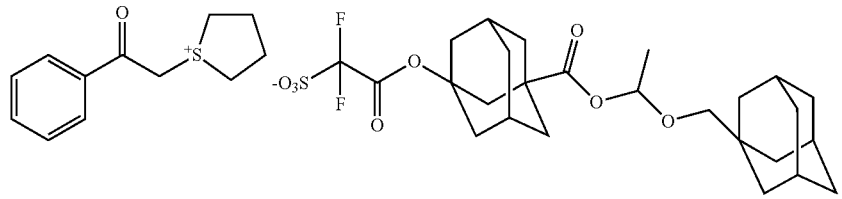
(I-150)

The process for producing SALT (I) will be illustrated by taking an example involving the salt of formula (b1) in which $L^1$ is *—CO—O— wherein * represents a binding position to —C($Q^1$)($Q^2$)-, and $L^2$ is a carbonyl group.

Such salt is produced by reacting a salt represented by formula (b1-f) with a salt represented by formula (b1-c) in a solvent such as acetonitrile.

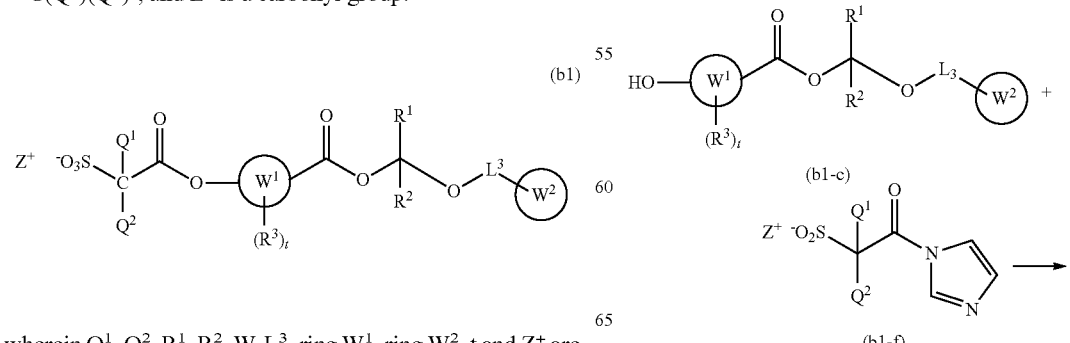

wherein $Q^1$, $Q^2$, $R^1$, $R^2$, W, $L^3$, ring $W^1$, ring $W^2$, t and $Z^+$ are the same as defined above.

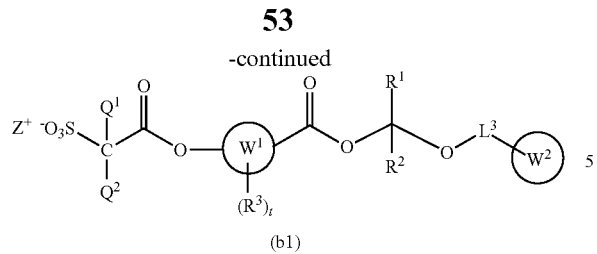

(b1)

The compound of formula (b1-c) can be produced by reacting the compound of formula (b1-a) with the compound of formula (b1-b) in the presence of a basic catalyst such as triethylamine, in a solvent such as chloroform, as shown in the reaction formula as follow.

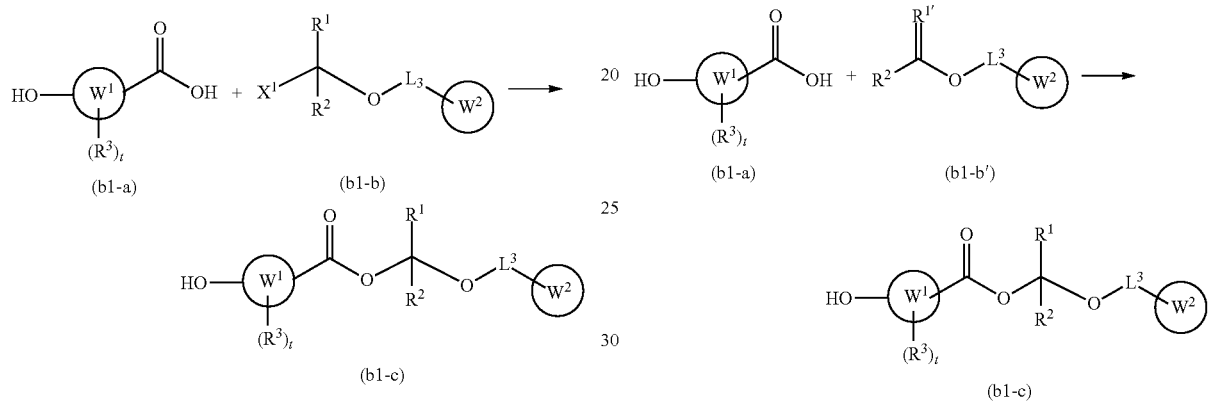

wherein $R^1$, $R^2$, $R^3$, $L^3$, ring $W^1$, ring $W^2$, and t are the same as defined above. $X^1$ represents a halogen atom.

Halogen atoms include a fluorine atom, a chlorine atom, a bromine atom and an iodine atom, preferably a chlorine atom.

The compound of formula (b1-a) includes a compound as shown bellow:

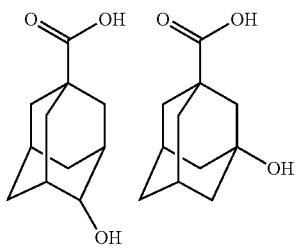

The compound of formula (b1-b) includes a compound as shown bellow:

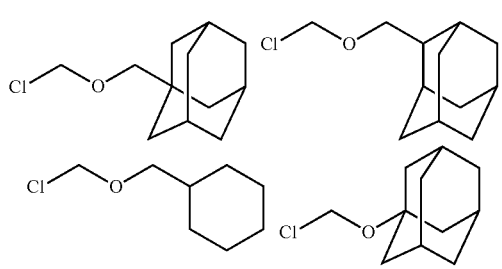

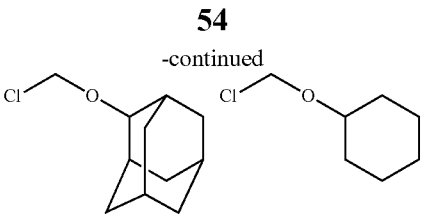

The compound of formula (b1-c) can also be produced by reacting the compound of formula (b1-a) with the compound of formula (b1-b') in the presence of an acid catalyst such as canphorsulfonic acid, in a solvent such as chloroform, as shown in the reaction formula as follow.

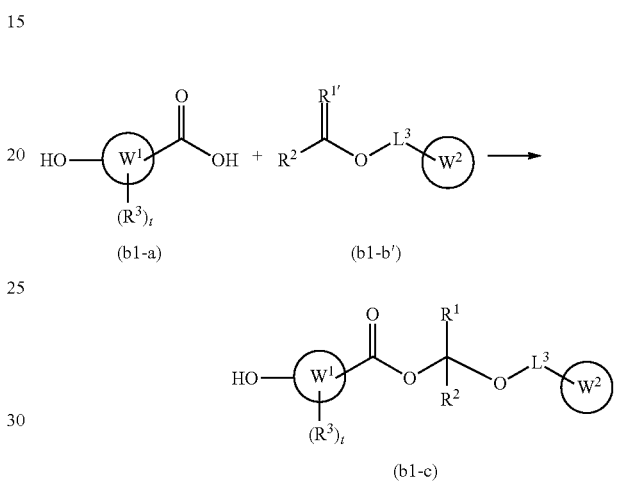

wherein represents a C1-6 alkylidene group,

The ring $W^1$, ring $W^2$, $R^2$, $R^3$, $L^3$ and t are the same as defined above.

In the formula, preferable scopes of the ring $W^1$, ring $W^2$, $R^2$, $R^3$, $L^3$ and t are same as mentioned concerning the formula (I).

The compound of formula (b1-b') includes the compounds shown as follow:

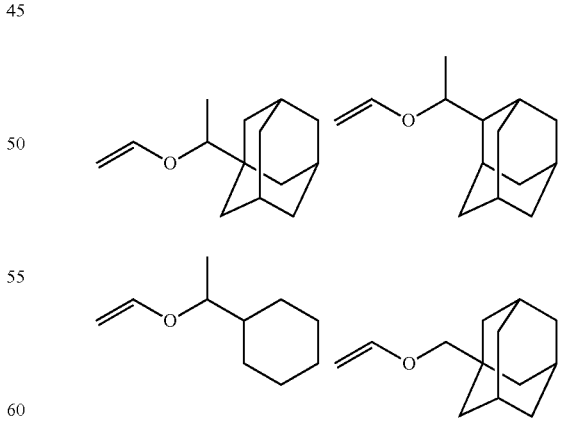

The compound represented by the formula (b1-c) can be produced by conducting the same reaction as above using the compound represented by the formula (b1-a1) instead of that represented by the formula (b1-a) followed by reducing the obtained compound.

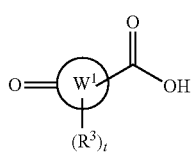

(b1-a1)

wherein the ring $W^1$, $R^3$ and t are the same as defined above.

In the formula (b1-a), preferable scopes of the ring $W^1$, $R^3$ and t are same as mentioned concerning the formula (I).

Specific example of the compound represented by the formula (b1-a1) includes the compound shown as follow,

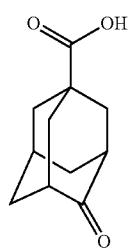 [SMILES: O=C1C2CC3CC1CC(C(=O)O)(C3)C2]

The reduction after reacting the compounds (b1-a) and (b1-b) can be conducted with a reducing agent in a solvent such as acetonitrile. Such reducing agent includes borone compounds such as sodium hydrogenboronate.

The compounds represented by the formulae (b1-a), (b1-a1), (b1-b) or) can be available on the market.

The compound represented by the formula (b1-f) can be produced by reacting the salt represented by the formula (b1-d) with the compound represented by the formula (b1-e), as shown in the reaction formula as follow.

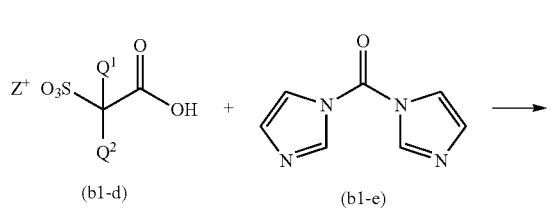

The salt represented by the formula (b1-d) can be produced by a method mentioned in JP2008-127367A1.

The compound represented by the formula (b1-e) can be available on the market.

Next, the acid generator of the present invention will be illustrated.

The acid generator of the present invention comprises SALT (I). The acid generator of the present invention can contain two or more kinds of SALT (I). The acid generator of the present invention may consist of SALT (I). The acid generator of the present invention can contain one or more known acid generators other than SALT (I) in addition to SALT (I). The acid generator of the present invention contains SALT (I) in an effective amount.

Preferable examples of the acid generator other than SALT (I) include salts represented by the formulae (B1-1) to (B1-17), the salts containing a triphenylsulfonium cation or a tritlylsulfonium cation are more preferable, and the salts represented by the formulae (B1-1), (B1-2), (B1-3), (B1-6), (B1-7), (B1-11), (B1-12), (51-13) and (B1-14) are especially preferable.

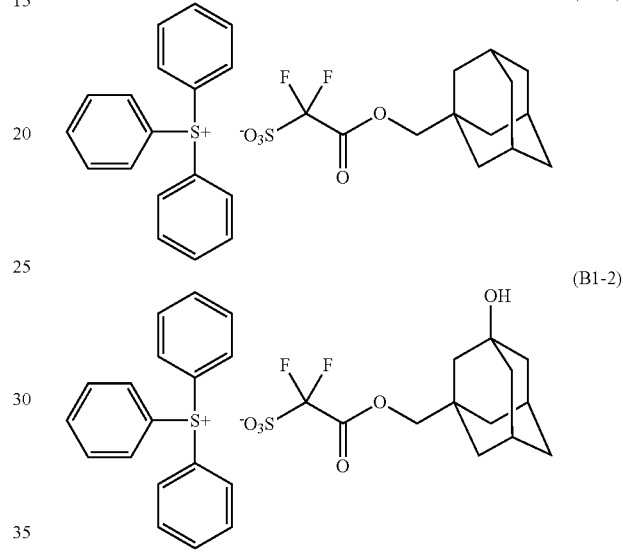

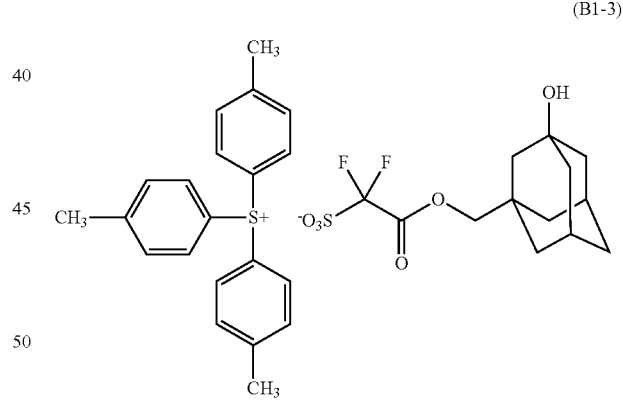

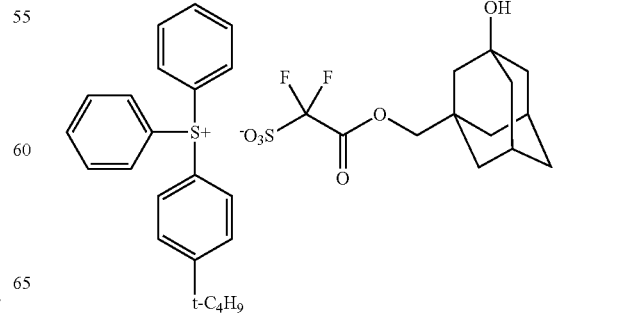

(B1-5)
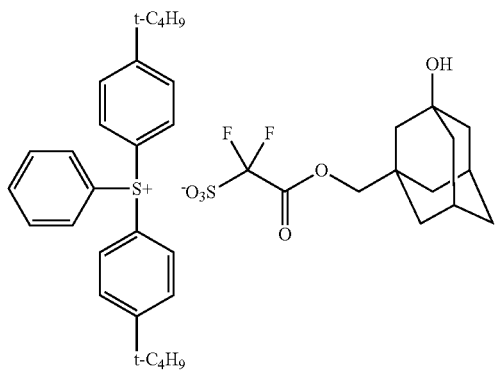
(B1-6)
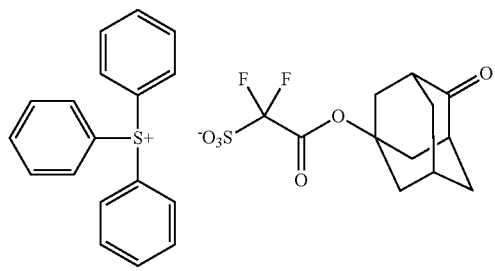
(B1-7)
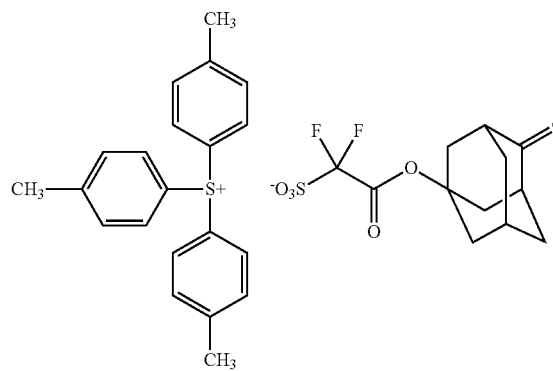
(B1-8)
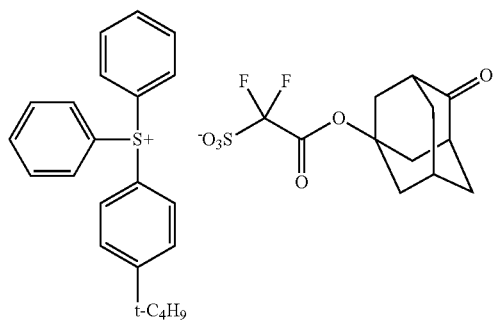
(B1-9)
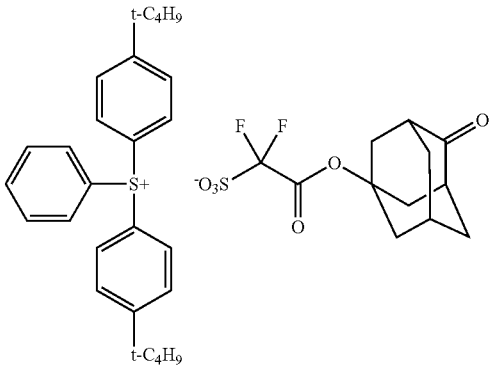
(B1-10)
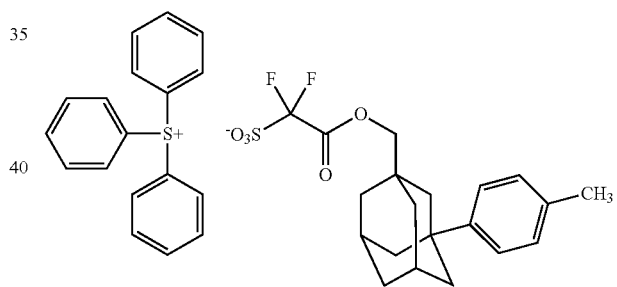
(B1-11)
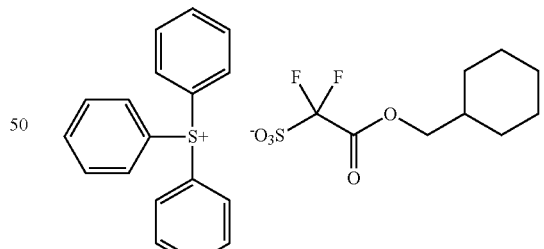
(B1-12)
(B-13)

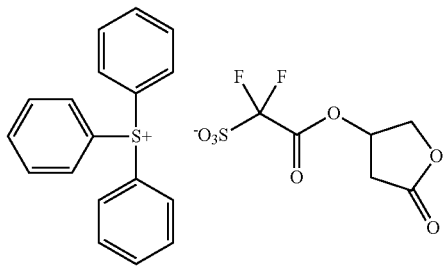
(B1-14)

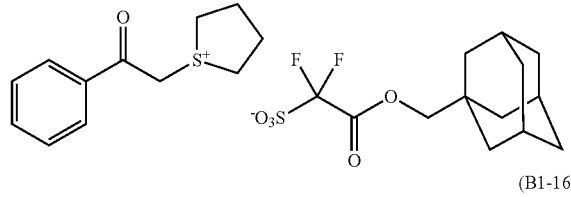
(B1-15)

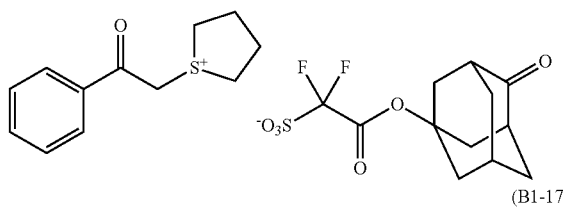
(B1-16)

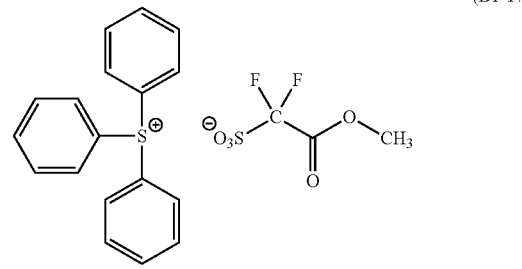
(B1-17)

When the acid generator of the present invention contains SALT (I) and the acid generator other than SALT (I), the content of SALT (I) is preferably 10 parts by weight or more and more preferably 30 parts by weight or more per 100 parts by weight of the acid generator of the present invention, and the content of SALT (I) is preferably 90 parts by weight or less and more preferably 70 parts by weight or less per 100 parts by weight of the acid generator of the present invention.

The content of SALT (I) is preferably 1 parts by weight or more and more preferably 3 parts by weight or more per 100 parts by weight of the resin having an acid-labile group, and the content of SALT (I) is preferably 30 parts by weight or less and more preferably 25 parts by weight or less per 100 parts by weight of the resin having an acid-labile group.

Next, the photoresist composition of the present invention will be illustrated.

The photoresist composition of the present invention comprises the acid generator of the present invention and a resin having an acid-labile group, being insoluble or poorly soluble in an aqueous alkali solution but becoming soluble in an aqueous alkali solution by the action of an acid. The photoresist composition comprises, as necessary, a basic compound and a solvent.

The resin is insoluble or poorly soluble in an alkali aqueous solution but becomes soluble in an alkali aqueous solution by the action of an acid. The resin has one or more acid-labile groups. In this specification, "an acid-labile group" means a group capable of being eliminated by the action of an acid.

Examples of the acid-labile group include a group represented by the formula (1):

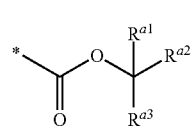

wherein $R^{a1}$, $R^{a2}$ and $R^{a3}$ independently each represent a C1-C8 alkyl group or a C3-C20 alicyclic hydrocarbon group, and $R^{a1}$ and $R^{a2}$ may be bonded each other to form a C2-C20 divalent hydrocarbon group,
and * represents a binding position,
and a group represented by the formula (2)

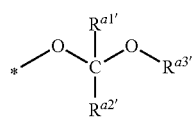

wherein $R^{a1'}$ and $R^{a2'}$ independently each represent hydrogen atom or a C1-C8 hydrocarbon group, and $R^{a3'}$ represents a C1-C20 hydrocarbon group, or Ra3' together with $R^{a1'}$ and $R^{a2'}$ represents a C2-C20 divalent hydrocarbon group in which a methylene group of the divalent hydrocarbon group may be replaced by —O— or —S—.

Specific examples of the C1-C8 alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings.

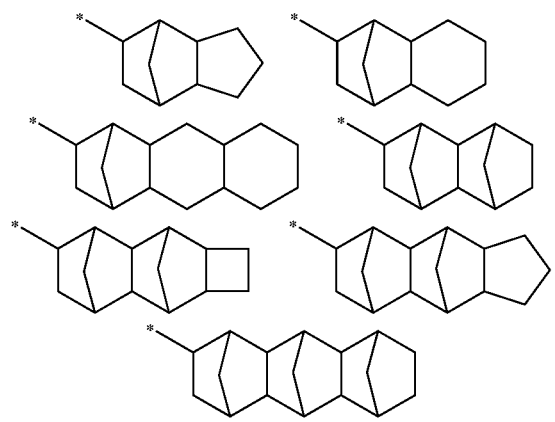

The alicyclic hydrocarbon group preferably has 3 to 16 carbon atoms.

when $R^{a1}$ and $R^{a2}$ of formula (1) are bonded each other to form a C2-C20 divalent hydrocarbon group, the moiety represented by —C($R^{a1}$)($R^{a2}$)($R^{a3}$) includes the following groups and the ring preferably has 3 to 12 carbon atoms.

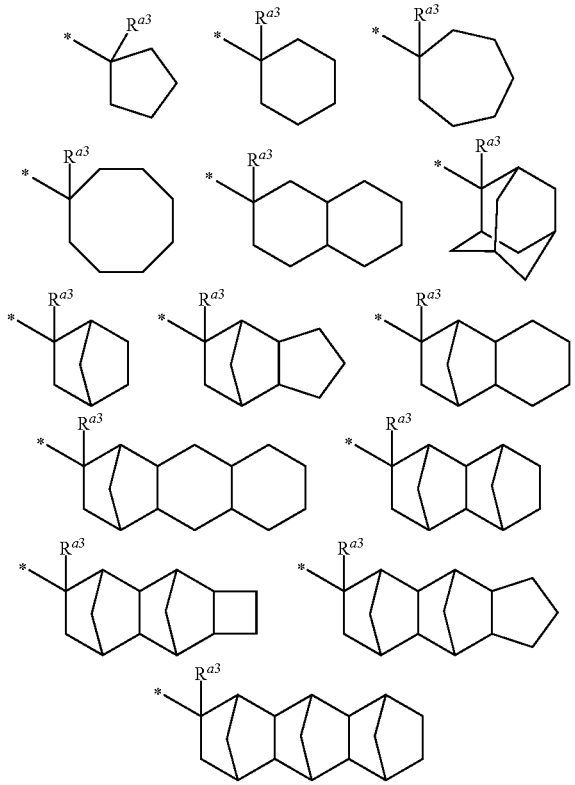

wherein $R^{a3}$ is the same as defined above and * represents a binding position to —O— of formula (1)

The group represented by the formula (1) wherein $R^{a1}$, $R^{a2}$ and $R^{a3}$ independently each represent a C1-C8 alkyl group such as a tert-butyl group, the group represented by the formula (1) wherein $R^{a1}$ and $R^{a2}$ are bonded each other to form an adamantyl ring and $R^{a3}$ is a C1-C8 alkyl group such as a 2-alkyladaman-2-yloxycarbonyl group, and the group represented by the formula (1) wherein $R^{a1}$ and $R^{a2}$ are C1-C8 alkyl groups and $R^{a3}$ is an adamantyl group such as a 1-(1-adaman-1-yl)-1-alkylalkoxycarbonyl group are preferable.

As to formula (2) examples of the hydrocarbon group include an aliphatic hydrocarbon group, an alicyclic hydrocarbon group and an aromatic hydrocarbon group.

Examples of the aliphatic hydrocarbon group and the alicyclic hydrocarbon group include the same as described above. Examples of the aromatic hydrocarbon group include an aryl group such as a phenyl group, a naphthyl group, a p-methylphenyl group, a p-tert-butylphenyl group, a p-adamantylphenyl group, a tolyl group, a xylyl group, a cumyl group, a mesityl group, a biphenyl group, an anthryl group, a phenanthryl group, a 2,6-diethylphenyl group and a 2-methyl-6-ethylphenyl group.

It is preferred that at least one of $R^{a1'}$ and $R^{a2'}$ is a hydrogen atom.

Examples of the group represented by formula (2) include the following.

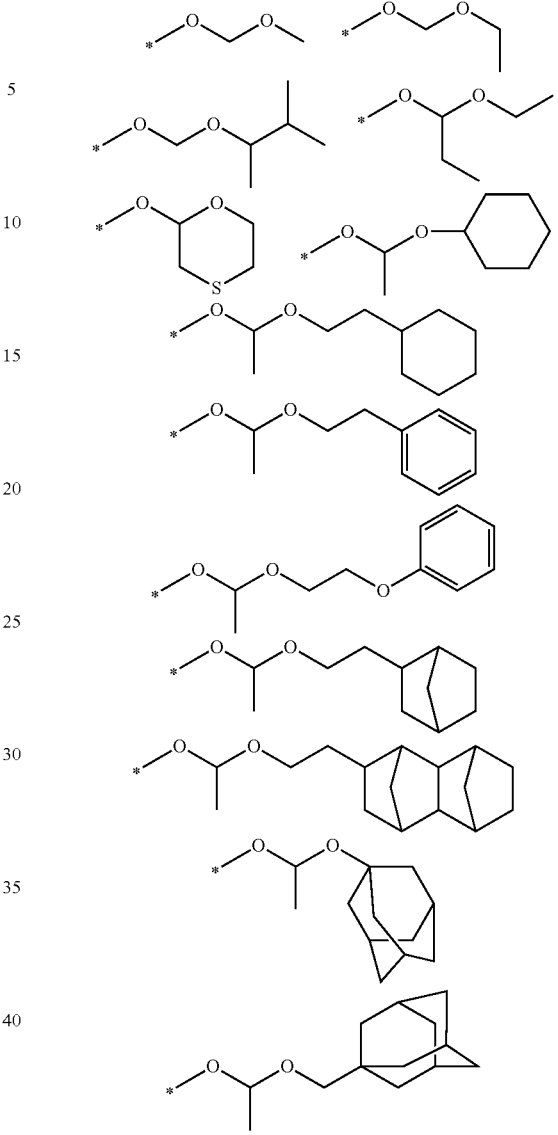

The compound having an acid-labile group is preferably a compound having an acid-labile group in its side chain and a carbon-carbon double bond, and is more preferably an acrylate compound having an acid-labile group in its side chain or a methacryalte compound having an acid-labile group in its side chain.

A compound having the group represented by the formula (1) or (2) in its side chain and a carbon-carbon double bond is preferable, and an acrylate monomer having the group represented by the formula (1) in its side chain or a methacrylate monomer having the group represented by the formula (1) in its side chain is more preferable.

An acrylate monomer having the group represented by the formula (1) in which $R^{a1}$ and $R^{a2}$ are bonded each other to form a C5-C20 alicycle together with the carbon atom to which they are bonded in its side chain or a methacryalte monomer having the group represented by the formula (1) in which $R^{a1}$ and $R^{a2}$ are bonded each other to form a C5-C20 alicycle together with the carbon atom to which they are bonded in its side chain is especially preferable.

Preferable examples of the compound having an acid-labile group comprise a compound represented by the formulae (a1-1) and (a1-2):

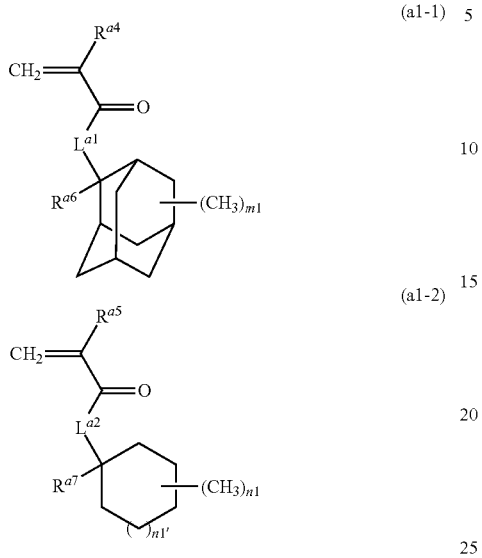

wherein $R^{a4}$ and $R^{a5}$ each independently represents a hydrogen atom or a methyl group, $R^{a6}$ and $R^{a7}$ each independently represents a C1-C10 aliphatic hydrocarbon group, $L^{a1}$ and $L^{a2}$ each independently represents *—O— or *—O—$(CH_2)_{k1}$—CO—O— in which * represents a binding position to —CO—, and k1 represents an integer of 1 to 7, and m1 represents an integer of 0 to 14, n1 represents an integer of 0 to 10, and n1' represents 0 to 3.

Examples of the aliphatic hydrocarbon group include a C1-C8 alkyl group such as a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group; and the saturated cyclic hydrocarbon group include a cyclohexyl group, a methylcyclohexyl group, a dimethylcyclohexyl group, a cycloheptyl group, a methylcycloheptyl group, a norbornyl group and a methylnorbornyl group.

The alkyl group preferably has 1 to 6 carbon atoms, and the saturated cyclic hydrocarbon group preferably has 3 to 8 carbon atoms and more preferably 3 to 6 carbon atoms.

$L^{a1}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—. $L^{a2}$ is preferably *—O— or *—O—$(CH_2)_{f1}$—CO—O— in which * represents a binding position to —CO—, and f1 is the same as defined above, and is more preferably *—O— or *—O—$CH_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1, and n1' is preferably 0 or 3.

$R^{a4}$ and $R^{a5}$ are preferably methyl groups.

Particularly when the photoresist composition contains a resin derived from a monomer having a bulky structure such as a saturated cyclic hydrocarbon group, the photoresist composition having excellent resolution tends to be obtained.

Examples of the monomer represented by the formula (a1-1) include the compounds mentioned in JP2010-204646A. As the structural unit represented by the formula (a1-1), preferred are structural units represented by formulae (a1-1-1), (a1-1-2), (a1-1-3), (a1-1-4), (a1-1-5), (a1-1-6), (a1-1-7) and (a1-1-8), more preferred are structural units represented by formulae (a1-1-1), (a1-1-2), (a1-1-3), (a1-1-4), and still more preferred are structural units represented by formulae (a1-1-2) and (a1-1-3).

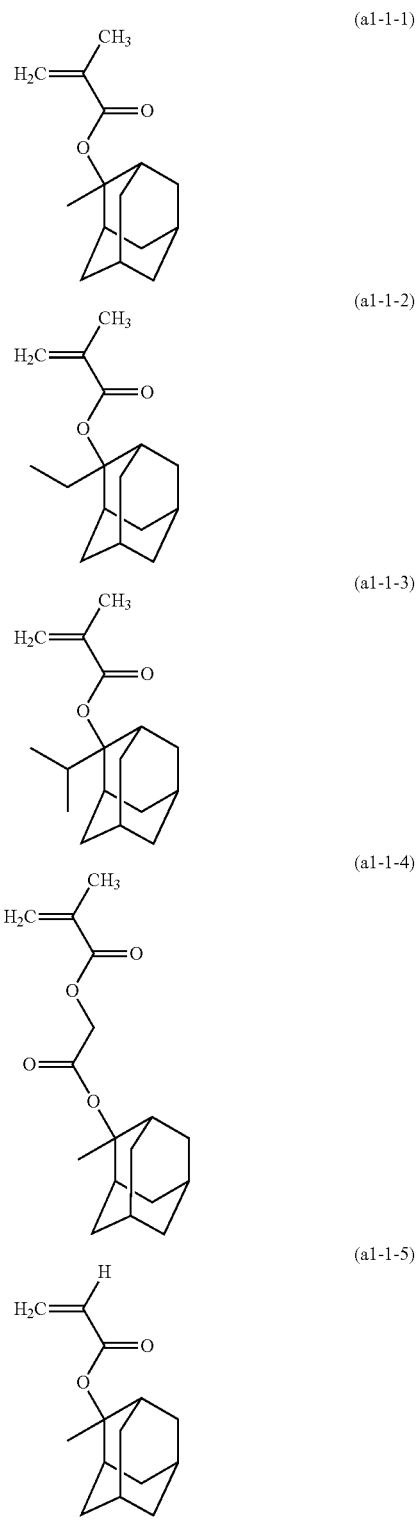

(a1-1-6)
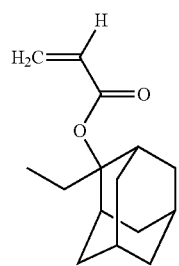

(a1-1-7)
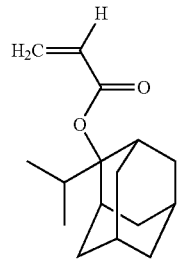

(a1-1-8)
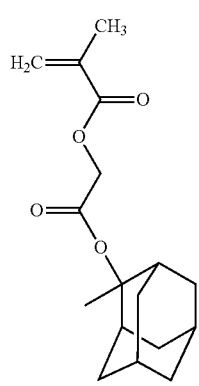

(a1-2-2)
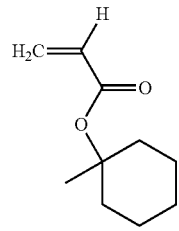

(a1-2-3)
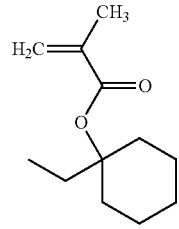

(a1-2-4)
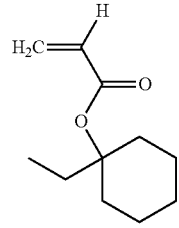

(a1-2-5)
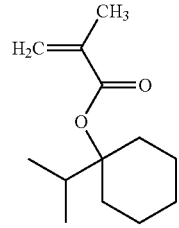

(a1-2-6)
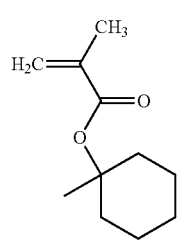

Monomers represented by the formula (a1-1) include compounds mentioned in JP2010-204646A.

Examples of monomers represented by the formula (a1-2) include 1-ethyl-cyclopentant-1-yl(meth)acrylate, 1-ethyl-cyclohexan-1-yl(meth)acrylate, 1-ethyl-cyclohept-1-yl (meth)acrylate, 1-methyl-cyclopent-1-yl(meth)acrylate, and 1-isopropyl-cyclopent-1-yl(meth)acrylate.

As the monomer represented by the formula (a1-2), preferred are those represented by formulae (a1-2-1), (a1-2-2), (a1-2-3), (a1-2-4), (a1-2-5) and (a1-2-6), more preferred are those represented by formulae (a1-2-1), (a1-2-2), (a1-2-3) and (a1-2-4), and still more preferred are those represented by formula (a1-2-3).

(a1-2-1)

The content of the structural unit represented by the formula (a1-1) and/or (a1-2) in the resin is usually 10 to 95% by mole, preferably 15 to 90% by mole and more preferably 20 to 85% by mole based on 100% by mole of all the structural units of the resin.

The resin can have two or more kinds of structural units having an acid-labile group.

The resin preferably contains the structural unit having an acid-labile group and a structural unit having no acid-labile group. The resin can have two or more kinds of structural units derived from the monomers having no acid-labile group. When the resin contains the structural unit having an acid-labile group and the structural unit having no acid-labile group, the content of the structural unit having an acid-labile group is usually 10 to 80% by mole and preferably 20 to 60% by mole based on total molar of all the structural units of the resin. When the resin has these structural units in the above-mentioned proportion, the photoresist pattern obtained from the photoresist composition of the present invention can have more improved resistance to dry-etching.

The monomer having no acid-labile group preferably contains one or more hydroxyl groups or a lactone ring. When the resin contains the structural unit derived from the monomer having acid-labile group and having a hydroxyl groups or a lactone ring, a photoresist composition having good resolution and adhesiveness of photoresist to a substrate tends to be obtained.

When KrF excimer laser (wavelength: 248 nm) lithography system, or a high energy laser such as electron beam and extreme ultraviolet is used as an exposure system, the resin having no acid-labile group and having a hydroxyl groups is preferable. When ArF excimer laser (wavelength: 193 nm) is used as an exposure system, the resin having acid-labile group and having a hydroxylamadantyl is preferable.

Examples of the monomer having no acid-labile group and having a hydroxyl groups include one having a phenolic hydroxyl group, represented by the formula (a2-0):

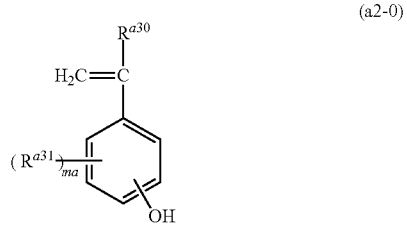

(a2-0)

wherein $R^{a30}$ represents a hydrogen atom, a halogen atom, a C1-C6 alkyl group or a C1-C6 halogenated alkyl group, $R^{a31}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable, Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

Such resin having a phenolic hydroxyl group can be produced, for example, by radical-polymerizing a (meth)acrylate monomer, acetoxystylene and stylene, followed by deacetylation with an acid. Monomers having a phenolic hydroxyl group include compounds mentioned in JP2010-204634A, preferably those represented by the formulae (a2-0-1) and (a2-0-2). For production of the resin, the compound having a phenolic hydroxyl group protected by a suitable protecting group is used.

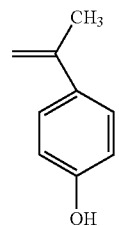

(a2-0-1)

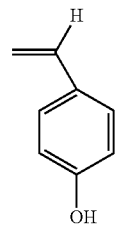

(a2-0-2)

When the resin contains the structural unit derived from the monomer represented by the formula (a2-0), the content of the structural unit is usually 5 to 90% by mole and preferably 10 to 85% by mole and more preferably 15 to 80% by mole based on total molar of all the structural units of the resin.

Examples of the monomer having no acid-labile group and having a hydroxylamadantyl groups include one represented by the formula (a2-1):

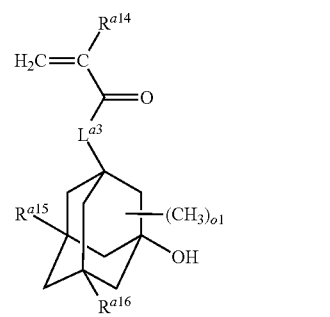

(a2-1)

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and o1 represents an integer of 0 to 10.

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO—O— in which * represents a binding position to —CO—, and f2 represents an integer of 1 to 4, is more preferably *—O— and *—O—$CH_2$—CO—O—, and is still more preferably *—O—, and o1 is preferably 0, 1, 2 or 3 and is more preferably 0 or 1.

Monomers represented by formula (a2-1) include compounds mentioned in JP2010-204646A.

Preferred examples of the structural unit represented by the formula (a2-1) include those represented by formulae (a2-1-1), to (a2-1-6).

(a2-1-1)
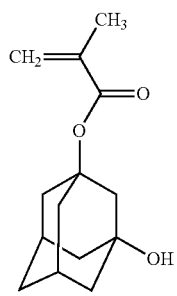

(a2-1-2)
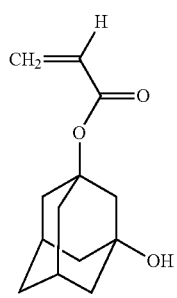

(a2-1-3)
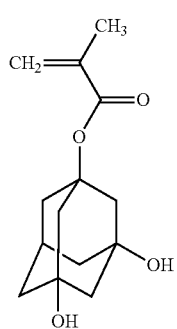

(a2-1-4)
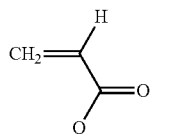

(a2-1-5)
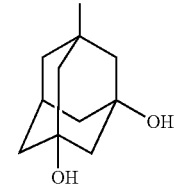

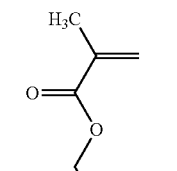

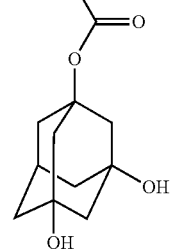

(a2-1-6)
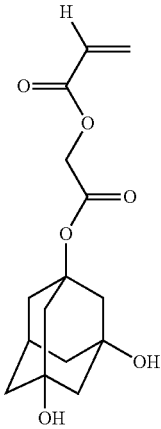

Among them, more preferred are the monomer represented by formulae (a2-1-1), (a2-1-2), (a2-1-3) and (a2-1-4), still more preferred are the monomer represented by formulae (a2-1-1) and (a2-1-3).

When the resin contains the structural unit derived from the monomer represented by the formula (a2-1), the content of the structural unit represented by the formula (a2-1) is usually 3 to 45% by mole based on total molar of all the structural units of the resin, and preferably 5 to 40% by mole, and more preferably 5 to 30% by mole, and especially preferably 5 to 35% by mole.

When the structural unit having no acid-labile group comprises lactone ring, examples of the lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of monomers having no acid-labile group and a lactone ring include those represented by the formulae (a3-1), (a3-2) and (a3-3):

(a3-1)
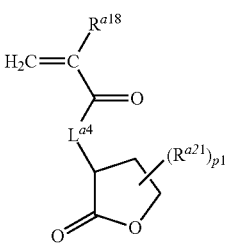

(a3-2)
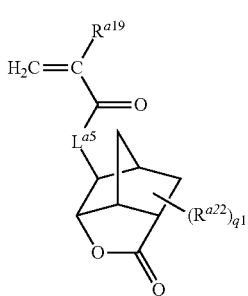

(a3-3)

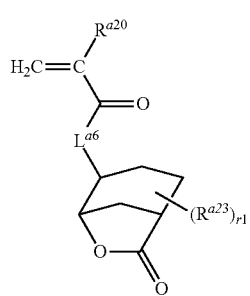

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a16}$, $R^{a19}$ and $R^{a20}$ each independently represent a hydrogen atom or a methyl group, $R^{a21}$ represents a C1-C4 alkyl group, $R^{a22}$ and $R^{a23}$ are independently in each occurrence a carboxyl group, a cyano group or a C1-C4 alkyl group, and p1 represents an integer of 0 to 5, q1 and r1 independently each represent an integer of 0 to 3.

It is preferred that $R^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O— and *—O—$CH_2$—CO—O—, and it is still more preferred that $L^{a4}$, $L^{a5}$ and $L^{a6}$ are *—O—.

$R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of monomer represented by the formula (a3-1) include those mentioned in JP2010-204646A.

Preferred monomers having a lactone ring are those represented by the formulae (a3-1-1) to (a3-1-4), the formulae (a3-2-1) to (a3-2-4) and the formulae (a3-3-1) to (a3-3-4), more preferred are those represented by the formulae (a3-1-1), (a3-1-2), (a3-2-3) and (a3-2-4), and still more preferred are those represented by the formulae (a3-1-1) and (a3-2-3).

(a3-1-1)

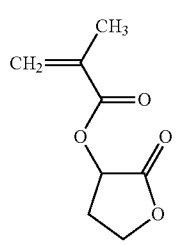

(a3-1-2)

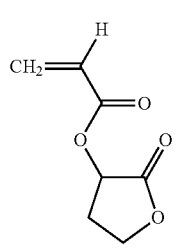

(a3-1-3)

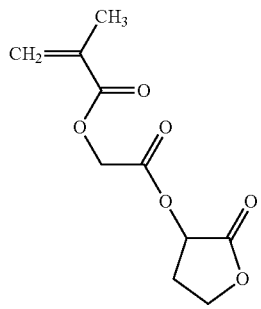

(a3-1-4)

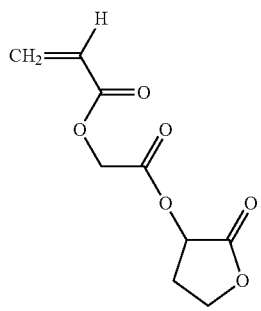

(a3-2-1)

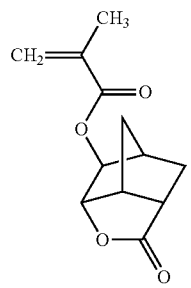

(a3-2-2)

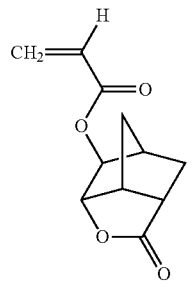

(a3-2-3)

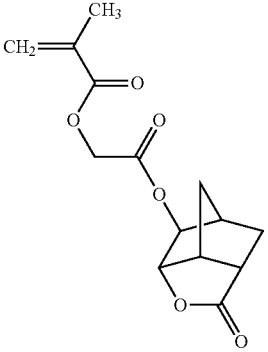

-continued

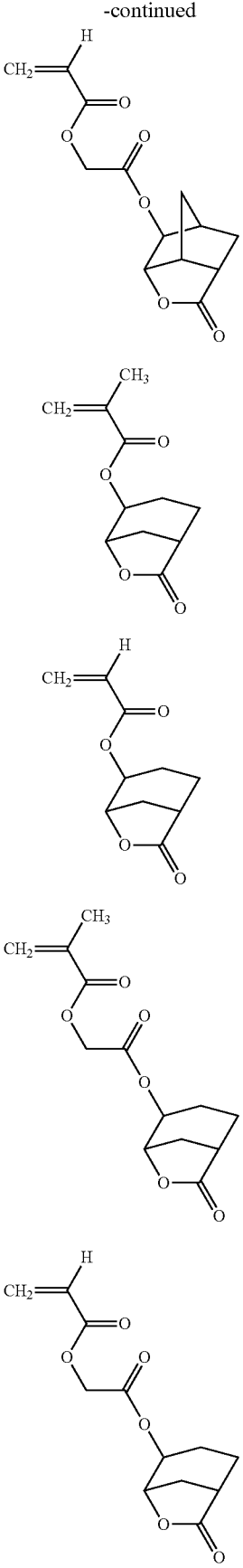

(a3-2-4)

(a3-3-1)

(a3-3-2)

(a3-3-3)

(a3-3-4)

When the resin contains the structural unit derived from a monomer having no acid-labile group and having a lactone ring, the content thereof is preferably 5 to 70% by mole based on total molar of all the structural units of the resin, and more preferably 10 to 65% by mole and more preferably 10 to 60% by mole.

The resin having an acid-labile group may contain the structural unit derived from a known monomer other than the monomers mentioned above.

The resin having an acid-labile group preferably contains a structural unit derived from a monomer represented by the formula (a1), in addition to a structural unit derived from a monomer represented by formula (a2) and/or formula (a3).

Preferable resin is a copolymer produced by polymerizing a monomer having an acid-labile group and the structural units having no acid-labile group, more preferable resin is a copolymer produced by polymerizing the monomer having an acid-labile group together with the monomer having one or more hydroxyl groups and/or the monomer having a lactone ring.

The monomer having an acid-labile group is preferably the monomer having an amadantyl group, e.g. the monomer represented by the formula (a1-1), and the monomer having a cyclohexyl group e.g. the monomer represented by the formula (a1-2), and more preferably the monomer having an amadantyl group.

The monomer having a hydroxy group is preferably the monomer having a hydroxyamadantyl group, e.g. the monomer represented by the formula (a2-1). The monomer having a lactone group is preferably the monomer having a γ-butyrolactone ring, e.g. the monomer represented by the formula (a3-1), and the monomer having a condensed ring formed from γ-butyrolactone ring and norbornane ring, e.g. the monomer represented by the formula (a3-2).

The resin can be produced according to known polymerization methods such as radical polymerization.

The resin usually has 2,500 or more of the weight-average molecular weight, preferably 3,000 or more of the weight-average molecular weight. The resin usually has 50,000 or less of the weight-average molecular weight, preferably has 30,000 or less of the weight-average molecular weight. The weight-average molecular weight can be measured with known methods such as liquid chromatography, gas chromatography or gel permeation chromatography.

The photoresist composition of the present invention usually includes 80% by weight or more of the resin based on sum of solid component. The photoresist composition of the present invention usually includes 99% by weight or less of the resin based on sum of solid component. In this specification, "solid component" means components other than solvent in the photoresist composition.

The photoresist compositions of the present invention can contain a basic compound as a quencher. The basic compound has the property that it can trap an acid, especially an acid generated from the acid generator by applying a radiation.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include a compound represented by the formula (C1-1):

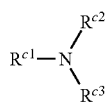
(C1)

wherein $R^{c1}$, $R^{c2}$ and $R^{c3}$ independently represent a hydrogen atom, a C1-C6 alkyl, group, a C5-C10 alicyclic hydrocarbon group or a C6-C10 aromatic hydrocarbon group, and the alkyl group and the alicyclic hydrocarbon group can have a substituent selected from the group consisting of a hydroxyl group, an amino group and a C1-C6 alkoxy group, and the aromatic hydrocarbon group can have a substituent selected from the group consisting of C1-C6 alkyl groups, a C5-C10 alicyclic hydrocarbon group, a hydroxyl group, an amino group, and a C1-C6 alkoxy group,

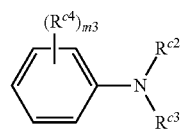
(C1-1)

wherein $R^{c2}$ and $R^{c3}$ are defined as above, each of $R^{c4}$ independently represents a C1-C6 alkyl group, a C1-C6 alkoxy group, a C5-C10 alicyclic hydrocarbon group or a C6-C10 aromatic hydrocarbon group, and m3 represents an integer of 0 to 3,

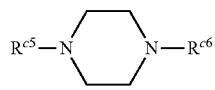
(C2)

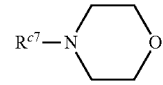
(C3)

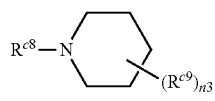
(C4)

wherein $R^{c5}$, $R^{c6}$, $R^{c7}$ and $R^{c8}$ are defined same as $R^{c1}$, each of $R^{c9}$ independently represents a C1-C6 alkyl group, a C3-C6 alicyclic group, or a C2-C6 alkanoyl group, and n3 represents an integer of 0 to 8,

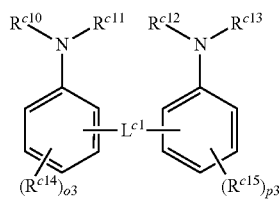
(C5)

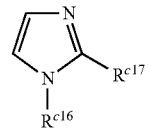
(C6)

wherein each of $R^{c10}$, $R^{c11}$, $R^{c12}$, $R^{c13}$ and $R^{c16}$ is defined same as $r^{c1}$, each of $R^{c14}$, $R^{c15}$ and $R^{c17}$ is defined same as $R^{c4}$, $L^{c1}$ represents a C1-C6 alkanediyl group, —CO—, —C(=NH)—, —S— or a combination thereof, and o3 and p3 respectively represent an integer of 0 to 3,

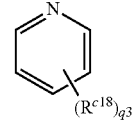
(C7)

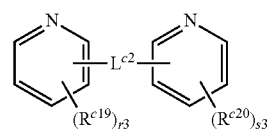
(C8)

wherein each of $R^{c18}$, $R^{c19}$ and $R^{c20}$ is defined same as $R^{c4}$, $L^{c2}$ represents a single bond, a C1-C6 alkanediyl group, —CO—, —C(=NH)—, —S— or a combination thereof, and q3, r3 and p3 respectively represent an integer of 0 to 3.

Examples of the compound represented by the formula (C1) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane. Among them, preferred is diisopropylaniline and more preferred is 2,6-diisopropylaniline Examples of the compound represented by the formula (C2) include piperazine.

Examples of the compound represented by the formula (C3) include morpholine.

Examples of the compound represented by the formula (C4) include piperidine and hindered amine compounds having a piperidine skeleton as disclosed in JP 11-52575 A.

Examples of the compound represented by the formula (C5) include 2,2'-methylenebisaniline.

Examples of the compound represented by the formula (C6) include imidazole and 4-methylimidazole.

Examples of the compound represented by the formula (C7) include pyridine and 4-methylpyridine.

Examples of the compound represented by the formula (C8) include di-2-pyridylketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine, 2,2'-dipicolylamine and bipyridine.

Examples of the ammonium salt include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

When the photoresist compositions contain the basic compound, the content thereof is usually 0.01 to 5%, preferably 0.01 to 3%, more preferably 0.01 to 1% by weight based on sum of solid component.

The photoresist compositions of the present invention usually contain a solvent.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention. The content can be measured with known methods such as liquid chromatography or liquid chromatography.

Examples of the solvent include a glycol ether ester such as ethyl cellosolve acetate, methyl cellosolve acetate and propylene glycol monomethyl ether acetate; a glycol, ether such as propylene glycol monomethyl ether; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The photoresist compositions of the present invention can contain, if necessary, a small amount of various additives such as a sensitizer, a dissolution inhibitor, other polymers, a surfactant, a stabilizer and a dye as long as the effect of the present invention is not prevented.

The photoresist compositions of the present invention can usually be prepared by mixing a solvent, an acid generator containing the SALT (I), and a resin having an acid-labile group, and if necessary a basic compound and/or additives at a suitable ratio for the composition, optionally followed by filtrating the mixture with a filter having 0.2 μm of a pore size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the present invention are useful for a chemically amplified photoresist composition.

A photoresist pattern can be produced by the following steps (1) to (5):
(1) a step of applying the photoresist composition of the present invention on a substrate,
(2) a Step of forming a photoresist film by conducting drying,
(3) a step of exposing the photoresist film to radiation,
(4) a step of baking the exposed photoresist film, and
(5) a step of developing the baked photoresist film to form a photoresist pattern.

The applying of the photoresist composition on a substrate is usually conducted using a conventional apparatus such as spin coater. The photoresist composition is preferably filtrated with filter having 0.2 μm of a pore size before applying. Examples of the substrate include a silicon wafer or a quartz wafer on which a sensor, a circuit, a transistor or the like is formed. The substrate may be treated with a coating material such as silane coupling agent including hexamethyldisilazane. Such silane coupling agent as available on the market can be used for the coating material.

The photoresist film is usually formed by heating the coat layer with a heating apparatus such as hot plate or a decompressor, to thereby dry off the solvent. The heating temperature is preferably 50 to 200° C., and the operation pressure is preferably 1 to $1.0*10^5$ Pa. These conditions can be selected in view of the solvent.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a F2 laser (wavelength: 157 nm), and a light source radiating harmonic laser light in a far UV region or a vacuum UV region by wavelength conversion of laser light from a solid laser light source (such as YAG or semiconductor laser). The exposure source may be electric beam or extremely ultraviolet (EUV).

The step of baking of the exposed photoresist film is so called post-exposure bake, which is conducted with heating means such as hot plates. The temperature of baking of the exposed photoresist film is preferably 50 to 200° C., and more preferably 70 to 150° C.

The development of the baked photoresist film is usually carried out with alkaline developer using a development apparatus. The development can be conducted by contacting the baked photoresist film into with an aqueous alkaline solution to thereby remove the film at exposed area from the substrate while remain the film at unexposed area, forming the photoresist pattern. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used.

After development, the photoresist pattern formed is preferably washed with ultrapure water, and the remained water on the photoresist pattern and the substrate is preferably removed.

The photoresist composition of the present invention is suitable for ArF excimer laser lithography, KrF excimer laser lithography, EUV exposure lithography and EB (electron beam) lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted.

The weight-average molecular weight of any material used in the following examples is a value found by gel permeation chromatography [Column: Three of TSKgel Multipore HXL-M with guard column, manufactured by TOSOH CORPORATION, Solvent: tetrahydrofuran, Flow rate: 1.0 Detector: RI Detector, Column temperature: 40° C., Injection volume: 100 μL] using standard polystyrene as a standard reference material.

Structures of compounds were determined by mass spectrometry (Liquid Chromatography; 1100 Type, manufactured by AGILENT TECHNOLOGIES LTD., Mass Spectrometry:

LC/MSD Type, manufactured by AGILENT TECHNOLOGIES LTD.). Hereinafter, the value of the peak in the mass spectrometry is referred to as "MASS".

Example 1

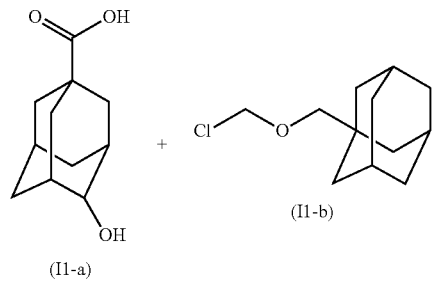

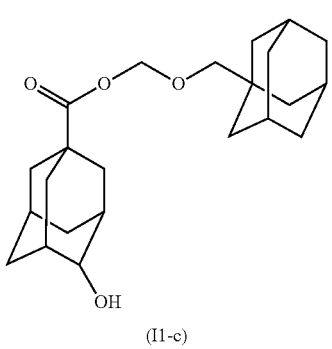

Feeding 5 parts of the compound represented by formula (I1-a) and 25 parts of dimethylformamide into a reactor, they was stirred at 23° C. for 30 minutes, and then 3.87 parts of triethylamine was dropped thereto, followed by stirring them at 23° C. for 30 minutes. To the resulting mixture, dropped thereinto was 6.57 parts of the compound represented by formula (I1-b) dissolved in 6.57 parts of dimethylformamide, followed by stirring them at 23° C. for 2 hours. To the resulting reaction mixture, 23.5 parts of deionized water and 140.99 parts of ethyl acetate were added, followed by stirring them at 23° C. for 30 minutes to separate into an organic layer. To the organic layer, 70.5 parts of deionized water was added, followed by stirring them at 23° C. for 30 minutes to separate into an organic layer.

Such washing with deionized water was further conducted six times. The resulting organic layer was concentrated and 92.2 parts of n-heptane was added thereto to obtain 2.85 parts of the compound represented by formula (I1-c).

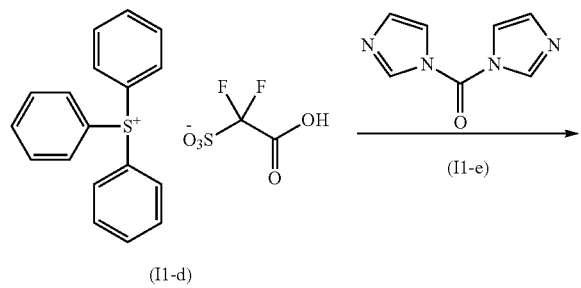

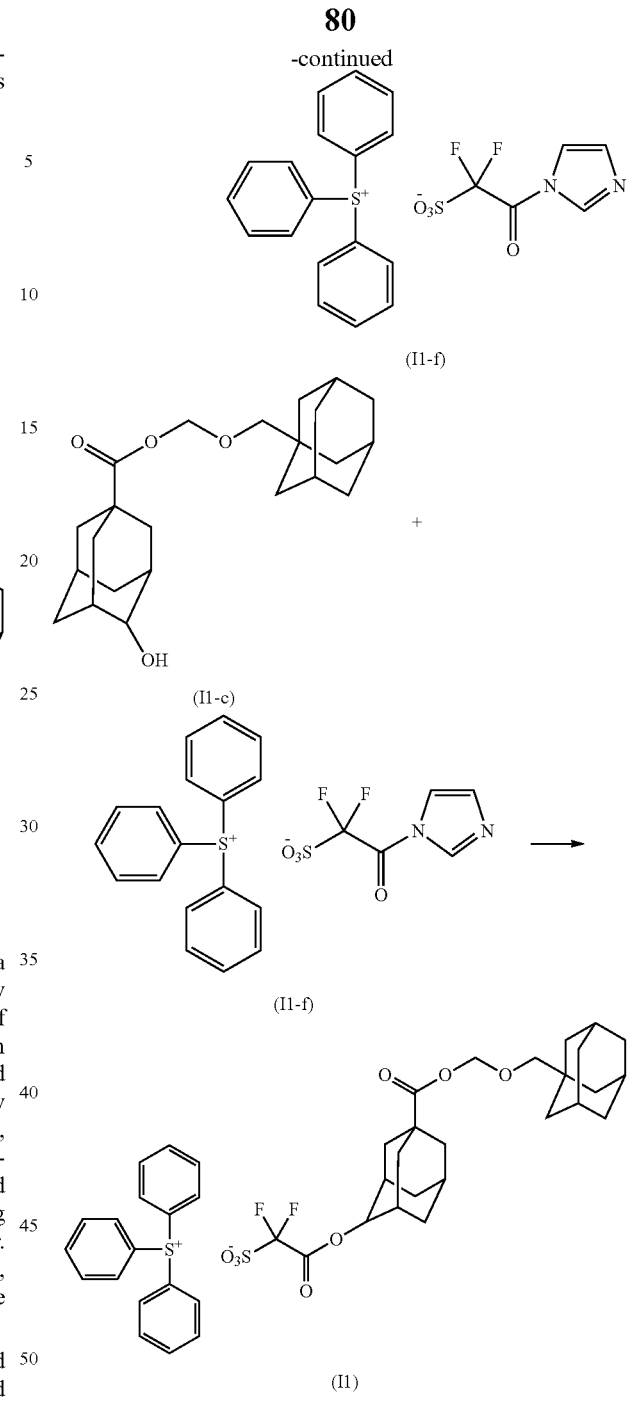

Salt represented by formula (I1-d) was prepared by the method described in JP2008-127367A1. Feeding 2.99 parts of the compound represented by formula (I1-d) and 1.5 parts of acetonitrile thereto, they were stirred at 23° C. for 30 minutes, 1.3 parts of the compound represented by formula (I1-e) was fed thereto, stirring them at 70° C. for 2 hours. The resulting reaction mixture was cooled to 23° C., filtrating them to obtain a solution containing the compound represented by formula (I1-f). To the solution, fed was a solution in which 1.3 parts of the compound represented by formula (I1-c) was dissolved in 6.86 parts of chloroform, stirring them at 23° C. for 23 hours. Concentrating the resulting reaction mixture, 58.47 parts of chloroform and 29.24 parts of 2% oxalic acid aqueous solution were fed thereto and stirred to separate into an organic layer. Such washing with oxalic acid was conducted twice. The resulting organic layer was concentrated and then dissolved in 27.27 parts of acetonitrile, followed by concentrating it. To the concentrate, 70 parts of tert-butylmethylether was added and then a supernatant was removed therefrom. The resulting residue was dissolved in acetonitrile, followed by concentrating it to obtain 3.58 parts of the salt represented by formula (I1).

MASS(ESI(+) Spectrum): $M^+$ 263.1
MASS(ESI(−) Spectrum); $M^−$ 531.2

Example 2

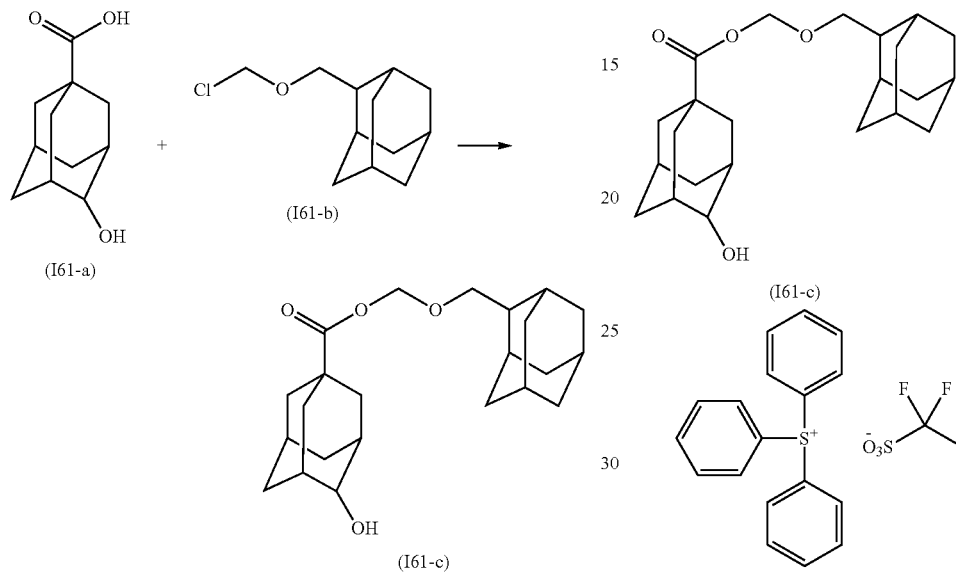

(I61-a) + (I61-b) → (I61-c)

Into a reactor, 5 parts of a compound represented by the formula (I61-a) and 25 parts of dimethylformamide were fed, stirring them at 23° C. for 30 minutes. Thereto 3.87 part of triethylamine was dropped thereto, followed by stirring them at 23° C. for 30 minutes. To the resulting mixture, dropped was a solution in which 6.57 parts of a compound represented by the formula (I61-b) was dissolved in 6.57 parts of dimethylformamide over 30 minutes, followed by stirring them at 23° C. for 2 hours. To the resulting reaction mixture, 23.5 parts of deionized water and 140.99 parts of ethyl acetate was added, and then stirred at 23° C. or 30 minutes, followed by separating them into an organic layer. To the resulting organic layer, 70.5 parts of deionized water was fed and then stirred at 23° C. for 30 minutes, followed by separating them into an organic layer. Such washing with water was conducted further six times. The organic layer was concentrated, and then 90 parts of n-heptane was added thereto and stirred, followed by filtrating it to obtain 3.12 parts of the salt represented by formula (I61-c).

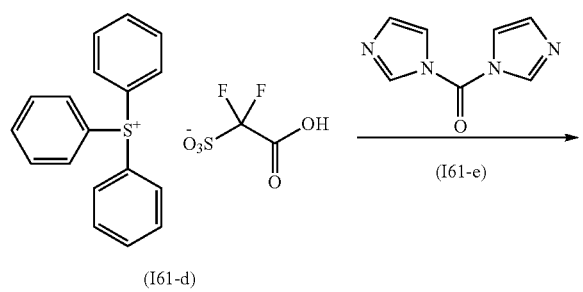

(I61-d) + (I61-e) →

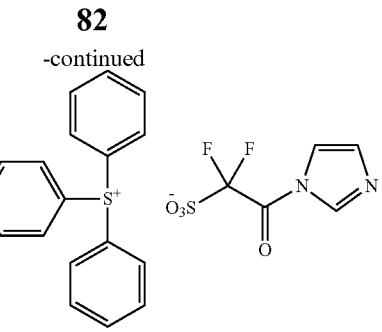

(I61-f)

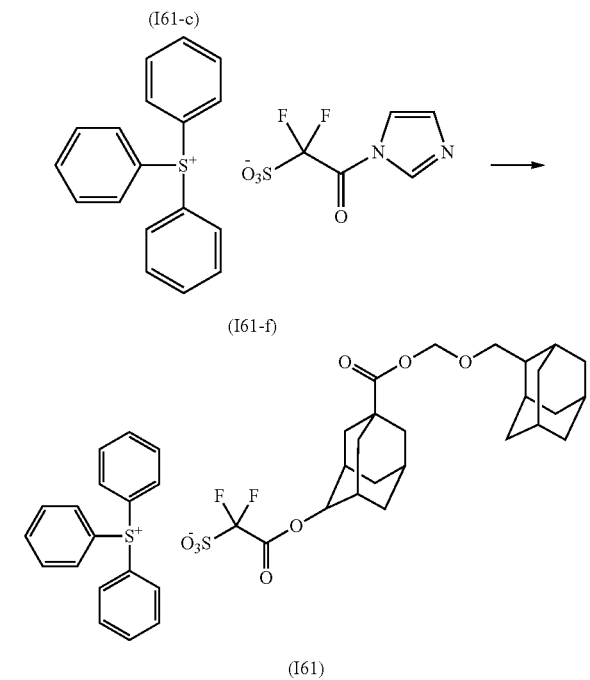

(I61-f) + (I61-c) → (I61)

Salt represented by formula (I61-d) was prepared by the method described in JP2008-127367A1. Feeding 2.99 parts of the compound represented by formula (I161-d) and 15 parts of acetonitrile thereinto, they were stirred at 23° C. for 30 minutes, 1.3 parts of the compound represented by formula (I161-e) was fed thereto, stirring them at 70° C. for 2 hours. The resulting reaction mixture was cooled to filtrating them to obtain a solution containing the compound represented by formula (I61-f). To the solution, fed was a solution in which 2.3 parts of the compound represented by formula (I61-c) was dissolved in 6.89 parts of chloroform, stirring them at 23° C. for 23 hours. Concentrating the resulting reaction mixture, 68 parts of chloroform and 30 parts of 2% oxalic acid aqueous solution were fed thereto and stirred to separate into an organic layer. Such washing with oxalic acid was conducted twice. The resulting organic layer was concentrated and then 30 parts of deionaized water was fed and stirred, followed by separating it. Such washing with water was conducted four times. To the concentrate 70 parts of tert-butylmethylether was added and then a supernatant was removed therefrom. The resulting residue was dissolved in acetonitrile, followed by concentrating it to obtain 3.66 parts of the salt represented by formula (I2).

MASS(ESI(+)) Spectrum): M+ 263.1

MASS(ESI(−)) Spectrum): M− 531.2

Example 3

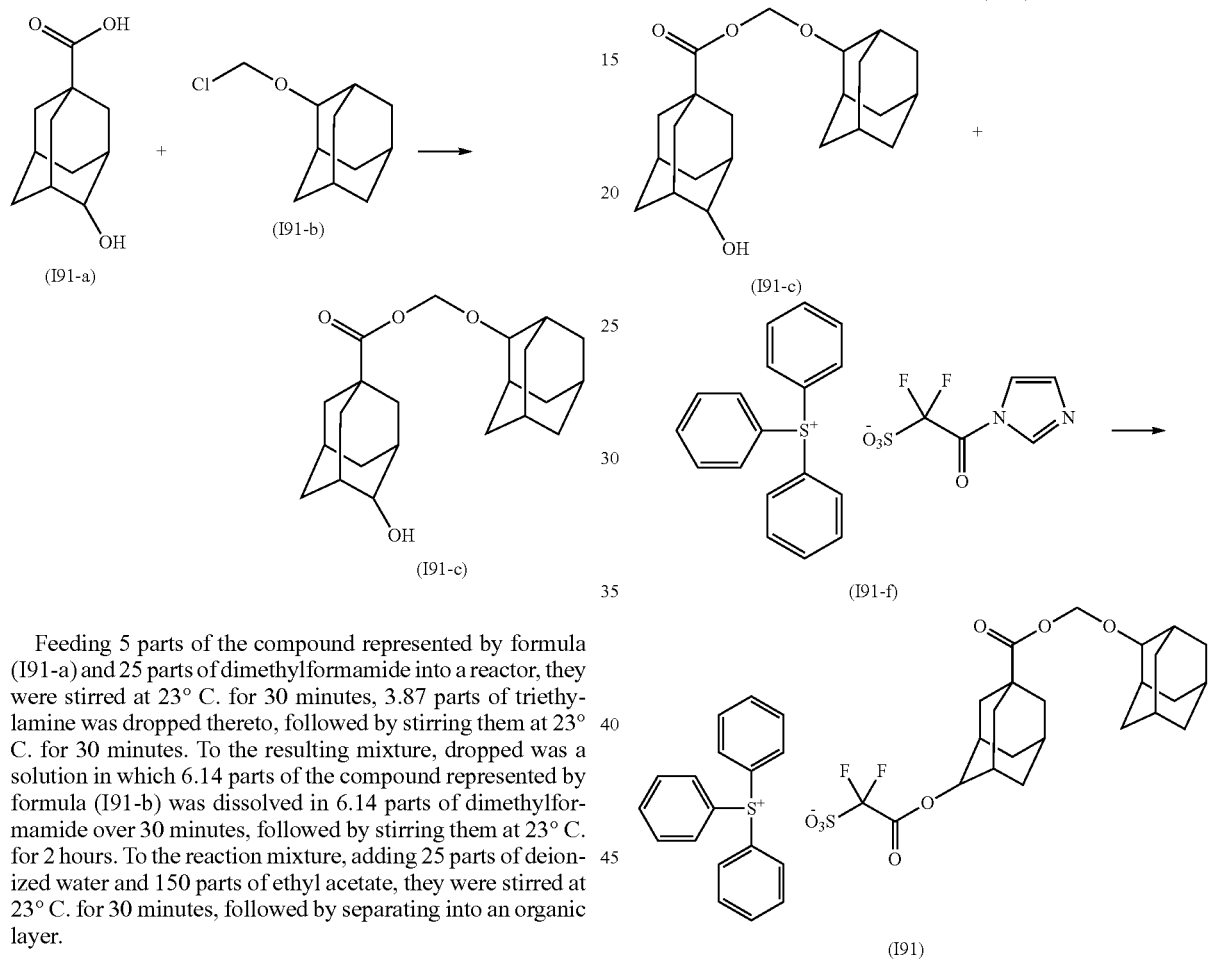

Feeding 5 parts of the compound represented by formula (I91-a) and 25 parts of dimethylformamide into a reactor, they were stirred at 23° C. for 30 minutes, 3.87 parts of triethylamine was dropped thereto, followed by stirring them at 23° C. for 30 minutes. To the resulting mixture, dropped was a solution in which 6.14 parts of the compound represented by formula (I91-b) was dissolved in 6.14 parts of dimethylformamide over 30 minutes, followed by stirring them at 23° C. for 2 hours. To the reaction mixture, adding 25 parts of deionized water and 150 parts of ethyl acetate, they were stirred at 23° C. for 30 minutes, followed by separating into an organic layer.

Such washing with water was conducted further five times. Concentrating the resulting reaction mixture, 92.2 parts of n-heptane was fed thereto and stirred, followed by filtrating it to obtain 2.69 parts of compound represented by formula (I91-c).

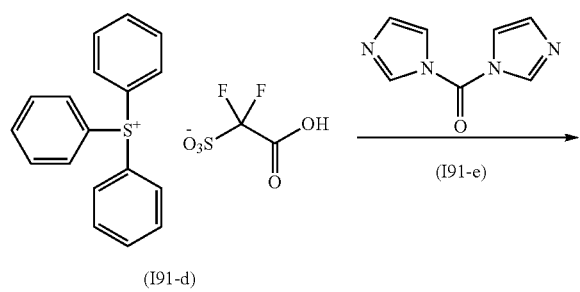

Salt represented by formula (I91-d) was prepared by the method described in J22008-127367A1.

Feeding 2.99 parts of the compound represented by formula (I91-d) and 15 parts of acetonitrile thereinto, they were stirred at 23° C. for 30 minutes, 1.3 parts of the compound represented by formula (I91-e) was fed thereto, stirring them at 70° C. for 2 hours. The resulting reaction mixture was cooled to 23° C., filtrating them to obtain a solution containing the compound represented by formula (I91-f). To the solution, fed was a solution in which 2.12 parts of the compound represented by formula (I91-c) was dissolved in 6.36 parts of chloroform, stirring them at 23° C. for 23 hours. Concentrating the resulting reaction mixture, 60 parts of chloroform and 30 parts of 2% oxalic acid aqueous solution were fed thereto and stirred to separate into an organic layer. Such washing with oxalic acid was conducted twice.

Into the resulting organic layer 30 parts of deionaized water was fed and stirred, followed by separating it. Such washing with deionaized water was conducted five times. To the concentrate 30 parts of acetonitrile was added, followed by concentrating it.

To the concentrate 50 parts of tert-butylmethylether was added and then a supernatant was removed therefrom. The resulting residue was dissolved in acetonitrile, followed by concentrating it to obtain 3.46 parts of the salt represented by formula (I91).

MASS(ESI(+) Spectrum): M⁺ 263.1
MASS(ESI(−) Spectrum): M⁻ 517.2

Example 4

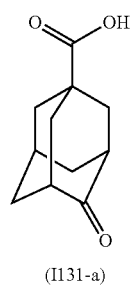
(I131-a)

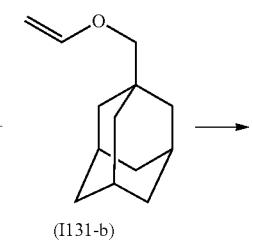
(I131-b)

(I131-c)

Feeding 5 parts of the compound represented by formula (I131-a) and 35 parts of chloroform into a reactor, they were stirred at 23° C. for 30 minutes, and then added thereto was a mixture of 0.0012 parts of canphersulfonic acid and 0.5988 parts of chloroform, followed by stirring them at 23° C. for 30 minutes. To the resulting mixture, dropped was a solution in which 5.17 parts of the compound represented by formula (I131-b) was dissolved in 10.34 parts of chloroform over 30 minutes, followed by stirring them at 23° C. for 17 hours, Then 21.63 parts of 2% aqueous sodium hydrocarbonate solution was added thereto and then stirred at 23° C. for 30 minutes, followed by separating into an organic layer. Thereto 22.67 parts of deionized water was fed and stirred at 23° C. for 30 minutes, followed by separating into an organic layer. Such washing with water was conducted further five times. Concentrating the resulting reaction mixture, 8.49 parts of compound represented by formula (I131-c) was obtained.

(I131-c)

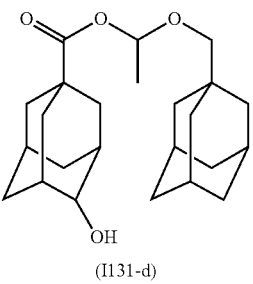
(I131-d)

Feeding 8.48 parts of the compound represented by formula (I131-c) and 42.32 parts of acetonitrile into a reactor, they were stirred at 23° C. for 30 minutes, and then a mixture of 0.42 parts of sodium hydrogenboronate and 6.23 parts of deionized water, further followed by stirring them at 5° C. for 2 hours. To the resulting mixture, 229.77 parts of ethyl acetate and 76.59 parts of deionized water were added thereto, followed by stirring them at 23° C. for 30 minutes, followed by separating into an organic layer. Such washing with water was conducted further five times. The resulting organic layer was concentrated and 48.45 parts of n-heptane was added thereto and stirred, followed by filtrating it to obtain 7.06 parts of compound represented by formula (I131-d).

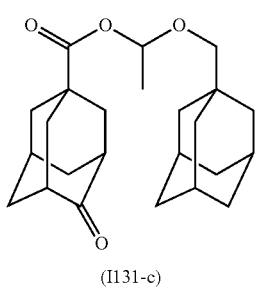

(I131-e) (I131-f)

(I131-g)

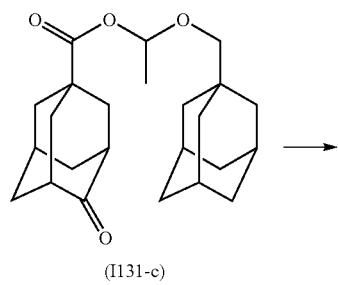
(I131-d)

Example 5

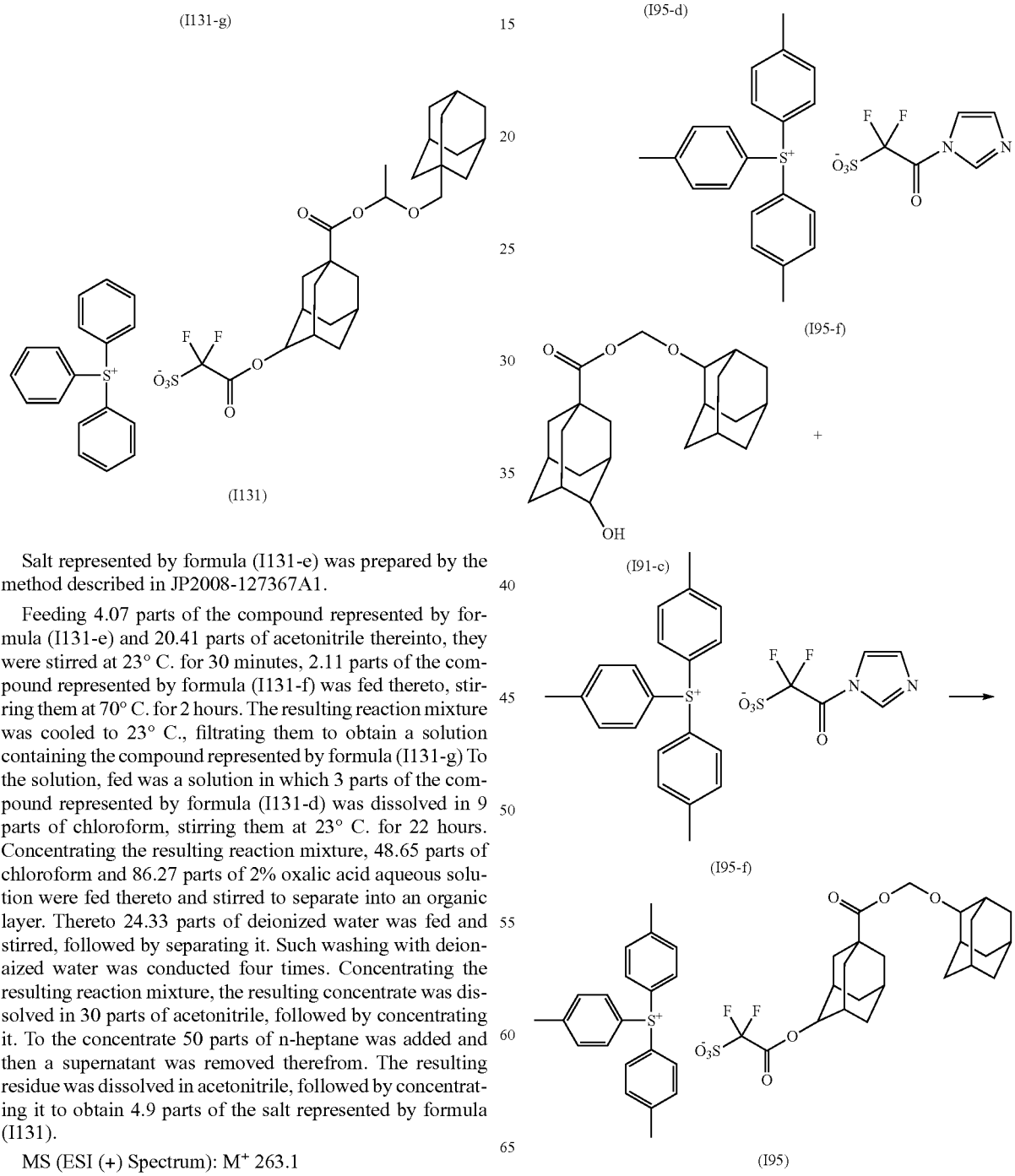

Salt represented by formula (I131-e) was prepared by the method described in JP2008-127367A1.

Feeding 4.07 parts of the compound represented by formula (I131-e) and 20.41 parts of acetonitrile thereinto, they were stirred at 23° C. for 30 minutes, 2.11 parts of the compound represented by formula (I131-f) was fed thereto, stirring them at 70° C. for 2 hours. The resulting reaction mixture was cooled to 23° C., filtrating them to obtain a solution containing the compound represented by formula (I131-g) To the solution, fed was a solution in which 3 parts of the compound represented by formula (I131-d) was dissolved in 9 parts of chloroform, stirring them at 23° C. for 22 hours. Concentrating the resulting reaction mixture, 48.65 parts of chloroform and 86.27 parts of 2% oxalic acid aqueous solution were fed thereto and stirred to separate into an organic layer. Thereto 24.33 parts of deionized water was fed and stirred, followed by separating it. Such washing with deionaized water was conducted four times. Concentrating the resulting reaction mixture, the resulting concentrate was dissolved in 30 parts of acetonitrile, followed by concentrating it. To the concentrate 50 parts of n-heptane was added and then a supernatant was removed therefrom. The resulting residue was dissolved in acetonitrile, followed by concentrating it to obtain 4.9 parts of the salt represented by formula (I131).

MS (ESI (+) Spectrum): M$^+$ 263.1

MS (ESI (−) Spectrum): M$^-$ 545.2

Salt represented by formula (I95-d) was prepared by the method described in JP2008-127367A1. The compound represented by formula (I91-c) was prepared by the method described in Example 3. Feeding 3.28 parts of the compound represented by formula (I95-d) and 15 parts of acetonitrile thereinto, they were stirred at 23° C. for 30 minutes, 1.3 parts of the compound represented by formula (I95-e) was fed thereto, stirring them at 70° C. for 2 hours. The resulting reaction mixture was cooled to 23° C., filtrating them to obtain a solution containing the compound represented by formula (I95-f).

To the solution, fed was a solution in which 2.12 parts of the compound represented by formula (I91-c) was dissolved in 6.36 parts of chloroform, stirring them at 23° C. for 23 hours.

Concentrating the resulting reaction mixture, 60 parts of chloroform and 30 parts of 2% oxalic acid aqueous solution were fed thereto and stirred to separate into an organic layer. Such washing with oxalic acid was conducted twice.

Into the resulting organic layer 30 parts of deionaized water was fed and stirred, followed by separating it. Such washing with deionaized water was conducted five times. The resulting organic layer was concentrated and then 30 parts of acetonitrile was added thereto, followed by concentrating it.

To the concentrate 50 parts of tert-butylmethylether was added and then a supernatant was removed therefrom. The resulting residue was dissolved in acetonitrile, followed by concentrating it to obtain 3.16 parts of the salt represented by formula (I95).

MS (ESI (+) Spectrum): M+ 305.1
MS (ESI (−) Spectrum): M− 517.2

Example 6

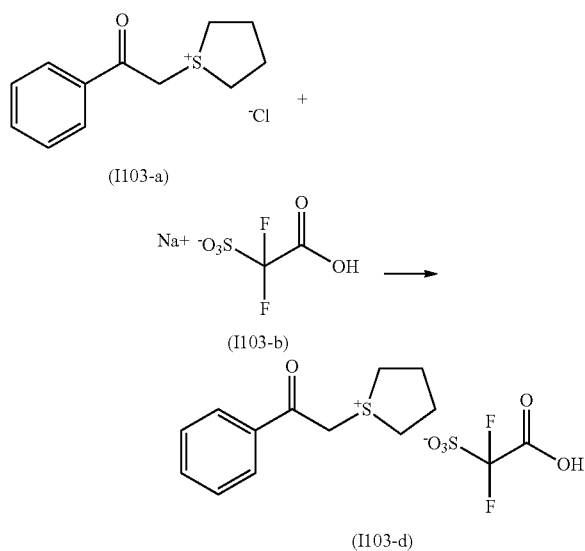

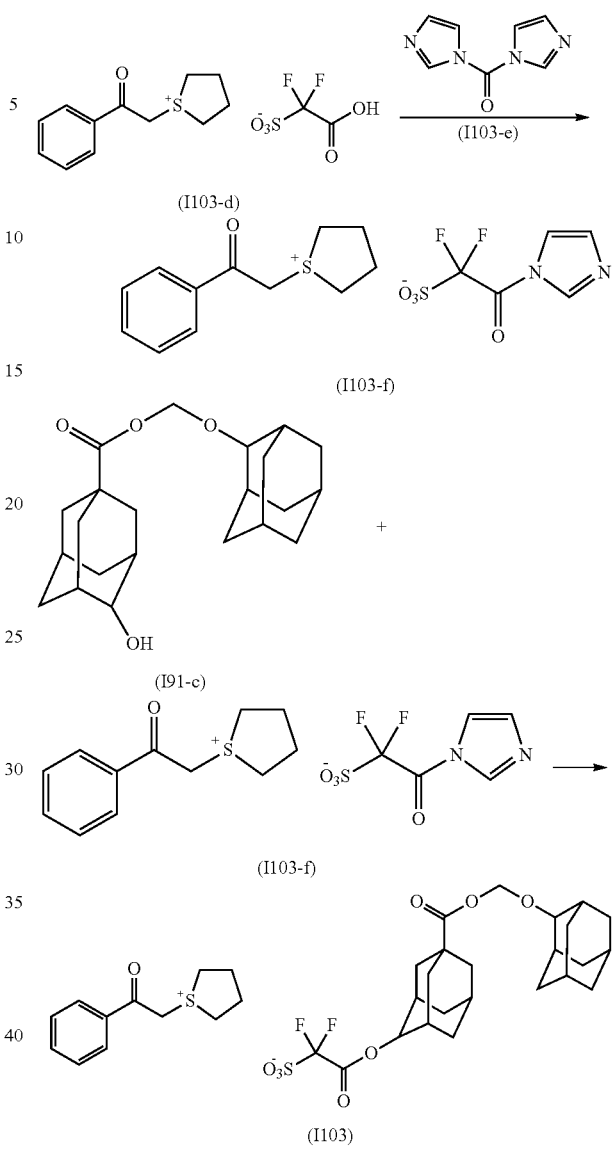

Feeding 10.95 parts of the salt represented by formula (I103-a) and 8.96 parts of the salt represented by formula (I103-b), 100 parts of acetonitrile and 50 parts of deionized water into a reactor, they were stirred at 23° C. for 15 hours. The resulting mixture was concentrated and then extracted with 100 parts of chloroform. The collected organic layer was concentrated to obtain 14.63 parts of compound represented by formula (I103-d).

Feeding 2.61 parts of the compound represented by formula (I103-d) and 15 parts of acetonitrile thereinto, they were stirred at 23° C. for 30 minutes, 1.3 parts of the compound represented by formula (I103-e) was fed thereto, stirring them at 70° C. for 2 hours. The resulting reaction mixture was cooled to 23° C., filtrating them to obtain a solution containing the compound represented by formula (I103-f). The compound represented by formula (I91-c) was prepared by the method described in Example 3. To the solution, fed was a solution in which 2.12 parts of the compound represented by formula (I91-c) was dissolved in 6.36 parts of chloroform, stirring them at 23° C. for 23 hours.

Concentrating the resulting reaction mixture, 60 parts of chloroform and 30 parts of 2% oxalic acid aqueous solution were fed thereto and stirred to separate into an organic layer. Such washing with oxalic acid was conducted twice.

Into the resulting organic layer 30 parts of deionaized water was fed and stirred, followed by separating it. Such washing with deionaized water was conducted five times. The resulting concentrate was concentrated and then 30 parts of acetonitrile was added thereto, followed by concentrating it.

To the concentrate 50 parts of tert-butylmethylether was added and then a supernatant was removed therefrom. The resulting residue was dissolved in acetonitrile, followed by concentrating it to obtain 2.12 parts of the salt represented by formula (I103).

MS (ESI(+) Spectrum): M⁺ 207.1
MS (ESI(−) Spectrum): M⁻ 517.2

Example 7

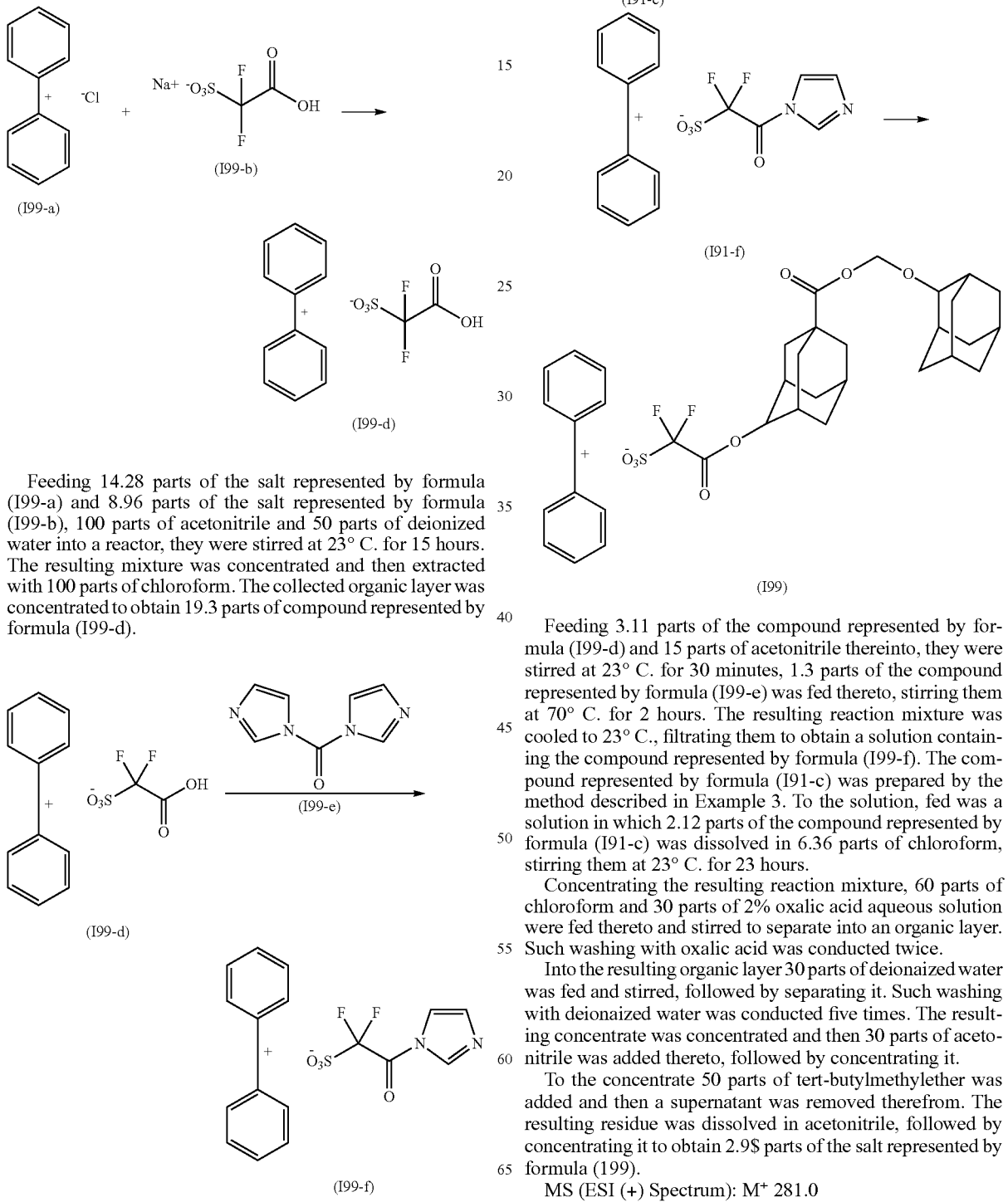

Feeding 14.28 parts of the salt represented by formula (I99-a) and 8.96 parts of the salt represented by formula (I99-b), 100 parts of acetonitrile and 50 parts of deionized water into a reactor, they were stirred at 23° C. for 15 hours. The resulting mixture was concentrated and then extracted with 100 parts of chloroform. The collected organic layer was concentrated to obtain 19.3 parts of compound represented by formula (I99-d).

Feeding 3.11 parts of the compound represented by formula (I99-d) and 15 parts of acetonitrile thereinto, they were stirred at 23° C. for 30 minutes, 1.3 parts of the compound represented by formula (I99-e) was fed thereto, stirring them at 70° C. for 2 hours. The resulting reaction mixture was cooled to 23° C., filtrating them to obtain a solution containing the compound represented by formula (I99-f). The compound represented by formula (I91-c) was prepared by the method described in Example 3. To the solution, fed was a solution in which 2.12 parts of the compound represented by formula (I91-c) was dissolved in 6.36 parts of chloroform, stirring them at 23° C. for 23 hours.

Concentrating the resulting reaction mixture, 60 parts of chloroform and 30 parts of 2% oxalic acid aqueous solution were fed thereto and stirred to separate into an organic layer. Such washing with oxalic acid was conducted twice.

Into the resulting organic layer 30 parts of deionaized water was fed and stirred, followed by separating it. Such washing with deionaized water was conducted five times. The resulting concentrate was concentrated and then 30 parts of acetonitrile was added thereto, followed by concentrating it.

To the concentrate 50 parts of tert-butylmethylether was added and then a supernatant was removed therefrom. The resulting residue was dissolved in acetonitrile, followed by concentrating it to obtain 2.9$ parts of the salt represented by formula (I99).

MS (ESI (+) Spectrum): M⁺ 281.0
MS (ESI (−) Spectrum): M⁻ 517.2

Resin Synthesis Example 1

To 11.18 parts of 2-ethyl-2-amadantyl methacrylate, 4.6 parts of p-acetoxystylene and 3.55 parts of 3-hydroxy-1-amadantyl methacrylate, 28.82 parts of 1,4-dioxane was mixed and the obtained solution was heated to 87° C. To the resulting solution, 2.96 parts of azobisisobutyronitrile was added as an initiator, and the resulting reaction mixture was heated at 87° C. for 6 hours.

After cooling the mixture, it was poured into 291 parts of methanol and 124.89 parts of water to cause precipitation and then filtrate it. To the filtrate added were 2.93 parts of 2-dimethylaminopyridine and then the same amount of methanol as that of the filtrate, followed by being heated to reflux for 15 hours. After cooling the resultant mixture, 2.16 parts of glacial acetic acid was added thereto to conduct neutralization, followed by pouring a large amount of water to cause precipitation. The step of filtrating the precipitated polymer and dissolving it in acetone, followed by pouring a large amount of water to cause precipitation was conducted three times, and then purified to obtain 27.71 parts of a polymer having a weight-average molecular weight of about $3.4 \times 10^3$. This resin is called as resin A1.

Resin Synthesis Example 2

To 10.54 parts of 2-methyl-2-amadantyl methacrylate, 14.6 parts of p-acetoxystylene and 3.55 parts of 3-hydroxy-1-amadantyl methacrylate, 47.09 parts of 1,4-dioxane was mixed and the obtained solution was heated to 87° C. To the resulting solution, 2.96 parts of azobisisobutyronitrile was added as an initiator, and the resulting reaction mixture was heated at 87° C. for 6 hours.

After cooling the mixture, it was poured into 285.67 parts of methanol and 122.43 parts of deionized water to cause precipitation and then filtrate it. To the filtrate added were 2.93 parts of 4-dimethylaminopyridine and then the same amount of methanol as that of the filtrate, followed by being heated to reflux for 15 hours. After cooling the resultant mixture, 2.16 parts of glacial acetic acid was added thereto to conduct neutralization, followed by pouring a large amount of water to cause precipitation. The step of filtrating the precipitated polymer and dissolving it in acetone, followed by pouring a large amount of water to cause precipitation was conducted three times, and then purified to obtain 28.15 parts of a polymer having a weight-average molecular weight of about $3.7 \times 10^3$. This resin is called as resin A2.

Resin Synthesis Example 3

To 10.54 parts of 2-methyl-2-amadantyl methacrylate, 14.6 parts of p-acetoxystylene and 1.56 parts of stylene, 44.12 parts of 1,4-dioxane was mixed and the obtained solution was heated to 87° C. To the resulting solution, 0.69 parts of azobisisobutyronitrile was added as an initiator, and the resulting reaction mixture was heated at 87° C. for 6 hours.

After cooling the mixture, it was poured into 267.63 parts of methanol and 114.70 parts of deionized water to cause precipitation and then filtrate it. To the filtrate added was 2.67 parts of 2-dimethylaminopyridine and then the same amount of methanol as that of the filtrate, followed by being heated to reflux for 15 hours. After cooling the resultant mixture, 1.31 parts of glacial acetic acid was added thereto to conduct neutralization, followed by pouring a large amount of water to cause precipitation. The step of filtrating the precipitated polymer and dissolving it in acetone, followed by pouring a large amount of water to cause precipitation was conducted three times, and then purified to obtain 25.16 parts of a polymer having a weight-average molecular weight of about $3.3 \times 10^3$. This resin is called as resin A3.

Resin Synthesis Example 4

To 11.18 parts of 2-ethyl-2-amadantyl methacrylate, 15.09 parts of p-acetoxystylene and 3.55 parts of 3-hydroxy-1-amadantyl methacrylate, 28.82 parts of 1,4-dioxane was mixed and the obtained solution was heated to 82° C. To the resulting solution, 0.86 parts of azobisisobutyronitrile was added as an initiator, and the resulting reaction mixture was heated at 82° C. for 6 hours.

After cooling the mixture, it was poured into a mixture of 291.41 parts of methanol and 124.89 parts of deionized water to cause precipitation and then filtrate it. To the filtrate added was 2.93 parts of 2-dimethylaminopyridine and then the same amount of methanol as that of the filtrate, followed by being heated to reflux for 15 hours. After cooling the resultant mixture, 2.16 parts of glacial acetic acid was added thereto to conduct neutralization, followed by pouring a large amount of water to cause precipitation. The step of filtrating the precipitated polymer and dissolving it in acetone, followed by pouring a large amount of water to cause precipitation was conducted three times, and then purified to obtain 22.42 parts of a polymer having a weight-average molecular weight of about $8.5 \times 10^3$. This resin is called as resin A4.

Examples 8 to 24 and Comparative Examples 1 to 2

(Preparation of Photoresist Composition)

The following components were mixed and dissolved, further, filtrated through a fluorine resin filter having pore diameter of 0.2 μm, to prepare photoresist compositions shown in Table 6.

<Resin>

Resin A1, Resin A2, Resin A3, Resin A4

<Acid Generator>

I-1: Salt represented by formula (I1)

I-61: Salt represented by formula (I61)

I-91: Salt represented by formula (I91)

I-131: Salt represented by formula (I131)

I-95: Salt represented by formula (I95)

I-103: Salt represented by formula (I103)

I-99: Salt represented by formula (I199)

B1:

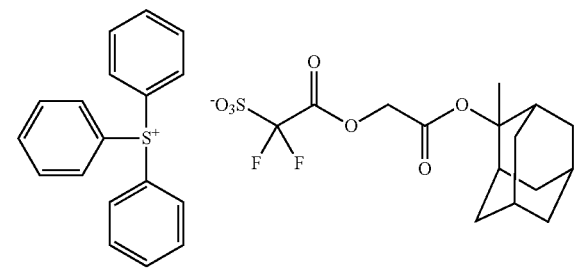

<Quencher>

Basic compound C1: tetrabutylammonium hydroxide

Basic compound C2:

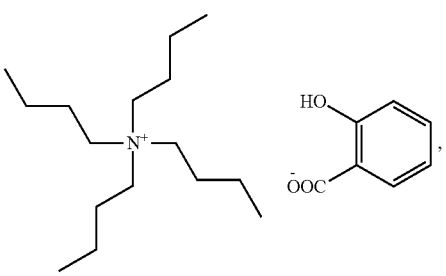

<Solvent>

| propylene glycol monomethyl ether acetate | 400 parts |
|---|---|
| propylene glycol monomethyl ether | 100 parts |
| γ-butyrolactone | 5.5 parts |

TABLE 6

| | Acid generator (Parts) | Resin (Parts) | Quencher (Parts) | PB/PEB |
|---|---|---|---|---|
| Ex. 8 | I-1 (3) | A1 (10) | C2 (0.3) | 120° C./120° C. |
| Ex. 9 | I-1 (3) | A2 (10) | C2 (0.3) | 120° C./120° C. |
| Ex. 10 | I-1 (3) | A3 (10) | C2 (0.3) | 120° C./120° C. |
| Ex. 11 | I-1 (3) | A4 (10) | C2 (0.3) | 120° C./120° C. |
| Ex. 12 | I-1 (3) | A4 (10) | C1 (0.3) | 120° C./120° C. |
| Ex. 13 | I-61 (3) | A1 (10) | C2 (0.3) | 120° C./120° C. |
| Ex. 14 | I-61 (3) | A2 (10) | C2 (0.3) | 120° C./120° C. |
| Ex. 15 | I-91 (3) | A1 (10) | C2 (0.3) | 120° C./120° C. |
| Ex. 16 | I-91 (3) | A2 (10) | C2 (0.3) | 120° C./120° C. |
| Ex. 17 | I-131 (3) | A1 (10) | C2 (0.3) | 120° C./120° C. |
| Ex. 18 | I-131 (3) | A2 (10) | C2 (0.3) | 120° C./120° C. |
| Ex. 19 | I-95 (3) | A1 (10) | C2 (0.3) | 120° C./120° C. |
| Ex. 20 | I-95 (3) | A2 (10) | C2 (0.3) | 120° C./120° C. |
| Ex. 21 | I-103 (3) | A1 (10) | C2 (0.3) | 120° C./120° C. |
| Ex. 22 | I-103 (3) | A2 (10) | C2 (0.3) | 120° C./120° C. |
| Ex. 23 | I-95/I-99 (1/2) | A1 (10) | C2 (0.3) | 120° C./120° C. |
| Ex. 24 | I-95/I-99 (1/2) | A2 (10) | C2 (0.3) | 120° C./120° C. |
| Compar. Ex. 1 | B1 (3) | A1 (10) | C2 (0.3) | 120° C./120° C. |
| Compar. Ex. 2 | B1 (3) | A4 (10) | C1 (0.3) | 120° C./120° C. |

(Evaluation by Electron Beam Lithography)

Silicon wafers (12 inches) were each coated with hexamethyldisilazane and then baked at 90° C. for 60 seconds on a direct hotplate. Each of the photoresist compositions prepared as above was spin-coated over hexamethyldisilazane coating so that the thickness of the resulting film after drying became 60 nm.

The silicon wafers thus coated with the respective photoresist compositions were each prebaked on a direct hotplate at a temperature shown in the column "PB" in Table 6 for 60 seconds. Using an electron beam lithography system ("HL-800D 50 keV" manufactured by HITACHI), each wafer thus formed with the respective resist film was subjected to line and space pattern exposure with the exposure quantity being varied stepwise.

After the exposure, each wafer was subjected to post-exposure baking on a hotplate at a temperature shown in the column "PEB" in Table 6 for 60 seconds and then to paddle development for 60 seconds with an aqueous solution of 2.38 wt % tetramethylammonium hydroxide.

Line Edge Roughness (LER):

The photoresist pattern was made by such exposure as the line width of the line and space pattern of 80 nm became 1:1 after exposure through line and space pattern mask and development.

The photoresist pattern was observed with a scanning electron microscope. The difference between the height of the highest point and the height of the lowest point of the scabrous wall surface of the photoresist pattern was measured. Further, each of the differences is also shown in parentheses in a column of "LER". The smaller the difference is, the better the pattern is. The difference was shown in parentheses in Table 7.

The differences are marked by "◯" when the difference is 5 nm or less and by "X" when the difference is over 5 nm.

TABLE 7

| Ex. No. | LER |
|---|---|
| Ex. 8 | ◯ (3.89) |
| Ex. 9 | ◯ (3.86) |
| Ex. 10 | ◯ (3.96) |
| Ex. 11 | ◯ (4.28) |
| Ex. 12 | ◯ (4.52) |
| Ex. 13 | ◯ (3.84) |
| Ex. 14 | ◯ (3.83) |
| Ex. 15 | ◯ (3.80) |
| Ex. 16 | ◯ (3.79) |
| Ex. 17 | ◯ (3.83) |
| Ex. 18 | ◯ (3.80) |
| Ex. 19 | ◯ (3.56) |
| Ex. 20 | ◯ (3.52) |
| Ex. 21 | ◯ (3.98) |
| Ex. 22 | ◯ (3.82) |
| Ex. 23 | ◯ (3.68) |
| Ex. 24 | ◯ (3.59) |
| Compar. Ex. 1 | X (5.16) |
| Compar. Ex. 2 | X (5.42) |

(Evaluation by Extreme Ultraviolet Exposure)

Silicon wafers (12 inches) were each coated with hexamethyldisilazane and then baked at 90° C. for 60 seconds on a direct hotplate. Each of the photoresist compositions prepared as above was spin-coated over the anti-reflective coating so that the thickness of the resulting photoresist film after drying became 50 nm. The silicon wafers thus coated with the respective photoresist compositions were each prebaked on a direct hotplate at a temperature shown in the column "PB" in Table 6 for 60 seconds. Using an extreme ultraviolet exposure system, each wafer thus formed with the respective resist film was subjected to line and space pattern exposure with the exposure quantity being varied stepwise.

After the exposure, each wafer was subjected to post-exposure baking on a hotplate at a temperature shown in the column "PEB" in Table 6 for 60 seconds and then to paddle development for 60 seconds with an aqueous solution of 2.38 wt % tetramethylammonium hydroxide.

Line Edge Roughness (LER):

The photoresist pattern was made by such exposure as the line width of the line and space pattern of 50 nm became 1.1 after exposure through line and space pattern mask and development, The photoresist pattern was observed with a scanning electron microscope. The difference between the height of the highest point and the height of the lowest point of the scabrous wall surface of the photoresist pattern was measured. Further, each of the differences is also shown in parentheses in a column of "LER". The smaller the difference is, the better the pattern is. The difference was shown in parentheses in Table 8.

The differences are marked by "◯" when the difference is 5 nm or less and by "X" when the difference is over 5 nm.

TABLE 7

| Ex. No. | LER |
|---------|-----|
| Ex. 5   | ○ (3.87) |
| Ex. 10  | ○ (3.67) |
| Ex. 12  | ○ (3.62) |
| Ex. 14  | ○ (3.65) |

The salt of the present invention is suitable for an acid generator and the photoresist composition comprising the salt of the present invention provides a good photoresist pattern with less line edge roughness.

What is claimed is:

1. A salt represented by formula (I):

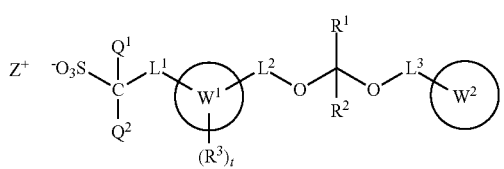

wherein $Q^1$ and $Q^2$ each independently represent a fluorine atom or a C1-C6 perfluoroalkyl group, $L^1$ represents a moiety represented by any one of formulae (b1-1), (b1-2), (b1-3), (b1-5), (b1-6) and (b1-7):

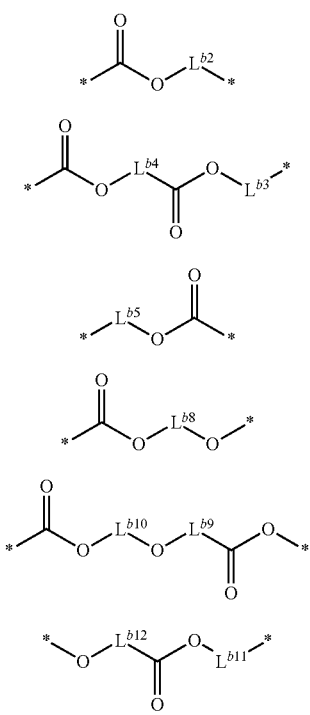

wherein $L^{b2}$ represents a single bond or a C1-C15 divalent hydrocarbon group, $L^{b3}$ represents a single bond or a C1-C12 divalent hydrocarbon group, $L^{b4}$ represents a C1-C13 divalent hydrocarbon group provided that the total carbon atoms of $L^{b3}$ and $L^{b4}$ is up to 13, $L^{b5}$ represents a C1-C15 divalent hydrocarbon group, $L^{b8}$ represents C1-C14 divalent hydrocarbon group, $L^{b9}$ represents a single bond or a C1-C11 saturated hydrocarbon group, $L^{b10}$ represents a C1-C12 divalent hydrocarbon group, with the proviso that total carbon number of $L^{b9}$ and $L^{b10}$ is up to 12, $L^{b11}$ represents a single bond or a C1-C13 divalent hydrocarbon group, $L^{b12}$ represents C1-C14 divalent hydrocarbon group, with the proviso that total carbon number of $L^{b11}$ and $L^{b12}$ is up to 14,

* represents a binding position, * of the left side represents a binding position to —$C(Q^1)(Q^2)$-, and * of the right side represents a binding position to the ring $W^1$, $L^2$ and $L^3$ each independently represent a single bond or a C1-C6 divalent saturated alkyl group in which a methylene group may be replaced by an oxygen atom or a carbonyl group, ring $W^1$ and ring $W^2$ each independently represent a C3-C36 hydrocarbon ring, $R^1$ and $R^2$ each independently represent a hydrogen atom or C1-C6 alkyl group, $R^3$ represents a C1-C6 alkyl group, t represents an integer of 0 to 2, and $Z^+$ represents an organic counter ion.

2. The salt according to claim 1, wherein $L^1$ represents *—CO—O—, where * represents a binding position to —$C(Q^1)(Q^2)$-.

3. The salt according to claim 1 or 2, wherein $L^2$ is a carbonyl group.

4. The salt according to claim 1 or 2, wherein $L^3$ is a single bond or a methylene group.

5. An acid generator comprising the salt according to claim 1 or 2.

6. A photoresist composition comprising the acid generator according to claim 5 and a resin having an acid-labile group, being insoluble or poorly soluble in an aqueous alkali solution but becoming soluble in an aqueous alkali solution by the action of an acid.

7. The photoresist composition according to claim 6, which further comprises a basic compound.

8. A process for producing a photoresist pattern comprising the following steps (1) to (5):
   (1) a step of applying the photoresist composition according to claim 6 on a substrate,
   (2) a step of forming a photoresist film by conducting drying,
   (3) a step of exposing the photoresist film to radiation,
   (4) a step of baking the exposed photoresist film, and
   (5) a step of developing the baked photoresist film with an alkaline developer, thereby forming a photoresist pattern.

* * * * *